(12) United States Patent
Singh et al.

(10) Patent No.: US 12,391,833 B2
(45) Date of Patent: Aug. 19, 2025

(54) POLYMERIC DYES WITH LINKER GROUPS COMPRISING DEOXYRIBOSE

(71) Applicant: SONY GROUP CORPORATION, Tokyo (JP)

(72) Inventors: Sharat Singh, Los Altos Hills, CA (US); Tracy Matray, Snohomish, WA (US); Michael Vanbrunt, Bothell, WA (US); John McCutcheon, Shoreline, WA (US)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 18/678,656

(22) Filed: May 30, 2024

(65) Prior Publication Data

US 2024/0318004 A1 Sep. 26, 2024

Related U.S. Application Data

(63) Continuation of application No. 17/255,353, filed as application No. PCT/US2019/039582 on Jun. 27, 2019, now Pat. No. 12,006,438.

(Continued)

(51) Int. Cl.
*C09B 69/00* (2006.01)
*C07H 21/04* (2006.01)
(Continued)

(52) U.S. Cl.
CPC ........... *C09B 69/102* (2013.01); *C07H 21/04* (2013.01); *C09B 69/109* (2013.01); *G01N 33/582* (2013.01)

(58) Field of Classification Search
CPC ... C09B 69/102; C09B 69/109; C09B 69/103; C07H 21/04; G01N 33/582
(Continued)

(56) References Cited

U.S. PATENT DOCUMENTS 4,450,305 A 5/1984 Kamhi
4,476,229 A 10/1984 Fino et al.
(Continued)

FOREIGN PATENT DOCUMENTS

CA 2263671 A1 2/1998
CN 102174078 A 9/2011
(Continued)

OTHER PUBLICATIONS

"What is an Analyte?," Google Search, dated Mar. 22, 2018, retrieved from https://www.google.com/search?q=what+is+an+analyte&rlz=1CIGCEB_enUS775US775&oq=what+is+an+analyte&aqs=chrome..69i57j0l5.3231j0j7&s . . . 2 pages.
(Continued)

*Primary Examiner* — Eisa B Elhilo
(74) *Attorney, Agent, or Firm* — Seed IP Law Group LLP

(57) ABSTRACT

Compounds useful as fluorescent or colored dyes are disclosed. The compounds have the following structure (I):

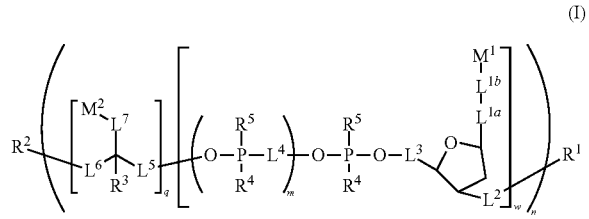

or a stereoisomer, tantomer or salt thereof, wherein $R^1$, $R^2$, $R^3$, $R^4$, $R^5$, $L^{1a}$, $L^{1b}$, $L^2$, $L^3$, $L^4$, $L^5$, $L^6$, $L^7$, $M^1$, $M^2$, q, w, m and n are as defined herein. Methods associated with preparation and use of such compounds are also provided.

20 Claims, 2 Drawing Sheets

Related U.S. Application Data

(60) Provisional application No. 62/690,656, filed on Jun. 27, 2018.

(51) Int. Cl.
   *C09B 69/10* (2006.01)
   *G01N 33/58* (2006.01)

(58) Field of Classification Search
   USPC .................................................. 8/552
   See application file for complete search history.

(56) References Cited

U.S. PATENT DOCUMENTS

| | | |
|---|---|---|
| 4,778,753 A | 10/1988 | Yamanishi et al. |
| 5,053,054 A | 10/1991 | Kirchanski |
| 5,268,486 A | 12/1993 | Waggoner et al. |
| 5,318,894 A | 6/1994 | Pugia |
| 5,582,977 A | 12/1996 | Yue et al. |
| 5,696,157 A | 12/1997 | Wang et al. |
| 5,698,391 A | 12/1997 | Cook et al. |
| 5,886,177 A | 3/1999 | Cook et al. |
| 5,994,143 A | 11/1999 | Bieniarz et al. |
| 6,005,093 A | 12/1999 | Wood et al. |
| 6,140,480 A | 10/2000 | Kool |
| 6,171,859 B1 | 1/2001 | Herrnstadt et al. |
| 6,218,108 B1 | 4/2001 | Kool |
| 6,365,730 B1 | 4/2002 | Jennings et al. |
| 6,380,431 B1 | 4/2002 | Whipple et al. |
| 6,479,650 B1 | 11/2002 | Kool |
| 6,514,700 B1 | 2/2003 | Singh |
| 6,534,041 B1 | 3/2003 | Licha et al. |
| 6,627,400 B1 | 9/2003 | Singh et al. |
| 6,670,193 B2 | 12/2003 | Kool |
| 6,716,452 B1 | 4/2004 | Piccariello et al. |
| 6,852,709 B2 | 2/2005 | Leong et al. |
| 7,038,063 B2 | 5/2006 | Lee et al. |
| 7,060,708 B2 | 6/2006 | Piccariello et al. |
| 7,172,907 B2 | 2/2007 | Chen et al. |
| 7,423,133 B2 | 9/2008 | Kool et al. |
| 7,667,024 B2 | 2/2010 | Mao et al. |
| 7,897,684 B2 | 3/2011 | Bazan et al. |
| 8,008,522 B2 | 8/2011 | Lukhtanov et al. |
| 8,101,776 B2 | 1/2012 | Berens et al. |
| 8,153,706 B2 | 4/2012 | Vasudevan |
| 8,217,389 B2 | 7/2012 | Nakano et al. |
| 8,293,700 B2 | 10/2012 | Arranz |
| 8,349,308 B2 | 1/2013 | Yurkovetskiy et al. |
| 8,354,515 B2 | 1/2013 | Ueno et al. |
| 8,431,545 B2 | 4/2013 | Kataoka et al. |
| 8,491,993 B2 | 7/2013 | Nguyen et al. |
| 8,546,590 B2 | 10/2013 | Gall |
| 8,632,947 B2 | 1/2014 | Bentley et al. |
| 8,802,738 B2 | 8/2014 | Emrick |
| 8,895,023 B2 | 11/2014 | Rademacher et al. |
| 8,906,603 B2 | 12/2014 | Castro et al. |
| 8,946,394 B2 | 2/2015 | Na et al. |
| 9,029,537 B2 | 5/2015 | Koch |
| 9,085,799 B2 | 7/2015 | Bazan et al. |
| 9,150,782 B2 | 10/2015 | Lee et al. |
| 9,400,273 B1 | 7/2016 | Liu et al. |
| 9,545,447 B2 | 1/2017 | Wooley et al. |
| 9,649,389 B2 | 5/2017 | Groves et al. |
| 9,687,291 B2 | 6/2017 | Shimizu et al. |
| 9,689,877 B2 | 6/2017 | Matray et al. |
| 9,696,310 B2 | 7/2017 | Margulies et al. |
| 9,714,946 B2 | 7/2017 | Bradner et al. |
| 9,765,220 B2 | 9/2017 | Matray et al. |
| 9,822,134 B2 | 11/2017 | Segev |
| 9,851,359 B2 | 12/2017 | Matray et al. |
| 9,884,070 B2 | 2/2018 | Denardo et al. |
| 9,910,051 B2 | 3/2018 | Beacham et al. |
| 9,913,992 B2 | 3/2018 | Demarest et al. |
| 9,932,578 B2 | 4/2018 | Feinstein et al. |
| 9,939,454 B2 | 4/2018 | Dzubay et al. |
| 10,036,754 B2 | 7/2018 | Matray et al. |
| 10,191,060 B2 | 1/2019 | Chiu et al. |
| 10,435,563 B2 | 10/2019 | Matray et al. |
| 10,617,670 B2 | 4/2020 | Sapra et al. |
| 10,709,791 B2 | 7/2020 | Stayton et al. |
| 10,834,091 B2 | 11/2020 | Deninno et al. |
| 10,865,310 B2 | 12/2020 | Matray et al. |
| 10,866,244 B2 | 12/2020 | Matray et al. |
| 10,954,391 B2 | 3/2021 | Matray et al. |
| 10,989,715 B2 | 4/2021 | Matray et al. |
| 11,013,756 B2 | 5/2021 | Haruta et al. |
| 11,084,932 B2 | 8/2021 | Battrell et al. |
| 11,142,647 B2 | 10/2021 | Matray et al. |
| 11,312,736 B1 | 4/2022 | Matray et al. |
| 11,352,502 B2 | 6/2022 | Matray et al. |
| 11,370,922 B2 | 6/2022 | Matray et al. |
| 11,377,563 B2 | 7/2022 | Matray et al. |
| 11,390,754 B2 | 7/2022 | Singh et al. |
| 11,434,374 B2 | 9/2022 | Matray et al. |
| 11,434,377 B2 | 9/2022 | Matray et al. |
| 11,453,783 B2 | 9/2022 | Matray et al. |
| 11,618,906 B2 | 4/2023 | Steele et al. |
| 11,685,835 B2 * | 6/2023 | Matray ............. G01N 33/5005 436/172 |
| 11,827,661 B2 | 11/2023 | Battrell et al. |
| 11,874,280 B2 | 1/2024 | Jackson et al. |
| 11,931,419 B2 | 3/2024 | Matray |
| 11,945,955 B2 | 4/2024 | Matray et al. |
| 12,006,438 B2 | 6/2024 | Singh et al. |
| 12,018,159 B2 | 6/2024 | Matray et al. |
| 2001/0018503 A1 | 8/2001 | Whipple et al. |
| 2002/0012947 A1 | 1/2002 | Bevers et al. |
| 2002/0099013 A1 | 7/2002 | Piccariello et al. |
| 2002/0142329 A1 * | 10/2002 | Matray ................. C07H 21/00 435/7.1 |
| 2003/0054361 A1 | 3/2003 | Heller |
| 2003/0207208 A1 | 11/2003 | Uenishi |
| 2003/0207264 A1 | 11/2003 | Packard et al. |
| 2004/0014981 A1 | 1/2004 | Lugade et al. |
| 2004/0067498 A1 * | 4/2004 | Chenna ................. C07H 21/00 435/6.12 |
| 2004/0096825 A1 * | 5/2004 | Chenna ................. C07H 19/06 435/6.12 |
| 2004/0138467 A1 | 7/2004 | French et al. |
| 2004/0224372 A1 | 11/2004 | Li et al. |
| 2004/0241768 A1 | 12/2004 | Whitten et al. |
| 2005/0054024 A1 | 3/2005 | Lawrence |
| 2005/0123935 A1 | 6/2005 | Haugland et al. |
| 2006/0008822 A1 | 1/2006 | Manoharan et al. |
| 2006/0035302 A1 | 2/2006 | Lee |
| 2006/0063186 A1 | 3/2006 | Benson et al. |
| 2007/0042398 A1 | 2/2007 | Peng et al. |
| 2007/0077549 A1 | 4/2007 | Buller et al. |
| 2007/0148094 A1 | 6/2007 | Uzgiris |
| 2007/0269902 A1 | 11/2007 | Beechem et al. |
| 2008/0227939 A1 | 9/2008 | Mizoshita et al. |
| 2009/0253792 A1 | 10/2009 | Mickle et al. |
| 2009/0299070 A1 | 12/2009 | Berens et al. |
| 2010/0039684 A1 | 2/2010 | Kolb et al. |
| 2010/0092386 A1 | 4/2010 | Segev |
| 2010/0129800 A1 | 5/2010 | Aymami Bofarull et al. |
| 2010/0192312 A1 | 8/2010 | Cremer et al. |
| 2010/0248385 A1 | 9/2010 | Tan et al. |
| 2011/0014599 A1 | 1/2011 | Akhavan-Tafti et al. |
| 2011/0144065 A1 | 6/2011 | Denardo et al. |
| 2011/0224516 A1 | 9/2011 | Romey et al. |
| 2012/0021454 A1 | 1/2012 | Bikker et al. |
| 2012/0116079 A1 | 5/2012 | Lukhtanov et al. |
| 2012/0126175 A1 | 5/2012 | Ueno et al. |
| 2013/0059343 A1 | 3/2013 | Cheung |
| 2013/0119363 A1 | 5/2013 | Sasaki et al. |
| 2013/0137755 A1 | 5/2013 | Segev |
| 2013/0202536 A1 | 8/2013 | Mustaev et al. |
| 2013/0244891 A1 | 9/2013 | Waggoner et al. |
| 2014/0023590 A1 | 1/2014 | Gao et al. |
| 2014/0193504 A1 | 7/2014 | Wooley et al. |
| 2014/0275508 A1 | 9/2014 | Scarr et al. |
| 2015/0030541 A1 | 1/2015 | Rogers |
| 2015/0110715 A1 | 4/2015 | Eder et al. |

(56) References Cited

U.S. PATENT DOCUMENTS

| | | | |
|---|---|---|---|
| 2015/0159198 A1* | 6/2015 | McGall | C12N 9/1252 |
| | | | 435/6.12 |
| 2015/0232615 A1 | 8/2015 | Kwiatkowski | |
| 2015/0258217 A1 | 9/2015 | Caravan | |
| 2016/0039850 A1 | 2/2016 | Segev | |
| 2016/0176903 A1 | 6/2016 | Segev | |
| 2016/0264737 A1 | 9/2016 | Bartholomew et al. | |
| 2016/0327859 A1 | 11/2016 | Idei et al. | |
| 2016/0347907 A1 | 12/2016 | Dose | |
| 2017/0292957 A1* | 10/2017 | Matray | C07F 9/572 |
| 2017/0326233 A1 | 11/2017 | Demeule et al. | |
| 2018/0065998 A1 | 3/2018 | Battrell et al. | |
| 2018/0092993 A1 | 4/2018 | Desai et al. | |
| 2018/0141935 A1 | 5/2018 | Josel et al. | |
| 2018/0312468 A1 | 11/2018 | Zhang et al. | |
| 2019/0136065 A1 | 5/2019 | Singh et al. | |
| 2019/0144678 A1 | 5/2019 | Matray et al. | |
| 2019/0153232 A1 | 5/2019 | Matray et al. | |
| 2019/0300716 A1 | 10/2019 | Matray et al. | |
| 2020/0032139 A1 | 1/2020 | Behrendt et al. | |
| 2020/0164085 A1 | 5/2020 | Brandish et al. | |
| 2020/0222554 A1 | 7/2020 | Matray et al. | |
| 2020/0330610 A1 | 10/2020 | Desai et al. | |
| 2020/0353089 A1 | 11/2020 | Matray | |
| 2020/0353094 A1 | 11/2020 | Matray | |
| 2020/0360526 A1 | 11/2020 | Matray | |
| 2021/0032277 A1 | 2/2021 | Matray et al. | |
| 2021/0032474 A1 | 2/2021 | Matray et al. | |
| 2021/0095130 A1 | 4/2021 | Matray et al. | |
| 2021/0096135 A1 | 4/2021 | Matray et al. | |
| 2021/0109104 A1 | 4/2021 | Jackson et al. | |
| 2021/0128591 A1 | 5/2021 | Matray | |
| 2021/0128739 A1 | 5/2021 | Matray | |
| 2021/0139440 A1 | 5/2021 | Ramsden et al. | |
| 2021/0253864 A1 | 8/2021 | Matray et al. | |
| 2021/0261782 A1 | 8/2021 | Matray et al. | |
| 2021/0285953 A1 | 9/2021 | Matray et al. | |
| 2021/0340380 A1 | 11/2021 | Matray et al. | |
| 2021/0395530 A1 | 12/2021 | Matray et al. | |
| 2022/0160887 A1 | 5/2022 | Matray et al. | |
| 2022/0168433 A1 | 6/2022 | Matray et al. | |
| 2022/0168435 A1 | 6/2022 | Matray et al. | |
| 2022/0175951 A1 | 6/2022 | Boitano et al. | |
| 2022/0227794 A1 | 7/2022 | Matray et al. | |
| 2022/0305127 A1 | 9/2022 | Thomas et al. | |
| 2022/0372297 A1 | 11/2022 | Matray et al. | |
| 2022/0380603 A1 | 12/2022 | Matray et al. | |
| 2022/0402963 A1 | 12/2022 | Matray et al. | |
| 2023/0012304 A1 | 1/2023 | Matray et al. | |
| 2023/0129481 A1 | 4/2023 | Matray et al. | |
| 2024/0043455 A1 | 2/2024 | Battrell et al. | |
| 2024/0092820 A1 | 3/2024 | Matray et al. | |
| 2024/0132725 A1 | 4/2024 | Sherif | |
| 2024/0207423 A1 | 6/2024 | Matray | |
| 2024/0210408 A1 | 6/2024 | Jackson et al. | |
| 2024/0248094 A1 | 7/2024 | Matray et al. | |
| 2024/0255514 A1 | 8/2024 | Matray et al. | |
| 2024/0287313 A1 | 8/2024 | Sherif | |
| 2024/0287314 A1 | 8/2024 | Matray et al. | |
| 2024/0327440 A1 | 10/2024 | Jackson et al. | |

FOREIGN PATENT DOCUMENTS

| | | | |
|---|---|---|---|
| CN | 103319378 A | 9/2013 | |
| CN | 104072727 A | 10/2014 | |
| CN | 105377994 A | 3/2016 | |
| CN | 106589005 A | 4/2017 | |
| CN | 107106685 A | 8/2017 | |
| CN | 107454903 A | 12/2017 | |
| CN | 107709470 A | 2/2018 | |
| CN | 109153860 A | 1/2019 | |
| EP | 0708837 B1 | 3/2006 | |
| GB | 2 372 256 A | 8/2002 | |
| GB | 2 554 666 A | 4/2018 | |
| JP | S61207395 A | 9/1986 | |
| JP | H04282391 A | 10/1992 | |
| JP | 2000017183 A | 1/2000 | |
| JP | 2003532092 A | 10/2003 | |
| JP | 2014527071 A | 10/2014 | |
| JP | 2016534107 A | 11/2016 | |
| JP | 2017504659 A | 2/2017 | |
| JP | 2017124994 A | 7/2017 | |
| JP | 2018507863 A | 3/2018 | |
| JP | 2018512167 A | 5/2018 | |
| JP | 2018515628 A | 6/2018 | |
| JP | 2019516807 A | 6/2019 | |
| JP | 2019516821 A | 6/2019 | |
| JP | 2021518410 A | 8/2021 | |
| JP | 7069033 B2 | 5/2022 | |
| KR | 20030032939 A | 4/2003 | |
| KR | 20100138910 A | 12/2010 | |
| KR | 101041446 B1 | 6/2011 | |
| KR | 10-2015-0007795 A | 1/2015 | |
| KR | 20160022358 A | 2/2016 | |
| KR | 20180005650 A | 1/2018 | |
| KR | 10-2020-0133374 A | 11/2020 | |
| KR | 20210032434 A | 3/2021 | |
| KR | 102530707 B1 | 5/2023 | |
| SU | 1121931 A1 | 4/1988 | |
| WO | WO 9502700 A1 | 1/1995 | |
| WO | WO 9506731 A2 | 3/1995 | |
| WO | WO 9832463 A2 | 7/1998 | |
| WO | WO 0173123 A2 | 10/2001 | |
| WO | WO-0183502 A1 | 11/2001 | |
| WO | WO-01083502 A1 | 11/2001 | |
| WO | WO 0222883 A1 | 3/2002 | |
| WO | WO 02083954 A1 | 10/2002 | |
| WO | WO 2004007751 A2 | 1/2004 | |
| WO | WO 2007094135 A1 | 8/2007 | |
| WO | WO 2009113645 A1 | 9/2009 | |
| WO | WO 2010026957 A1 | 3/2010 | |
| WO | 2011088193 A2 | 7/2011 | |
| WO | WO 2013012687 A2 | 1/2013 | |
| WO | WO 2014102803 A1 | 7/2014 | |
| WO | WO 2014147642 A1 | 9/2014 | |
| WO | WO 2015027176 A1 * | 2/2015 | C07F 9/064 |
| WO | WO 2015091953 A1 | 6/2015 | |
| WO | WO 2015155753 A2 | 10/2015 | |
| WO | 2016168750 A1 | 10/2016 | |
| WO | WO 2016183185 A1 * | 11/2016 | C09B 69/101 |
| WO | WO 2017003639 A2 | 1/2017 | |
| WO | WO 2017062271 A2 | 4/2017 | |
| WO | WO 2017089890 A1 | 6/2017 | |
| WO | WO 2017094897 A1 | 6/2017 | |
| WO | WO-2017173355 A1 | 10/2017 | |
| WO | WO-2017177065 A2 | 10/2017 | |
| WO | WO 2017197144 A1 | 11/2017 | |
| WO | WO 2018045278 A1 | 3/2018 | |
| WO | 2019071208 A1 | 4/2019 | |
| WO | WO 2019126691 A1 | 6/2019 | |
| WO | WO 2019140227 A1 | 7/2019 | |
| WO | WO 2019182765 A1 | 9/2019 | |
| WO | WO 2019182766 A1 | 9/2019 | |
| WO | 2020014634 A1 | 1/2020 | |
| WO | WO 2020219959 A1 | 10/2020 | |
| WO | 2021062176 A2 | 4/2021 | |
| WO | 2022125564 A1 | 6/2022 | |

OTHER PUBLICATIONS

Arian et al., "1,9-Dialkoxyanthracene as a 1O2-Sensitive Linker," *J. Am. Chem. Soc.* 133:3972-3980, 2011.

Aviñó et al., "Solid-phase synthesis of oligomers carrying several chromophore units linked by phosphodiester backbones," *Bioorganic & Medicinal Chemistry Letters* 18:2306-2310, 2008.

Avirah et al., "Infrared Absorbing Croconaine Dyes: Synthesis and Metal Ion Binding Properties," *J. Org. Chem.* 73(1):274-279, 2008.

Babitskaya et al., "Bromoacyl Analogues of Phosphatidycholine with Intramolecular Fluorescence Quenching and Their Use as Substrates for Continuous Monitoring of Phospholipase A2 Activity," *Applied Biochemistry and Microbiology* 40(4):351-356, 2004.

(56) References Cited

OTHER PUBLICATIONS

Bag et al., "Triazolyl-donor-acceptor chromophore-decorated unnatural amino acids and peptides: FRET events in a β-turn conformation," *Chem. Commun.* 50:433-435, 2014.

Bargh et al., "Cleavable linkers in antibody-drug conjugates," *Chemical Society Reviews* 48(16):4361-4374, Aug. 21, 2019. (15 pages).

Beaucage et al., "The Functionalization of Oligonucleotides Via Phosphoramidite Derivatives," *Tetrahedron* 49(10):1925-1963, 1993.

Becker et al., "New Thermotropic Dyes Based on Amino-Substituted Perylendicarboximides," *Chem. Eur. J.* 6(21):3984-3990, 2000.

Bergstrom et al., "A novel, highly potent HER2-targeted antibody-drug conjugate (ADC) for the treatment of low HER2-expressing tumors and combination with trastuzumab-based regimens in HER2-driven tumors," Mersana Therapeutics, Abstract LBA-231, 2015.

Bergstrom et al., "XMT-1522 induces tumor regressions in pre-clinical models representing HER2-positive and HER2 low-expressing breast cancer," Mersana Therapeutics, Abstract P4-14-28, 2015, 1 page.

Bergstrom et al., "A NaPi2b Antibody-Drug Conjugate Induces Durable Complete Tumor Regressions in Patient-Derived Xenograft Models of Nsclc," *IASLC 17th World Conference on Lung Cancer*, Vienna, Austria, Dec. 4-7, 2016 (8 pages).

Bergstrom et al., "Potent Promise," *Innovations in Pharmaceutical Technology* 49:16-20, 2014.

Boldyrev et al., "Synthesis and Characteristics of New Fluorescent Probes Based on Cardiolipin," *Russian Journal of Bioorganic Chemistry* 35(2):219-224, 2009.

Braeckmans et al., "Three-dimensional fluorescence recovery after photobleaching with the confocal scanning laser microscope," *Biophysical Journal* 85:2240-2252, 2003.

Braga et al., "Intracellular macromolecular mobility measured by fluorescence recovery after photobleaching with confocal laser scanning microscopes," *Molecular Biology of the Cell* 15:4749-4760, 2004.

Breul et al., "Fluorescent monomers as building blocks for dye labeled polymers: synthesis and application in energy conversion, biolabeling and sensors," Chem. Soc. Rev. 42(12):5366-5407, 2013.

Brinkley, "A brief survey of methods for preparing protein conjugates with dyes, haptens, and cross-linking reagents," *Bioconjugate Chem* 3:2-13, 1992.

Buckhout-White et al., "Assembling programmable FRET-based photonic networks using designer DNA scaffolds," *Nature Communications* 5:5615, Dec. 11, 2014. (16 pages).

CAPLUS Accession No. 1975: 171341, Holy, "Nucleic acid components and their analogs. CLXXII. Aliphatic analogs of nucleosides, nucleotides, and oligonucleotides," *Collection of Czechoslovak Chemical Communications* 40(1):187-214, 1975. (1 page).

CAPLUS Accession No. 1991:467753, Mielewczyk et al., "5' end fluorescent labelling of oligonucleotides with riboflavin-derived phosphitylating reagent," *Acta Biochimica Polonica* 36(3-4):225-233, 1989. (1 page).

CAPLUS Accession No. 1995:665426, Chen et al., "Synthesis of Novel Phosphoramidite Reagents for the Attachment of Antisense Oligonucleotides to Various Regions of the Benzophenanthridine Ring System," *Bioconjugate Chemistry* 6(4):473-482, Jul. 1, 1995. (1 page).

CAPLUS Accession No. 1995:733249, WO9506731A2, filed Mar. 9, 1995. (1 page).

CAPLUS Accession No. 1995:849926, Reed et al., "Structure-Activity Relationships of Cytotoxic Cholesterol-Modified DNA Duplexes," *Journal of Medicinal Chemistry* 38(22):4587-4596, Oct. 27, 1995. (1 page).

CAPLUS Accession No. 1997:497709, Puri et al., "Synthesis of 5'-polyarene-tethered oligo-DNAs and the thermal stability and spectroscopic properties of their duplexes and triplexes," *Tetrahedron* 53(30):10409-10432, Jul. 28, 1997. (1 page).

CAS Registry No. 862288-26-4, American Chemical Society, 2021. (1 page).

Chang et al., "A General Approach for Generating Fluorescent Probes to Visualize Piconewton Forces at the Cell Surface," *J. Am. Chem. Soc.* 138:2901-2904, 2016. (4 pages).

Chattopadhyay et al., "Brilliant Violet Fluorophores: A New Class of Ultrabright Fluorescent Compounds for Immunofluorescence Experiments," *Cytometry Part A* 81A:456-466, 2012.

Chen et al., "Synthesis and properties of new segmented block poly(urethane-urea)s containing phosphatidylcholine analogues and polybutadienes," *Macro-Molecular Chemistry and Physics* 197(5):1587-1597, May 1996. (11 pages).

Chen et al., "Synthesis of Novel Phosphoramidite Reagents for the Attachment of Antisense Oligonucleotides to Various Regions of the Benzophenanthridine Ring System," *Bioconjugate Chemistry* 6(4):473-482, Jul. 1, 1995. (10 pages).

Chong et al., "Oxygen Quenching of Pyrene-Lipid Fluorescence in Phosphatidylcholine Vesicles—A Probe for Membrane Organization," *Biophys. J.* 47:613-621, 1985.

Ciccotelli et al., "Polyguanine-conjugated antigens for scavenger receptor targeting and self-adjuvanting vaccines (VAC13P.1125)," *The Journal of Immunology* 194(Suppl. 1):214.5, May 1, 2015 [Abstract]. (1 page).

Cuppoletti et al., "Oligomeric fluorescent labels for DNA," *Bioconjug. Chem.* 16(3):528-534, 2005.

Dai et al., "DNA-polyfluorophore excimers as sensitive reporters for esterases and lipases," *Chem. Commun.* 46:1221-1223, 2010.

Damian et al., "Synthesis and DNA Interaction of Platinum Complex/Peptide Chimera as Potential Drug Candidates," *Eur. J. Org. Chem.* 6161-6170, 2010.

De Vos et al., "New Non Nucleosidic Phosphoramidites for the Solid Phase Multi-Labelling of Oligonucleotides: Comb- and Multifork-Like Structures," *Nucleosides & Nucleotides* 13(10):2245-2265, 1994.

Dioubankova et al., "Oligonucleotides containing new fluorescent 1-phenylethynylpyrene and 9,10-bis(phenylethynyl)anthracene uridine-2'-carbamates: synthesis and properties," *Tetrahedron* 60:4617-4626, 2004.

Divittorio et al., "Synthetic peptides with selective affinity for apoptotic cells," *Org. Biomol. Chem.* 4:1966-1976, 2006.

Doi et al., "Hetero-Selective DNA-Like Duplex Stabilized by Donor-Acceptor Interactions," *Chem. Eur. J.* 21:15974-15980, 2015.

Drescher et al., "General Synthesis and Aggregation Behaviour of New Single-Chain Bolaphospholipids: Variations in Chain and Headgroup Structures," *Chemistry—A European Journal* 14(22):6796-6804, 2008.

Dropulic et al., "Update on New Antivirals Under Development for the Treatment of Double-Stranded DNA Virus Infections," *Clinical Pharmacology & Therapeutics* 88(5):610-619, Nov. 2010.

Dubrovsky, "Semiconductor nanoparticles as reporters in multiplexed immunoassay and cell analysis," *International Journal of Nanoscience* 8(1 & 2):163-167, 2009.

Finniss et al., "A versatile acid-labile linker for antibody-drug conjugates," Med. Chem, Commun; 5; Apr. 1, 2014, 4 pages.

Franceschin et al., "Synthesis of a Dibromoperylene Phosphoramidite Building Block and Its Incorporation at the 5' End of a G-Quadruplex Forming Oligonucleotide: Spectroscopic Properties and Structural Studies of the Resulting Dibromoperylene Conjugate," *Bioconjugate Chem* 22:1309-1319, 2011.

Franzini et al., "Identification of Structure-Activity Relationships from Screening a Structurally Compact DNA-Encoded Chemical Library," *Angewandte Chemie International Edition* 54:3927-3931, Feb. 3, 2015 [with supporting information]. (41 pages).

Gao et al., "Libraries of Composite Polyfluors Built from Fluorescent Deoxyribosides," *Journal of the American Chemical Society* 124:11590-11591, 2002.

Gao et al., "Modified DNA Analogues That Sense Light Exposure with Color Changes," *Journal of the American Chemical Society* 126:12748-12749, 2004.

Gordon et al., "Analysis of simulated and experimental fluorescence recovery after photobleaching. Data for two diffusing components," *Biophysical Journal* 68:766-778, 1995.

Griesang et al., "Four-Color, Enzyme-Free Interrogation of DNA Sequences with Chemically Activated, 3'-Fluorphore-Labeled Nucleotides," *Angew. Chem. Int. Ed.* 45:6144-6148, 2006.

(56) References Cited

OTHER PUBLICATIONS

Gupta et al., "Dendrimers: Novel Polymeric Nanoarchitectures for Solubility Enhancement," *Biomacromolecules* 7(3):649-658, Mar. 2006 [Published online Feb. 15, 2006]. (10 pages).

Guryev et al., "Control of the Fluorescence of Dye-Antibody Conjugates by (2-Hydroxypropyl)-β-cyclodextrin in Fluorescence Microscopy and Flow Cytometry," *Analytical Chemistry* 83:7109-7114, Aug. 16, 2011.

Hanhela et al., "Synthesis and Evaluation of Fluorescent Materials for Colour Control of Peroxyoxalate Chemiluminescence. III. Yellow and Red Fluorescent Emitters," *Australian Journal of Chemistry* 34:1701-1717, 1981.

Haraguchi, "Live Cell Imaging: Approaches for Studying Protein Dynamics in Living Cells," *Cell Structure And Function* 27:333-334, 2002.

Hasegawa et al., "Cysteine, histidine and glycine exhibit antiinflammatory effects in human coronary arterial endothelial cells," *Clinical and Experimental Immunology* 167:269-274, Jan. 11, 2012. (6 pages).

Irani et al., "Molecular properties of human IgG subclasses and their implications for designing therapeutic monoclonal antibodies against infectious diseases," *Molecular Immunology* 67:171-182, 2015.

Jain et al. "Current ADC Linker Chemistry," *Pharm. Res.* 32:3526-3540, 2015.

Johansson, "Choosing Reporter-Quencher Pairs for Efficient Quenching Through Formation of Intramolecular Dimers," *Methods in Molecular Biology* 335:17-29, 2006.

Kashida et al., "A Cationic Dye Triplet as a Unique "Glue" That Can Connect Fully Matched Termini of DNA Duplexes," *Chem. Eur. J.* 17:2614-2622, 2011.

Khandare et al., "Polymer-drug conjugates: Progress in polymeric prodrugs," *Progress in Polymer Science* 31(4):359-397, Apr. 2006. (39 pages).

Kolpashchikov, "Binary Probes for Nucleic Acid Analysis," *Chemical Reviews* 110(8):4709-4723, Jun. 28, 2010. (15 pages).

Koo et al., "Fluorescent DNA chemosensors: identification of bacterial species by their volatile metabolites," *Chemical Communications* 47:11435-11437, 2011.

Kozma et al., "Fluorescent Ligands for Adenosine Receptors," *Bioorganic & Medicinal Chemistry Letters* 23: 26-36, 2013.

Kozytska et al., "Discovery of the novel, homogenous payload platform Dolasynthen for Antibody-Drug Conjugates," Mersana Therapeutics, Abstract #272, 2018. (1 page).

Krueger at al., "Fluorescent Amino Acids: Modular Building Blocks for the Assembly of New Tools for Chemical Biology," *ChemBioChem* 14:788-799, 2013.

Lapeyre et al., "Aryldithioethyloxycarbonyl (Ardec): A New Family of Amine Protecting Groups Removable under Mild Reducing Conditions and Their Applications to Peptide Synthesis," *Chem. Eur. J.* 12:3655-3671, 2006.

Lee et al., "Monitoring the Hydrophobic Interactions of Internally Pyrene-Labeled Poly(ethylene oxide)s in Water by Fluorescence Spectroscopy," *Macromolecules* 31:9193-9200, 1998.

Lee et al., "The spectroscopic analysis for binding of amphipathic and antimicrobial model peptides containing pyrenylalanine and tryptophan to lipid bilayer," *Biochimica et Biophysica Acta* 984:174-182, Sep. 4, 1989. (9 pages).

Leung et al., "7-Amino-4-Methyl-6-Sulfocoumarin-3-Acetic Acid: A Novel Blue Fluorescent Dye for Protein Labeling," *Bioorganic & Medicinal Chemistry Letters* 9: 2229-2232, 1999.

Lewis et al., "Orientation Control of Fluorescence Resonance Energy Transfer Using DNA as a Helical Scaffold," *J. Am. Chem. Soc.* 127(28):10002-10003, 2005.

Li et al., "Polymeric Drugs: Advances in the development of pharmacologically active polymers," *Journal of Controlled Release* 219:369-382, 2015.

Li et al., "Responsive nanogel-based dual fluorescent sensors for temperature and Hg2+ ions with enhanced detection sensitivity," *J. Mater. Chem.* 20:10716-10723, 2010.

Liso et al., "Polymeric drugs derived from Ibuprofen with improved antiinflammatory profile," *Journal of Biomedical Materials Research* 32:553-560, Dec. 1996. (8 pages).

Liu et al., "Detection of prostate-specific membrane antigen on HUVECs in response to breast tumor-conditioned medium," *International Journal of Oncology* 38:1349-1355, 2011.

Liu et al., "DNA-Based Micelles: Synthesis, Micellar Properties and Size-Dependent Cell Permeability," *Chem. Eur. J.*16:3791-3797, 2010 (14 Pages).

Liu et al., "Imidazole inhibits autophagy flux by blocking autophagic degradation and triggers apoptosis via increasing FoxO3a-Bim expression," *International Journal of Oncology* 46:721-731, Feb. 2015. (11 pages).

Liu et al., "Increased Cytotoxicity and Decreased In Vivo Toxicity of FdUMP[10] Relative to 5-FU," *Nucleosides & Nucleotides* 18(8):1789-1802, Aug. 1999. (14 pages).

Luo et al., "Sensitive and rapid quantification of C-reactive protein using quantum dot-labeled microplate immunoassay," *Journal of Translational Medicine* 10(24):1-9, 2012.

Lvnitski et al., "Introducing charge transfer functionality into prebiotically relevant β-sheet peptide fibrils," *Chemical Communications* 50:6733-6736, May 12, 2014. (4 pages).

Malakhov et al., "1-(Phenylethynyl)pyrene and 9,10-Bis(phenylethynyl)anthracene, Useful Fluorescent Dyes for DNA Labeling: Excimer Formation and Energy Transfer," *Eur. J. Org. Chem*: 1298-1307, 2004.

Marras et al., "Efficiencies of fluorescence resonance energy transfer and contact-mediated quenching in oligonucleotide probes," *Nucleic Acids Research* 30(21):e122, Nov. 1, 2002. (8 pages).

Masuko et al., "Fluorescence resonance energy transfer from pyrene to perylene labels for nucleic acid hybridization assays under homogenous solution conditions," *Nucleic Acids Research* 28(8):e34, 2000 (8 pages).

McKinlay et al., "Cell-Penetrating, Guanidinium-Rich Oligophosphoesters: Effective and Versatile Molecular Transporters for Drug and Probe Delivery," *J. Am. Chem. Soc.* 138:3510-3517, Feb. 22, 2016.

Mersana Therapeutics, URL= http://www.mersana.com, download date Jan. 3, 2019, 9 pages.

Midoux et al., "Chemical vectors for gene delivery: a current review on polymers, peptides and lipids containing histidine or imidazole as nucleic acids carriers," *British Journal of Pharmacology* 157:166-178, May 2009. (13 pages).

Mielewczyk et al., "5' end fluorescent labelling of oligonucleotides with riboflavin-derived phosphitylating reagent," *Acta Biochimica Polonica* 36(3-4):225-233, 1989. (9 pages).

Molotkovsky et al., "Perylenoyl- and Anthrylvinyl-Labeled Lipids as Membrane Probes," *Biochimica et Biophysica Acta* 778:281-288, 1984.

Moss, "Nomenclature of Fused and Bridged Fused Ring Systems," *Pure & Appl. Chem.* 70(1):143-216, 1998.

Mthembu et al., "Breaking a Couple: Disulfide Reducing Agents," *ChemBioChem* 21, 2020. (10 pages).

Nolting, "Linker Technology for Antibody-Drug Conjugates," in Ducry (ed.), *Antibody-Drug Conjugates*, Humana Press, Totowa, NJ, 2013, Ch. 5, pp. 71-100.

Nussbaumer et al., "Amplification of Chirality by Supramolecular Polymerization of Pyrene Oligomers," *Angewandte Chemie International Edition* 50:5490-5494, 2011.

Oh et al., "Low-dose guanidine and pyridostigmine: relatively safe and effective long-term symptomatic therapy in Lambert-Eaton myasthenic syndrome," *Muscle & Nerve* 20:1146-1152, Sep. 1997. (7 pages).

Paris et al., "Probing DNA sequences in solution with a monomer-excimer fluorescence color change," *Nucleic Acids Research* 26(16):3789-3793, 1998.

Pawelczyk et al., "Molecular Consortia-Various Structural and Synthetic Concepts for More Effective Therapeutics Synthesis," *International Journal of Molecular Sciences* 19:1104, Apr. 6, 2018. (19 pages).

Pelegrin et al., "Antiviral Monoclonal Antibodies: Can They Be More Than Simple Neutralizing Agents?" *Trends in Microbiology* 23(10):653-665, Oct. 2015.

(56) References Cited

OTHER PUBLICATIONS

Petersen et al., "Acyclic, achiral enamide nucleoside analogues. The importance of the C=C bond in the analogue for its ability to mimic natural nucleosides," *Organic & Biomolecular Chemistry* 1:3293-3296, Sep. 4, 2003. (4 pages).
Petreus et al., "Polyester imides containing main-chain phosphorus," *Revue Roumaine de Chimie* 34(8):971-978, 1994 (with English Abstract).
Phares et al., "Improving the Stability and Sensing of Electrochemical Biosensors by Employing Trithiol-Anchoring Groups in a Six-Carbon Self-Assembled Monolayer," *Anal. Chem.* 81(3):1095-1100, Feb. 1, 2009.
Poupart et al., "Aminopropargyl derivative of terpyridine-bis(methylenamine) tetraacetic acid chelate of europium (Eu (TMT)-AP3): a new reagent for fluorescent labelling of proteins and peptides," *Org. Biomol. Chem.* 4:4165-4177, Oct. 2006.
Pownall et al., "Kinetics of Spontaneous and Plasma-Stimulated Sphingomyelin Transfer," *iBiochimica et Biophysica Acta* 712:169-176, 1982.
PubChem, "US20100012929A1-20100121-C00010_4," SID No. 140452858, retrieved Mar. 29, 2016 from URL https://pubchem.ncbi.nlm.nih.gov/substance/140452858#sectio . . . , 6 pages.
Puri et al., "Synthesis of 5'-polyarene-tethered oligo-DNAs and the thermal stability and spectroscopic properties of their duplexes and triplexes," *Tetrahedron* 53(30):10409-10432, Jul. 28, 1997. (24 pages).
Reed et al., "Structure-Activity Relationships of Cytotoxic Cholesterol-Modified DNA Duplexes," *Journal of Medicinal Chemistry* 38(22):4587-4596, Oct. 27, 1995. (10 pages).
Ren et al., "An Antisense Oligodeoxynucleotide-Doxorubicin Conjugate: Preparation and Its Reversal Multidrug Resistance of Human Carcinoma Cell Line In Vitro," Nucleosides, Nucleotides & Nucleic Acids 23(10):1595-1607, 2004.
RN 230952-79-1, Registry Database Compound, 1999.
Rochat et al., "Water-Soluble Cationic Conjugated Polymers: Response to Electron-Rich Bioanalytes," *J. Am. Chem. Soc.* 135:17703-17706, 2013.
Rupcich et al., "Quenching of Fluorophore-Labeled DNA Oligonucleotides by Divalent Metal Ions: Implications for Selection, Design, and Applications of Signaling Aptamers and Signaling Deoxyribozymes," J. Am. Chem. Soc. 126(3):780-790, 2006.
Saito et al., "Dual-labeled oligonucleotide probe for sensing adenosine via FRET: A novel alternative to SNPs genotyping," Chem. Commun.:2133-2135, 2007.
Samal et al., "Cationic polymers and their therapeutic potential," *Chemical Society Reviews* 41:7147-7194, Aug. 2012. (48 pages).
Shuey et al., "Cyclohexanediol Bisphosphates as Models for Phospholipid-Metal Ion Binding Sites," *Bioorganic Chemistry* 21:95-108, Mar. 1993. (14 pages).
Shuman et al., "Bacterial DNA repair by non-homologous end joining," *Nature Reviews Microbiology* 5:852-861, Nov. 2007.
Singh et al., "Multiplexed measurement of membrane protein populations," *Caplus* 2003:769075, 2003. (2 pages).
Stewart et al., "The Fluorescence of a Chelating Two-Photon-Absorbing Dye is Enhanced with the Addition of Transition Metal Ions but Quenched in the Presence of Acid," *Proc. of SPIE* 9939:993904, 2016 (10 pages).
STIC Search Report from American Chemical Society, for U.S. Appl. No. 17/255,353, dated Sep. 7, 2023. (143 pages).
Striebel et al., "Enhancing sensitivity of human herpes virus diagnosis with DNA microarrays using dendrimers," *Experimental and Molecular Pathology* 77:89-97, Oct. 2004 [Published online Jul. 15, 2004]. (9 pages).
Stuart et al., "Site-Specific DNA-Doxorubicin Conjugates Display Enhanced Cytotoxicity to Breast Cancer Cells," *Bioconjugate Chemistry* 25:406-413, 2014.
Sun et al., "Dual-Color Fluorescence Imaging of Magnetic Nanoparticles in Live Cancer Cells Using Conjugated Polymer Probes," *Scientific Reports* 6:22368, 2016. (12 pages).

Sun et al., "High yield production of high molecular weight poly(ethylene glycol)/ a- cyclodextrin polyrotaxanes by aqueous one-pot approach," *Polymer* 53:2884-2889, 2012.
Sun et al., "Self-assembled biodegradable micellar nanoparticles of amphiphilic and cationic block copolymer for siRNA delivery," *Biomaterials* 29:4348-4355, available online Aug. 2008. (8 pages).
Sun et al., "Ultrabright and Multicolorful Fluorescence of Amphiphilic Polyethyleneimine Polymer Dots for Efficiently Combined Imaging and Therapy," *Scientific Reports* 3:3036, 2013. (6 pages).
Tabujew et al., "Chapter One: Functionalization of Cationic Polymers for Drug Delivery Applications," *RSC Polymer Chemistry Series* 13, 2015. (29 pages).
Takakusa et al., "Design and Synthesis of an Enzyme-Cleavable Sensor Molecule for Phosphodiesterase Activity Based on Fluorescence Resonance Energy Transfer," *J. Am. Chem. Soc.* 124(8):1653-1657, Feb. 2002.
Teo et al., "Polyfluorophores on a DNA Backbone: A Multicolor Set of Labels Excited at One Wavelength," *J. Am. Chem. Soc.* 131(11):3923-3933, 2009. (NIH Public Access Author Manuscript, available in PMC Mar. 25, 2010, 23 pages).
Teyssot et al., "Aromatic Nitrogen Donors for Efficient Copper(1)-NHC CuAAC under Reductant-Free Conditions," *Eur. J. Org. Chem.* 3507-3515, 2010.
Tram et al., "Oligonucleotide Labeling Using BODIPY Phosphoramidite," *Nucleosides, Nucleotides & Nucleic Acids* 30(1):1-11, 2011.
Vinogradov et al., "Total synthesis and biochemical characterization of mirror image barnase," *Chem Sci.* 6: 2997-3002, 2015.
Vybornyi et al., "Formation of Two-Dimensional Supramolecular Polymers by Amphiphilic Pyrene Oligomers," *Angew. Chem. Int. Ed.* 52:114488-11493, 2013.
Wang et al., "Cruciforms: Assembling Single Crystal Micro- and Nanostructures from One to Three Dimensions and Their Applications in Organic Field-Effect Transistors," *Chem. Mater.* 21:2840-2845, 2009.
Wang et al., "DNA Polyfluorophores for Real-Time Multicolor Tracking of Dynamic Biological Systems," *Angew. Chem. Int. Ed.* 51:7176-7180, 2012.
Wang et al., "Fluorescence-Based Evaluation of the Partitioning of Lipids and Lipidated Peptides into Liquid-Ordered Lipid Microdomains: A Model for Molecular Partitioning into Lipid Rafts," *Biophysical Journal* 79:919-933, Aug. 2000.
Wang et al., "Novel dexamethasone-HPMA copolymer conjugate and its potentialapplication in treatment of rheumatoid arthritis," *Arthritis Research & Therapy* 9(1):R2, Jan. 18, 2007. (9 pages).
Wang, "Modern Synthetic Methods and Technologies of Polymers," Common Knowledge Evidence, Tongji University Press, 1st Edition, Jul. 2013, pp. 210-211. (includes portion of Chinese Office Action with English Summary of relevance) (20 pages).
Wilson et al., "Efficient Quenching of Oligomeric Fluorophores on a DNA Backbone," *Journal of the American Chemical Society* 129(50):15426-15427, 2007.
Wilson et al., "Oligodeoxyfluorosides: Strong Sequence of Dependence of Fluorescence Emission," *Tetrahedron* 63(17):3427-3433, 2007 (18 Pages).
Winiger et al., "Long-Distance Electronic Energy Transfer in Light-Harvesting Supramolecular Polymers," *Angew. Chem. Int. Ed.* 53:13609-13613, 2014.
Wu Yi et al., "$^{Py}$A-Modified Oligodeoxyadenylates: Expanded Fluorescence Phenomena and Structural Formation," *Chemistry—An Asian Journal* 7:60-63, Nov. 2011. (4 pages).
Xu et al., "Synthesis of [D-Pyrenylalanine4,4']gramicidin S by Solid-Phase-Synthesis and Cyclization-Cleavage Method with Oxime Resin," *Chemistry Letters* 21:191-194, Feb. 1992. (4 pages).
Yu et al., "Targeted Delivery of an Anti-Inflammatory PDE4 Inhibitor to Immune Cells via an Antibody-drug Conjugate," *Molecular Therapy* 24(12):2078-2089, Dec. 2016.
Yurkovetskiy et al., "Advantages of Polyacetal Polymer-based Antibody Drug Conjugates: Application to Low Expression Targets," Mersana Therapeutics, technical paper #2645, 2014, 1 page.
Zhang et al., "FRET Imaging of Enzyme-Responsive HPMA Copolymer Conjugate," *Macromol. Biosci.* 17:1600125, 2017 (8 pages).

(56) References Cited

OTHER PUBLICATIONS

Zhao et al., "Mussel-Inspired One-Pot Synthesis of a Fluorescent and Water-SolublePolydopamine-Polyethyleneimine Copolymer," Macromol. Rapid Commun. 36:909-915, 2015.
U.S. Appl. No. 18/438,105, filed Feb. 9, 2024.
U.S. Appl. No. 18/570,283, filed Dec. 14, 2023.
U.S. Appl. No. 18/632,909, filed Apr. 11, 2024.
U.S. Appl. No. 18/290,630, filed Jan. 19, 2024.
U.S. Appl. No. 18/695,618, filed Mar. 26, 2024.
U.S. Appl. No. 18/695,674, filed Mar. 26, 2024.
U.S. Appl. No. 18/618,544, filed Mar. 27, 2024.

\* cited by examiner

POLYMERIC DYES WITH LINKER GROUPS COMPRISING DEOXYRIBOSE

BACKGROUND

Field

The present disclosure is generally directed to polymeric fluorescent or colored dyes having deoxyribose linker groups, and methods for their preparation and use in various analytical methods.

Description of the Related Art

Fluorescent and/or colored dyes are known to be particularly suitable for applications in which a highly sensitive detection reagent is desirable. Dyes that are able to preferentially label a specific ingredient or component in a sample enable the researcher to determine the presence, quantity and/or location of that specific ingredient or component. In addition, specific systems can be monitored with respect to their spatial and temporal distribution in diverse environments.

Fluorescence and colorimetric methods are extremely widespread in chemistry and biology. These methods give useful information on the presence, structure, distance, orientation, complexation and/or location for biomolecules. In addition, time-resolved methods are increasingly used in measurements of dynamics and kinetics. As a result, many strategies for fluorescence or color labeling of biomolecules, such as nucleic acids and protein, have been developed. Since analysis of biomolecules typically occurs in an aqueous environment, the focus has been on development and use of water soluble dyes.

Highly fluorescent or colored dyes are desirable since use of such dyes increases the signal to noise ratio and provides other related benefits. Accordingly, attempts have been made to increase the signal from known fluorescent and/or colored moieties. For example, dimeric and polymeric compounds comprising two or more fluorescent and/or colored moieties have been prepared in anticipation that such compounds would result in brighter dyes. However, as a result of intramolecular fluorescence quenching, the known dimeric and polymeric dyes have not achieved the desired increase in brightness.

There is thus a need in the art for dyes having an increased molar brightness. Ideally, such dyes and biomarkers should be intensely colored or fluorescent and should be available in a variety of colors and fluorescent wavelengths. The present disclosure fulfills this need and provides further related advantages.

BRIEF SUMMARY

In brief, embodiments of the present disclosure are generally directed to compounds useful as water soluble, fluorescent and/or colored dyes and/or probes that enable visual detection of analyte molecules, such as biomolecules, as well as reagents for their preparation. Methods for visually detecting analyte molecules using the dyes are also described.

Embodiments of the presently disclosed dyes include two or more fluorescent and/or colored moieties covalently linked by linkers (e.g., "$L^2$", "$L^3$", "$L^4$", "$L^5$" and "$L^6$"). In contrast to previous reports of dimeric and/or polymeric dyes, the present dyes are significantly brighter than the corresponding monomeric dye compound. While, not wishing to be bound by theory, it is believed that the linker moiety provides sufficient spatial separation between the fluorescent and/or colored moieties such that intramolecular fluorescence quenching is reduced and/or eliminated.

The water soluble, fluorescent or colored dyes of embodiments of the disclosure are intensely colored and/or fluorescent and can be readily observed by visual inspection or other means. In some embodiments the compounds may be observed without prior illumination or chemical or enzymatic activation. By appropriate selection of the dye, as described herein, visually detectable analyte molecules of a variety of colors may be obtained.

In one embodiment, compounds having the following structure (I) are provided:

$$\left( \left[ \begin{matrix} M^2 \\ | \\ L^7 \\ | \\ L^6-R^3-L^5 \end{matrix} \right]_q \left[ O-\overset{R^5}{\underset{R^4}{\overset{|}{P}}}-L^4-O-\overset{R^5}{\underset{R^4}{\overset{|}{P}}}-O-L^3 \right]_m \left[ \begin{matrix} M^1 \\ | \\ L^{1b} \\ | \\ L^{1a} \\ O \\ | \\ L^2 \end{matrix} \right]_w \right)_n R^1 \quad (I)$$

or a stereoisomer, tautomer, or salt thereof, wherein $R^1$, $R^2$, $R^3$, $R^4$, $R^5$, $L^{1a}$, $L^{1b}$, $L^2$, $L^3$, $L^4$, $L^5$, $L^6$, $L^7$, $M^1$, $M^2$, q, w, m and n are as defined herein. Compounds of structure (I) find utility in a number of applications, including use as fluorescent and/or colored dyes in various analytical methods.

In another embodiment, a method for staining a sample is provided, the method comprises adding to said sample a compound of structure (I) in an amount sufficient to produce an optical response when said sample is illuminated at an appropriate wavelength.

In still other embodiments, the present disclosure provides a method for visually detecting an analyte molecule, comprising:
 (a) providing a compound of structure (I); and
 (b) detecting the compound by its visible properties.

Other disclosed methods include a method for visually detecting a biomolecule, the method comprising:
 (a) admixing a compound of structure (I) with one or more biomolecules; and
 (b) detecting the compound by its visible properties.

Other embodiments provide a method for visually detecting an analyte, the method comprising:
 (a) providing a compound as disclosed herein, wherein $R^1$ or $R^2$ comprises a linker comprising a covalent bond to a targeting moiety having specificity for the analyte;
 (b) admixing the compound and the analyte, thereby associating the targeting moiety and the analyte; and
 (c) detecting the compound by its visible properties.

Other embodiments are directed to a composition comprising a compound of structure (I) and one or more analyte molecule, such as a biomolecule. Use of such compositions in analytical methods for detection of the one or more biomolecules is also provided.

These and other aspects of the disclosure will be apparent upon reference to the following detailed description.

BRIEF DESCRIPTION OF THE DRAWINGS

In the figures, identical reference numbers identify similar elements. The sizes and relative positions of elements in the figures are not necessarily drawn to scale and some of these elements are enlarged and positioned to improve figure legibility. Further, the particular shapes of the elements as drawn are not intended to convey any information regarding the actual shape of the particular elements, and have been solely selected for ease of recognition in the figures.

DETAILED DESCRIPTION

Figure 1:
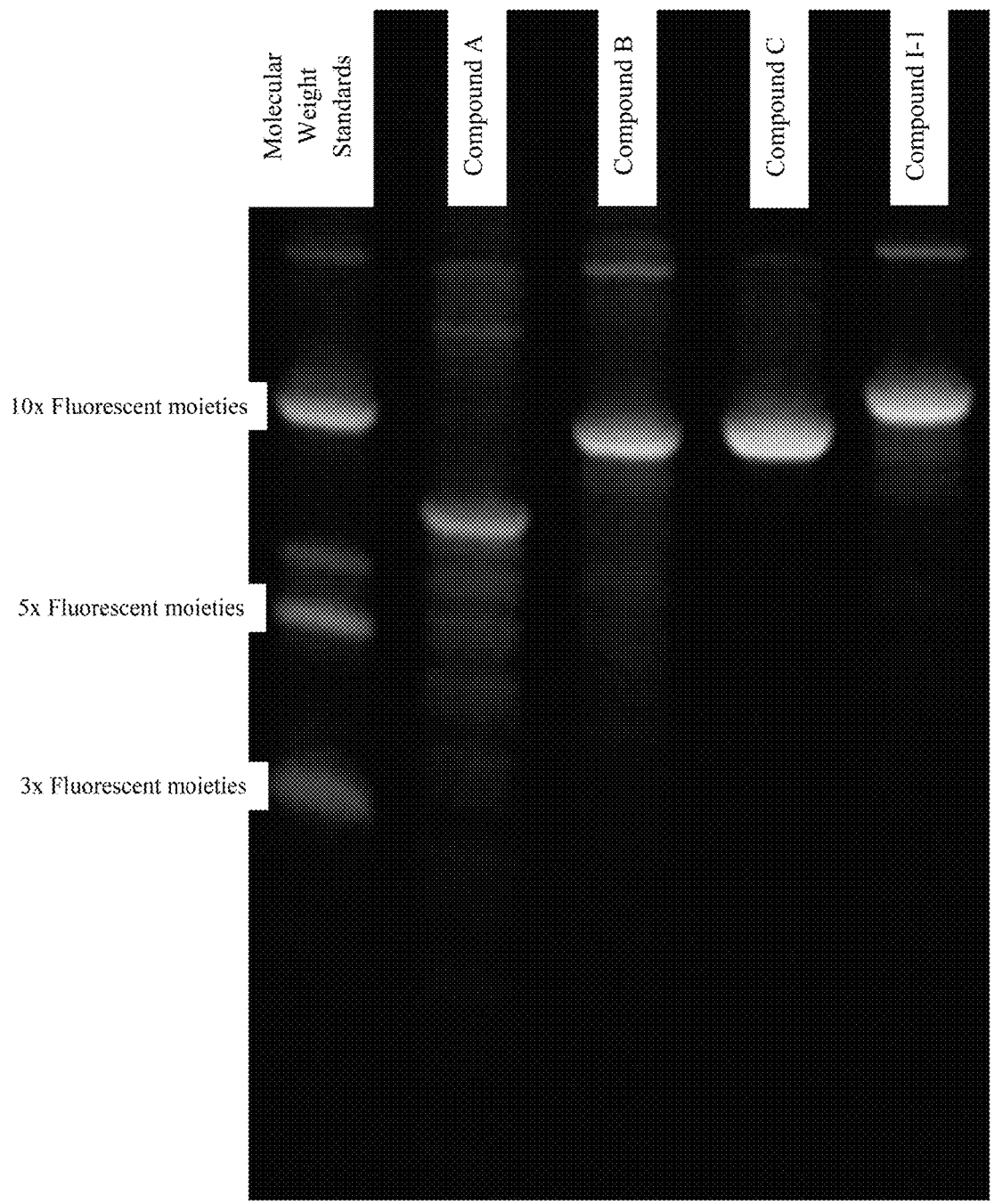
FIG. 1 shows a PAGE gel of Compound I-1 and comparative compounds

In the following description, certain specific details are set forth in order to provide a thorough understanding of various embodiments of the disclosure. However, one skilled in the art will understand that the disclosure may be practiced without these details.

Unless the context requires otherwise, throughout the present specification and claims, the word "comprise" and variations thereof, such as, "comprises" and "comprising" are to be construed in an open, inclusive sense, that is, as "including, but not limited to".

Reference throughout this specification to "one embodiment" or "an embodiment" means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ group.
"Carboxy" refers to the —$CO_2H$ group.
"Cyano" refers to the —CN group.
"Formyl" refers to the —C(=O)H group.
"Hydroxy" or "hydroxyl" refers to the —OH group.
"Imino" refers to the =NH group.
"Nitro" refers to the —$NO_2$ group.
"Oxo" refers to the =O substituent group.
"Sulfhydryl" refers to the —SH group.
"Thioxo" refers to the =S group.

"Alkyl" refers to a straight or branched hydrocarbon chain group consisting solely of carbon and hydrogen atoms, containing no unsaturation, having from one to twelve carbon atoms ($C_1$-$C_{12}$ alkyl), one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, alkyl groups are optionally substituted.

"Alkylene" or "alkylene chain" refers to a straight or branched divalent hydrocarbon chain linking the rest of the molecule to a radical group, consisting solely of carbon and hydrogen, containing no unsaturation, and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, alkylene is optionally substituted.

"Alkenylene" or "alkenylene chain" refers to a straight or branched divalent hydrocarbon chain linking the rest of the molecule to a radical group, consisting solely of carbon and hydrogen, containing at least one carbon-carbon double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, alkenylene is optionally substituted.

"Alkynylene" or "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms, e.g., ethenylene, propenylene, n-butenylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, alkynylene is optionally substituted.

"Alkylether" refers to any alkyl group as defined above, wherein at least one carbon-carbon bond is replaced with a carbon-oxygen bond. The carbon-oxygen bond may be on the terminal end (as in an alkoxy group) or the carbon oxygen bond may be internal (i.e., C—O—C). Alkylethers include at least one carbon oxygen bond, but may include more than one. For example, polyethylene glycol (PEG) is included within the meaning of alkylether. Unless stated otherwise specifically in the specification, an alkylether group is optionally substituted. For example, in some embodiments an alkylether is substituted with an alcohol or —OP(=$R_a$)($R_b$)$R_c$, wherein each of $R_a$, $R_b$ and $R_c$ is as defined for compounds of structure (I).

"Alkoxy" refers to a group of the formula —$OR_a$ where $R_a$ is an alkyl group as defined above containing one to twelve carbon atoms. Unless stated otherwise specifically in the specification, an alkoxy group is optionally substituted.

"Alkoxyalkylether" refers to a group of the formula —$OR_aR_b$ where $R_a$ is an alkylene group as defined above containing one to twelve carbon atoms, and $R_b$ is an alkylether group as defined herein. Unless stated otherwise specifically in the specification, an alkoxyalkylether group is optionally substituted, for example substituted with an alcohol or —OP(=$R_a$)($R_b$)$R_c$, wherein each of $R_a$, $R_b$ and $R_c$ is as defined for compounds of structure (I).

"Heteroalkyl" refers to an alkyl group, as defined above, comprising at least one heteroatom (e.g., N, O, P or S) within the alkyl group or at a terminus of the alkyl group. In some embodiments, the heteroatom is within the alkyl group (i.e., the heteroalkyl comprises at least one carbon-[heteroatom]$_x$-carbon bond, where x is 1, 2 or 3). In other embodiments, the heteroatom is at a terminus of the alkyl group and thus serves to join the alkyl group to the remainder of the molecule (e.g., M1-H-A), where M1 is a portion of the molecule, H is a heteroatom and A is an alkyl group). Unless stated otherwise specifically in the specification, a heteroalkyl group is optionally substituted. Exemplary heteroalkyl groups include ethylene oxide (e.g., polyethylene oxide), optionally including phosphorous-oxygen bonds, such as phosphodiester bonds.

"Heteroalkoxy" refers to a group of the formula —OR$^a$ where R$^a$ is a heteroalkyl group as defined above containing one to twelve carbon atoms. Unless stated otherwise specifically in the specification, a heteroalkoxy group is optionally substituted.

"Heteroalkylene" refers to an alkylene group, as defined above, comprising at least one heteroatom (e.g., Si, N, O, P or S) within the alkylene chain or at a terminus of the alkylene chain. In some embodiments, the heteroatom is within the alkylene chain (i.e., the heteroalkylene comprises at least one carbon-[heteroatom]-carbon bond, where x is 1, 2 or 3). In other embodiments, the heteroatom is at a terminus of the alkylene and thus serves to join the alkylene to the remainder of the molecule (e.g., M1-H-A-M2, where M1 and M2 are portions of the molecule, H is a heteroatom and A is an alkylene). Unless stated otherwise specifically in the specification, a heteroalkylene group is optionally substituted. Exemplary heteroalkylene groups include ethylene oxide (e.g., polyethylene oxide) and the "C," "HEG," and "PEG 1K" linking groups illustrated below:

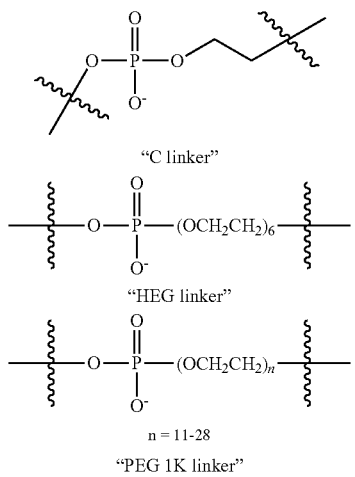

Multimers of the above C-linker, HEG linker and/or PEG 1K linker are included in various embodiments of heteroalkylene linkers. In some embodiments of the PEG 1K linker, n ranges from 19-25, for example n is 19, 20, 21, 22, 23, 24, or 25. Multimers may comprise, for example, the following structure:

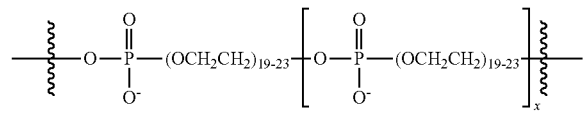

wherein x is 0 or an integer greater than 0, for example, x ranges from 0-100 (e.g., 1, 2, 3, 4, 5, 6, 7, 8, 9 or 10).

"Heteroalkenylene" is a heteroalkylene, as defined above, comprising at least one carbon-carbon double bond. Unless stated otherwise specifically in the specification, a heteroalkenylene group is optionally substituted.

"Heteroalkynylene" is a heteroalkylene comprising at least one carbon-carbon triple bond. Unless stated otherwise specifically in the specification, a heteroalkynylene group is optionally substituted.

"Heteroatomic" in reference to a "heteroatomic linker" refers to a linker group consisting of one or more heteroatoms. Exemplary heteroatomic linkers include single atoms selected from the group consisting of O, N, P and S, and multiple heteroatoms for example a linker having the formula —P(O—)(=O)O— or —OP(O—)(=0)O— and multimers and combinations thereof.

"Phosphate" refers to the —OP(=O)(R$_a$)R$_b$ group, wherein R$_a$ is OH, O— or OR$_c$; and R$_b$ is OH, O—, OR$_c$, a thiophosphate group or a further phosphate group, wherein R$_c$ is a counter ion (e.g., Na$^+$ and the like).

"Phosphoalkyl" refers to the —OP(=O)(R$_a$)R$_b$ group, wherein R$_a$ is OH, O— or OR$_c$; and R$_b$ is —Oalkyl, wherein R$_c$ is a counter ion (e.g., Na$^+$ and the like). Unless stated otherwise specifically in the specification, a phosphoalkyl group is optionally substituted. For example, in certain embodiments, the —Oalkyl moiety in a phosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Phosphoalkylether" refers to the —OP(=O)(R$_a$)R$_b$ group, wherein R$_a$ is OH, O— or OR$_c$; and R$_b$ is —Oalkylether, wherein R$_c$ is a counter ion (e.g., Na$^+$ and the like). Unless stated otherwise specifically in the specification, a phosphoalkylether group is optionally substituted. For example, in certain embodiments, the —Oalkylether moiety in a phosphoalkylether group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Thiophosphate" refers to the —OP(=R$_a$)(R$_b$)R$_c$ group, wherein R$_a$ is O or S, R$_b$ is OH, O—, S—, OR$_d$ or SR$_d$; and R$_c$ is OH, SH, O—, S—, OR$_d$, SR$_d$, a phosphate group or a further thiophosphate group, wherein R$_d$ is a counter ion (e.g., Na$^+$ and the like) and provided that: i) R$_a$ is S; ii) R$_b$ is S— or SR$_d$; iii) R$_c$ is SH, S— or SR$_d$; or iv) a combination of i), ii) and/or iii).

"Thiophosphoalkyl" refers to the —OP(=R$_a$)(R$_b$)R$_c$ group, wherein R$_a$ is O or S, R$_b$ is OH, O—, S—, OR$_d$ or SR$_d$; and R$_c$ is —Oalkyl, wherein R$_d$ is a counter ion (e.g., Na$^+$ and the like) and provided that: i) R$_a$ is S; ii) R$_b$ is S— or SR$_d$; or iii) R$_a$ is S and R$_b$ is S— or SR$_d$. Unless stated otherwise specifically in the specification, a thiophosphoalkyl group is optionally substituted. For example, in certain embodiments, the —Oalkyl moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Thiophosphoalkylether" refers to the —OP(=R$_a$)(R$_b$)R$_c$ group, wherein R$_a$ is O or S, R$_b$ is OH, O—, S—, OR$_d$ or SR$_d$; and R$_c$ is —Oalkylether, wherein R$_d$ is a counter ion (e.g., Na$^+$ and the like) and provided that: i) R$_a$ is S; ii) R$_b$ is S— or SR$_d$; or iii) R$_a$ is S and R$_b$ is S— or SR$_d$. Unless stated otherwise specifically in the specification, a thiophosphoalkylether group is optionally substituted. For example, in certain embodiments, the —Oalkylether moiety in a thiophosphoalkyl group is optionally substituted with one or more of hydroxyl, amino, sulfhydryl, phosphate, thiophosphate, phosphoalkyl, thiophosphoalkyl, phosphoalkylether, thiophosphoalkylether or —OP(=R$_a$)(R$_b$)R$_c$, wherein each of R$_a$, R$_b$ and R$_c$ is as defined for compounds of structure (I).

"Carbocyclic" refers to a stable 3- to 18-membered aromatic or non-aromatic ring comprising 3 to 18 carbon atoms. Unless stated otherwise specifically in the specification, a carbocyclic ring may be a monocyclic, bicyclic, tricyclic or tetracyclic ring system, which may include fused or bridged ring systems, and may be partially or fully saturated. Non-aromatic carbocyclyl radicals include cycloalkyl, while aromatic carbocyclyl radicals include aryl. Unless stated otherwise specifically in the specification, a carbocyclic group is optionally substituted.

"Cycloalkyl" refers to a stable non-aromatic monocyclic or polycyclic carbocyclic ring, which may include fused or bridged ring systems, having from three to fifteen carbon atoms, preferably having from three to ten carbon atoms, and which is saturated or unsaturated and attached to the rest of the molecule by a single bond. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, 7,7-dimethyl-bicyclo-[2.2.1]heptanyl, and the like. Unless stated otherwise specifically in the specification, a cycloalkyl group is optionally substituted.

"Aryl" refers to a ring system comprising at least one carbocyclic aromatic ring. In some embodiments, an aryl comprises from 6 to 18 carbon atoms. The aryl ring may be a monocyclic, bicyclic, tricyclic or tetracyclic ring system, which may include fused or bridged ring systems. Aryls include, but are not limited to, aryls derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group is optionally substituted.

"Heterocyclic" refers to a stable 3- to 18-membered aromatic or non-aromatic ring comprising one to twelve carbon atoms and from one to six heteroatoms selected from the group consisting of nitrogen, oxygen and sulfur. Unless stated otherwise specifically in the specification, the heterocyclic ring may be a monocyclic, bicyclic, tricyclic or tetracyclic ring system, which may include fused or bridged ring systems; and the nitrogen, carbon or sulfur atoms in the heterocyclic ring may be optionally oxidized; the nitrogen atom may be optionally quaternized; and the heterocyclic ring may be partially or fully saturated. Examples of aromatic heterocyclic rings are listed below in the definition of heteroaryls (i.e., heteroaryl being a subset of heterocyclic). Examples of non-aromatic heterocyclic rings include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, pyrazolopyrimidinyl, quinuclidinyl, thiazolidinyl, tetrahydrofuryl, trioxanyl, trithianyl, triazinanyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocyclic group is optionally substituted.

"Heteroaryl" refers to a 5- to 14-membered ring system comprising one to thirteen carbon atoms, one to six heteroatoms selected from the group consisting of nitrogen, oxygen and sulfur, and at least one aromatic ring. For purposes of certain embodiments of this disclosure, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, benzoxazolinonyl, benzimidazolthionyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, pteridinonyl, purinyl, pyrrolyl, pyrazolyl, pyridinyl, pyridinonyl, pyrazinyl, pyrimidinyl, pryrimidinonyl, pyridazinyl, pyrrolyl, pyrido[2,3-d]pyrimidinonyl, quinazolinyl, quinazolinonyl, quinoxalinyl, quinoxalinonyl, quinolinyl, isoquinolinyl, tetrahydroquinolinyl, thiazolyl, thiadiazolyl, thieno[3,2-d]pyrimidin-4-onyl, thieno[2,3-d]pyrimidin-4-onyl, triazolyl, tetrazolyl, triazinyl, and thiophenyl (i.e. thienyl). Unless stated otherwise specifically in the specification, a heteroaryl group is optionally substituted.

The suffix "-ene" refers to a particular structural feature (e.g., alkyl, aryl, heteroalkyl, heteroaryl) attached to the rest of the molecule through a single bond and attached to a radical group through a single bond. In other words, the suffix "-ene" refers to a linker having the structural features of the moiety to which it is attached. The points of attachment of the "-ene" chain to the rest of the molecule and to the radical group can be through one atom of or any two atoms within the chain. For example, a heteroarylene refers to a linker comprising a heteroaryl moiety as defined herein.

"Fused" refers to a ring system comprising at least two rings, wherein the two rings share at least one common ring atom, for example two common ring atoms. When the fused ring is a heterocyclyl ring or a heteroaryl ring, the common ring atom(s) may be carbon or nitrogen. Fused rings include bicyclic, tricyclic, tertracyclic, and the like.

The term "substituted" used herein means any of the above groups (e.g., alkyl, alkylene, alkenylene, alkynylene, heteroalkylene, heteroalkenylene, heteroalkynylene, alkoxy, alkylether, phosphoalkyl, phosphoalkylether, thiophosphoalkyl, thiophosphoalkylether, carbocyclic, cycloalkyl, aryl, heterocyclic and/or heteroaryl) wherein at least one hydrogen atom (e.g., 1, 2, 3 or all hydrogen atoms) is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted" also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

"Conjugation" refers to the overlap of one p-orbital with another p-orbital across an intervening sigma bond. Conjugation may occur in cyclic or acyclic compounds. A "degree of conjugation" refers to the overlap of at least one p-orbital with another p-orbital across an intervening sigma bond. For example, 1,3-butadine has one degree of conjugation, while benzene and other aromatic compounds typically have multiple degrees of conjugation. Fluorescent and colored compounds typically comprise at least one degree of conjugation.

"Fluorescent" refers to a molecule which is capable of absorbing light of a particular frequency and emitting light of a different frequency. Fluorescence is well-known to those of ordinary skill in the art.

"Colored" refers to a molecule which absorbs light within the colored spectrum (i.e., red, yellow, blue and the like).

A "linker" refers to a contiguous chain of at least one atom, such as carbon, oxygen, nitrogen, sulfur, phosphorous and combinations thereof, which connects a portion of a molecule to another portion of the same molecule or to a different molecule, moiety or solid support (e.g., microparticle). Linkers may connect the molecule via a covalent bond or other means, such as ionic or hydrogen bond interactions.

The term "biomolecule" refers to any of a variety of biological materials, including nucleic acids, carbohydrates, amino acids, polypeptides, glycoproteins, hormones, aptamers and mixtures thereof. More specifically, the term is intended to include, without limitation, RNA, DNA, oligonucleotides, modified or derivatized nucleotides, enzymes, receptors, prions, receptor ligands (including hormones), antibodies, antigens, and toxins, as well as bacteria, viruses, blood cells, and tissue cells. The visually detectable biomolecules of the disclosure (e.g., compounds of structure (I) having a biomolecule linked thereto) are prepared, as further described herein, by contacting a biomolecule with a compound having a reactive group that enables attachment of the biomolecule to the compound via any available atom or functional group, such as an amino, hydroxy, carboxyl, or sulfhydryl group on the biomolecule.

A "reactive group" is a moiety capable of reacting with a second reactive groups (e.g., a "complementary reactive group") to form one or more covalent bonds, for example by a displacement, oxidation, reduction, addition or cycloaddition reaction. Exemplary reactive groups are provided in Table 1, and include for example, nucleophiles, electrophiles, dienes, dienophiles, aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin, thiirane and the like.

"Bio-conjugation" or "bio-conjugate" and related variations refer to a chemical reaction strategy for forming a stable covalent bond between two molecules. The term "bio-conjugation" is generally used when one of the molecules is a biomolecule (e.g., an antibody), but can be used to describe forming a covalent bond with a non-biomolecule (e.g., a polymeric resin). The product or compound resulting from such a reaction strategy is a "conjugate," "bio-conjugate" or a grammatical equivalent.

The terms "visible" and "visually detectable" are used herein to refer to substances that are observable by visual inspection, without prior illumination, or chemical or enzymatic activation. Such visually detectable substances absorb and emit light in a region of the spectrum ranging from about 300 to about 900 nm. Preferably, such substances are intensely colored, preferably having a molar extinction coefficient of at least about 40,000, more preferably at least about 50,000, still more preferably at least about 60,000, yet still more preferably at least about 70,000, and most preferably at least about 80,000 M$^{-1}$ cm$^{-1}$. The compounds of the disclosure may be detected by observation with the naked eye, or with the aid of an optically based detection device, including, without limitation, absorption spectrophotometers, transmission light microscopes, digital cameras and scanners. Visually detectable substances are not limited to those which emit and/or absorb light in the visible spectrum. Substances which emit and/or absorb light in the ultraviolet (UV) region (about 10 nm to about 400 nm), infrared (IR) region (about 700 nm to about 1 mm), and substances emitting and/or absorbing in other regions of the electromagnetic spectrum are also included with the scope of "visually detectable" substances.

For purposes of embodiments of the disclosure, the term "photostable visible dye" refers to a chemical moiety that is visually detectable, as defined hereinabove, and is not significantly altered or decomposed upon exposure to light. Preferably, the photostable visible dye does not exhibit significant bleaching or decomposition after being exposed to light for at least one hour. More preferably, the visible dye is stable after exposure to light for at least 12 hours, still more preferably at least 24 hours, still yet more preferably at least one week, and most preferably at least one month. Non-limiting examples of photostable visible dyes suitable for use in the compounds and methods of the disclosure include azo dyes, thioindigo dyes, quinacridone pigments, dioxazine, phthalocyanine, perinone, diketopyrrolopyrrole, quinophthalone, and truarycarbonium.

As used herein, the term "perylene derivative" is intended to include any substituted perylene that is visually detectable. However, the term is not intended to include perylene itself. The terms "anthracene derivative", "naphthalene derivative", and "pyrene derivative" are used analogously. In some preferred embodiments, a derivative (e.g., perylene, pyrene, anthracene or naphthalene derivative) is an imide, bisimide or hydrazamimide derivative of perylene, anthracene, naphthalene, or pyrene.

The visually detectable molecules of various embodiments of the disclosure are useful for a wide variety of analytical applications, such as biochemical and biomedical applications, in which there is a need to determine the presence, location, or quantity of a particular analyte (e.g., biomolecule). In another aspect, therefore, the disclosure provides a method for visually detecting a biomolecule, comprising: (a) providing a biological system with a visually detectable biomolecule comprising the compound of structure (I) linked to a biomolecule; and (b) detecting the biomolecule by its visible properties. For purposes of the disclosure, the phrase "detecting the biomolecule by its visible properties" means that the biomolecule, without illumination or chemical or enzymatic activation, is observed with the naked eye, or with the aid of a optically based detection device, including, without limitation, absorption spectrophotometers, transmission light microscopes, digital cameras and scanners. A densitometer may be used to quantify the amount of visually detectable biomolecule present. For example, the relative quantity of the biomolecule in two samples can be determined by measuring relative optical density. If the stoichiometry of dye molecules per biomolecule is known, and the extinction coefficient of the dye molecule is known, then the absolute concentration of the biomolecule can also be determined from a measurement of optical density. As used herein, the term "biological system" is used to refer to any solution or mixture comprising one or more biomolecules in addition to the visually detectable biomolecule. Nonlimiting examples of such biological systems include cells, cell extracts, tissue samples, electrophoretic gels, assay mixtures, and hybridization reaction mixtures.

"Solid support" or "solid support residue" refers to any solid substrate known in the art for solid-phase support of molecules, for example a "microparticle" refers to any of a number of small particles useful for attachment to compounds of the disclosure, including, but not limited to, glass beads, magnetic beads, polymeric beads, non-polymeric beads, and the like. In certain embodiments, a microparticle comprises polystyrene beads.

A "targeting moiety" is a moiety that selectively binds or associates with a particular target, such as an analyte molecule. "Selectively" binding or associating means a targeting moiety preferentially associates or binds with the desired target relative to other targets. In some embodiments the compounds disclosed herein include linkages to targeting moieties for the purpose of selectively binding or associating the compound with an analyte of interest (i.e., the target of the targeting moiety), thus allowing detection of the analyte. Exemplary targeting moieties include, but are not limited to, antibodies, antigens, nucleic acid sequences, enzymes, proteins, cell surface receptor antagonists, and the like. In some embodiments, the targeting moiety is a moiety, such as an antibody, that selectively binds or associates with a target feature on or in a cell, for example a target feature on a cell membrane or other cellular structure, thus allowing for detection of cells of interest. Small molecules that selectively bind or associate with a desired analyte are also contemplated as targeting moieties in certain embodiments. One of skill in the art will understand other analytes, and the corresponding targeting moiety, that will be useful in various embodiments.

"Base pairing moiety" refers to a heterocyclic moiety capable of hybridizing with a complementary heterocyclic moiety via hydrogen bonds (e.g., Watson-Crick base pairing). Base pairing moieties include natural and unnatural bases. Non-limiting examples of base pairing moieties are RNA and DNA bases such adenosine, guanosine, thymidine, cytosine and uridine and analogues thereof.

Embodiments of the disclosure disclosed herein are also meant to encompass all compounds being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively.

Isotopically-labeled compounds of structure (I) can generally be prepared by conventional techniques known to those skilled in the art or by processes analogous to those described below and in the following Examples using an appropriate isotopically-labeled reagent in place of the non-labeled reagent previously employed.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event or circumstances may or may not occur, and that the description includes instances where said event or circumstance occurs and instances in which it does not. For example, "optionally substituted alkyl" means that the alkyl group may or may not be substituted and that the description includes both substituted alkyl groups and alkyl groups having no substitution.

"Salt" includes both acid and base addition salts.

"Acid addition salt" refers to those salts which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Base addition salt" refers to those salts which are prepared from addition of an inorganic base or an organic base to the free acid. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Crystallizations may produce a solvate of the compounds described herein. Embodiments of the present disclosure include all solvates of the described compounds. As used herein, the term "solvate" refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate and the like, as well as the corresponding solvated forms. The compounds of the disclosure may be true solvates, while in other cases the compounds of the disclosure may merely retain adventitious water or another solvent or be a mixture of water plus some adventitious solvent.

Embodiments of the compounds of the disclosure (e.g., compounds of structure I), or their salts, tautomers or solvates may contain one or more stereocenters and may thus give rise to enantiomers, diastereomers, and other stereoisomeric forms that may be defined, in terms of absolute stereochemistry, as (R)- or (S)- or, as (D)- or (L)- for amino acids. Embodiments of the present disclosure are meant to include all such possible isomers, as well as their racemic and optically pure forms. Optically active (+) and (−), (R)- and (S)-, or (D)- and (L)- isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

A "tautomer" refers to a proton shift from one atom of a molecule to another atom of the same molecule. The present disclosure includes tautomers of any said compounds. Various tautomeric forms of the compounds are easily derivable by those of ordinary skill in the art.

The chemical naming protocol and structure diagrams used herein are a modified form of the I.U.P.A.C. nomenclature system, using the ACD/Name Version 9.07 software program and/or ChemDraw Ultra Version 11.0 software naming program (CambridgeSoft). Common names familiar to one of ordinary skill in the art are also used.

As noted above, in one embodiment of the present disclosure, compounds useful as fluorescent and/or colored dyes in various analytical methods are provided. In other embodiments, compounds useful as synthetic intermediates for preparation of compounds useful as fluorescent and/or colored dyes are provided. In general terms, embodiments of the present disclosure are directed to dimers and higher polymers of fluorescent and/or colored moieties. The fluorescent and or colored moieties are linked by a linking moiety. Without wishing to be bound by theory, it is believed the linker helps to maintain sufficient spatial distance between the fluorescent and/or colored moieties such that intramolecular quenching is reduced or eliminated, thus resulting in a dye compound having a high molar "brightness" (e.g., high fluorescence emission).

Accordingly, in some embodiments the compounds have the following structure (A):

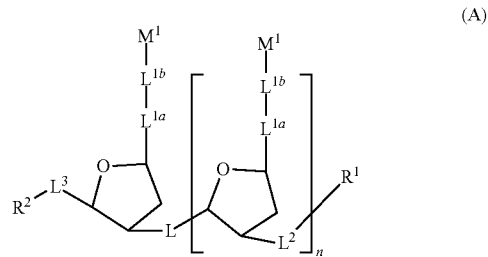

(A)

wherein L is a linker (e.g., heteroalkylene) sufficient to maintain spatial separation between one or more (e.g., each) $M^1$ group so that intramolecular quenching is reduced or eliminated, and $R^1$, $R^2$, $L^{1a}$, $L^{1b}$, $L^2$, $L^3$ and n are as defined for structure (I). In some embodiments of structure (A), L is a linker comprising one or more ethylene glycol or polyethylene glycol moieties.

In other embodiments is provided a compound having the following structure (I):

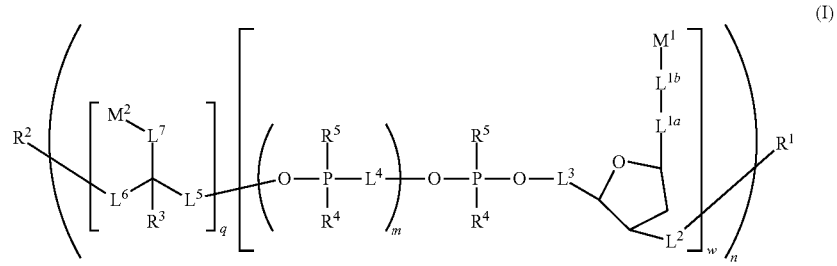

(I)

or a stereoisomer, salt or tautomer thereof, wherein:

$M^1$ and $M^2$ are, at each occurrence, independently a moiety comprising a chromophore;

$L^{1a}$ is, at each occurrence, independently a heteroarylene linker;

$L^{1b}$, $L^2$, $L^3$, $L^5$, $L^6$ and $L^7$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$R^1$ and $R^2$ are each independently H, OH, SH, alkyl, alkoxy, alkylether, heteroalkyl, —OP(=$R^a$)($R^b$)$R^c$, Q, or a protected form thereof, or L';

$R^3$ is, at each occurrence, independently H, alkyl or alkoxy;

$R^4$ is, at each occurrence, independently OH, SH, O⁻, S⁻, $OR_d$ or $SR_d$;

$R^5$ is, at each occurrence, independently oxo, thioxo or absent;

$R^a$ is O or S;

$R^b$ is OH, SH, O⁻, S⁻, $OR_d$ or $SR_d$;

$R_c$ is OH, SH, O⁻, S⁻, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, an integer of one or greater;

n is an integer of one or greater; and q and w are, at each occurrence, independently 0 or 1, provided at least one occurrence of w is 1.

The various linkers and substituents (e.g., $M^1$, $M^2$, Q, $R^1$, $R^2$, $R^3$, $R_c$, $L^{1a}$, $L^{1b}$, $L^2$, $L^3$, $L^4$, $L^5$, $L^6$ and $L^7$) in the compound of structure (I) are optionally substituted with one more substituent. For example, in some embodiments the optional substituent is selected to optimize the water solubility or other property of the compound of structure (I). In certain embodiments, each chromophore, alkyl, alkoxy, alkylether, heteroarylene, heteroalkyl, alkylene, alkenylene, alkynylene, heteroalkylene, heteroalkenylene, heteroalkynylene, alkoxyalkylether, phosphoalkyl, thiophosphoalkyl, phosphoalkylether and thiophosphoalkylether in the compound of structure (I) is optionally substituted with one more substituent selected from the group consisting of hydroxyl, alkoxy, alkylether, alkoxyalkylether, sulfhydryl, amino, alkylamino, carboxyl, phosphate, thiophosphate, phosphoalkyl, thiophosphoalkyl, phosphoalkylether and thiophosphoalkylether. In certain embodiments the optional substituent is —OP(=Ra)(Rb)Rc, where Ra, Rb and Rc are as defined for the compound of structure (I).

In some embodiments, at least one occurrence of $L^{1a}$ is an optionally substituted 5-7 membered heteroarylene linker. In some more specific embodiments, $L^{1a}$ is, at each occurrence independently an optionally substituted 5-7 membered heteroarylene linker. In some embodiments, $L^{1a}$ is a 6-membered heteroarylene. In some embodiments, $L^{1a}$ comprises two N atoms and two O atoms. In certain embodiments, $L^{1a}$ is, at each occurrence, substituted. In some related embodiments, $L^{1b}$ is substituted, for example, $L^{1b}$ is substituted with oxo, alkyl (e.g., methyl, ethyl, etc.) or combinations thereof. In more specific embodiments, $L^{1a}$ is, at each occurrence, substituted with at least one oxo. In some embodiments, $L^{1a}$ has one of the following structures:

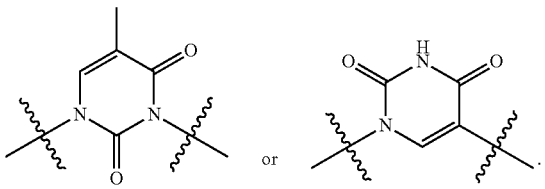 [SMILES: *n1cc(C)c(=O)n(*)c1=O ; *c1cn(*)c(=O)[nH]c1=O]

In some embodiments, $L^{1b}$ is, at each occurrence, independently an optional alkylene, alkenylene, alkynylene, heteroalkylene, heteroalkenylene, heteroalkynylene, alkyleneheteroarylenealkylene, alkyleneheterocyclylenealkylene, alkylenecarbocyclylenealkylene, heteroalkyleneheteroarylenealkylene, heteroalkyleneheterocyclylenealkylene, heteroalkylenecarbocyclylenealkylene, heteroalkyleneheteroarylenehetroalkylene, heteroalkyleneheterocyclyleneheteroalkylene, heteroalkylenecarbocyclyleneheteroalkylene, alkyleneheteroarylenehetroalkylene, alkyleneheterocyclyleneheteroalkylene, alkylenecarbocyclyleneheteroalkylene, heteroarylene, heterocyclylene, carbocyclylene, alkyleneheteroarylene, alkyleneheterocyclylene, heteroarylenealkylene, alkylenecarbocyclylene, carbocyclylenealkylene, heteroalkyleneheteroarylene, heteroalkyleneheterocyclylene, heteroaryleneheteroalkylene, heteroalkylenecarbocyclylene, carbocyclyleneheteroalkylene or heteroatomic linker. In some embodiments, $L^{1b}$ is an optionally substituted heteroalkenylene linker.

In some embodiments, at least one occurrence of $L^{1b}$ is substituted. In certain embodiments, $L^{1b}$ is substituted at each occurrence. In some more specific embodiments, $L^{1b}$ is substituted with oxo.

In other embodiments, $L^{1b}$ is at each occurrence, independently a linker comprising a functional group capable of formation by reaction of two complementary reactive groups (e.g., triazolyl, amide, etc.), for example a Q group.

The optional linkers $L^{1b}$ and $L^7$ can be used as a point of attachment of the $M^1$ and $M^2$ moieties to the remainder of the compound. For example, in some embodiments a synthetic precursor to the compound of structure (I) is prepared, and the $M^1$ and $M^2$ moieties are attached to the synthetic precursor using any number of facile methods known in the art, for example methods referred to as "click chemistry." For this purpose any reaction which is rapid and substantially irreversible can be used to attach $M^1$ and $M^2$ to the synthetic precursor to form a compound of structure (I). Exemplary reactions include the copper catalyzed reaction of an azide and alkyne to form a triazole (Huisgen 1,3-dipolar cycloaddition), reaction of a diene and dienophile (Diels-Alder), strain-promoted alkyne-nitrone cycloaddition, strain-promoted cycloalkyne-azide cycloaddition (Cu-free click), reaction of a strained alkene with an azide, tetrazine or tetrazole, alkene and azide[3+2]cycloaddition, alkene and tetrazine inverse-demand Diels-Alder, alkene and tetrazole photoreaction and various displacement reactions, such as displacement of a leaving group by nucleophilic attack on an electrophilic atom. Exemplary displacement reactions include reaction of an amine with: an activated ester; an N-hydroxysuccinimide ester; an isocyanate; an isothioscyanate or the like. In some embodiments the reaction to form $L^{1b}$ or $L^7$ may be performed in an aqueous environment.

Accordingly, in some embodiments $L^{1b}$ or $L^7$ are at each occurrence, independently a linker comprising a functional group capable of formation by reaction of two complementary reactive groups, for example a functional group which is the product of one of the foregoing "click" reactions. In various embodiments, for at least one occurrence of $L^{1b}$ or $L^7$, the functional group can be formed by reaction of an aldehyde, oxime, hydrazone, alkyne, amine, azide, acylazide, acylhalide, nitrile, nitrone, sulfhydryl, disulfide, sulfonyl halide, isothiocyanate, imidoester, activated ester (e.g., N-hydroxysuccinimide ester), ketone, α,β-unsaturated carbonyl, alkene, maleimide, α-haloimide, epoxide, aziridine, tetrazine, tetrazole, phosphine, biotin or thiirane functional group with a complementary reactive group, for example, via a reaction of an amine with an N-hydroxysuccinimide ester or isothiocyanate.

In other embodiments, for at least one occurrence of $L^{1b}$ or $L^7$, the functional group can be formed by reaction of an alkyne and an azide. In other embodiments, for at least one occurrence of $L^{1b}$ or $L^7$, the functional group can be formed by reaction of an amine (e.g., primary amine) and an N-hydroxysuccinimide ester or isothiocyanate.

In more embodiments, for at least one occurrence of $L^{1b}$ or $L^7$, the functional group comprises an alkene, ester, amide, thioester, disulfide, carbocyclic, heterocyclic or heteroaryl group. In more embodiments, for at least one occurrence of $L^{1b}$ or $L^7$, the functional group comprises an alkene, ester, amide, thioester, thiourea, disulfide, carbocyclic, heterocyclic or heteroaryl group. In other embodiments, the functional group comprises an amide or thiourea. In some more specific embodiments, for at least one occurrence of $L^{1b}$ or $L^7$, $L^{1b}$ or $L^7$ are linkers comprising a triazolyl functional group. In some related embodiments, $L^{1b}$ or $L^7$, at each occurrence, independently comprises a triazolyl functional group. While in other embodiments, for at least one occurrence of $L^{1b}$ or $L^7$ is a linker comprising an amide or thiourea functional group.

In still other embodiments, for at least one occurrence of $L^{1b}$, $L^{1b}\text{-}M^1$ has the following structure:

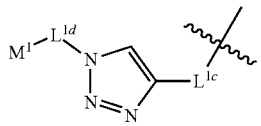

wherein $L^{1c}$ and $L^{1d}$ are each independently optional linkers.

In different embodiments, for at least one occurrence of $L^{1b}$, $L^{1b}\text{-}M^1$ has the following structure:

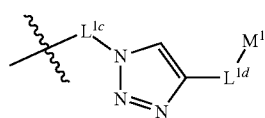

wherein $L^{1c}$ and $L^{1d}$ are each independently optional linkers.

In various embodiments of the foregoing, $L^{1c}$ or $L^{1d}$, or both, is absent. In other embodiments, $L^{1c}$ or $L^{1d}$, or both, is present.

In some embodiments $L^{1c}$ and $L^{1d}$, when present, are each independently alkylene or heteroalkylene. For example, in some embodiments $L^{1c}$ and $L^{1d}$, when present, independently have one of the following structures:

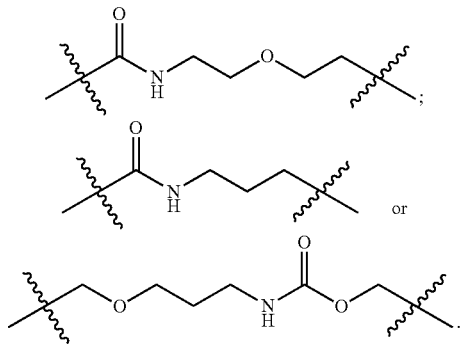

In still other embodiments, for at least one occurrence of $L^7$, $L^7\text{-}M^2$ has the following structure:

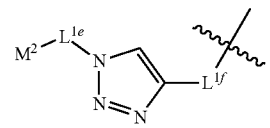

wherein $L^{1e}$ and $L^{1f}$ are each independently optional linkers.

In different embodiments, for at least one occurrence of $L^7$, $L^7\text{-}M^2$ has the following structure:

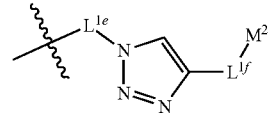

wherein $L^{1e}$ and $L^{1f}$ are each independently optional linkers.

In various embodiments of the foregoing, $L^{1e}$ or $L^{1f}$, or both, is absent. In other embodiments, $L^{1e}$ or $L^{1f}$, or both, is present.

In some embodiments $L^{1e}$ and $L^{1f}$, when present, are each independently alkylene or heteroalkylene. For example, in some embodiments $L^{1e}$ and $L^{1f}$, when present, independently have one of the following structures:

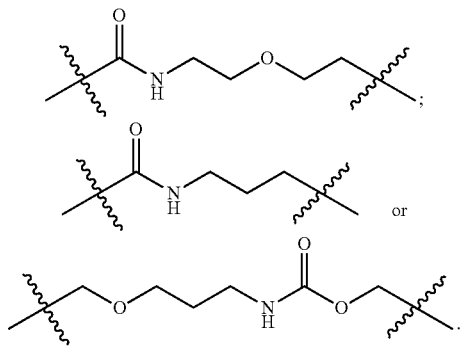

In some embodiments, at least one occurrence of $L^{1b}$ has one of the following structures:

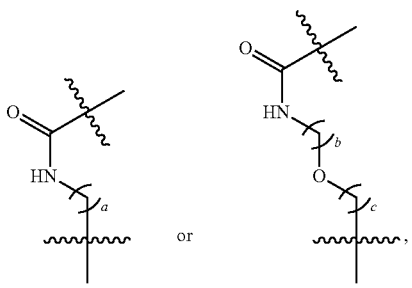

wherein
a, b, and c are each independently an integer ranging from 1-6.

In some embodiments, each occurrence of $L^{1b}$ has one of the following structures:

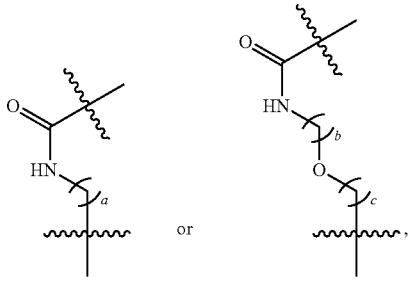

wherein
a, b, and c are each independently an integer ranging from 1-6.

In some embodiments, at least one occurrence of $L^{1b}$ has one of the following structures:

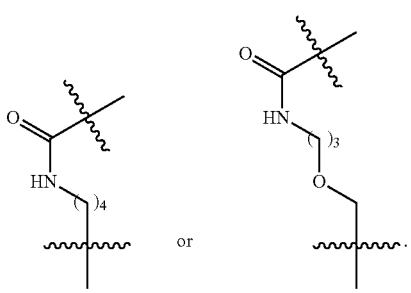

In still other different embodiments of structure (I), $L^{1b}$ is at each occurrence, independently an optional alkylene or heteroalkylene linker. In certain embodiments, $L^{1b}$ has one of the following structures:

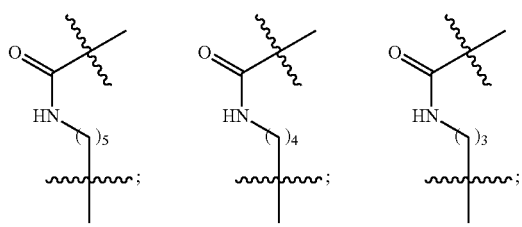

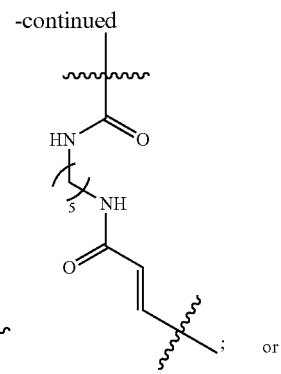

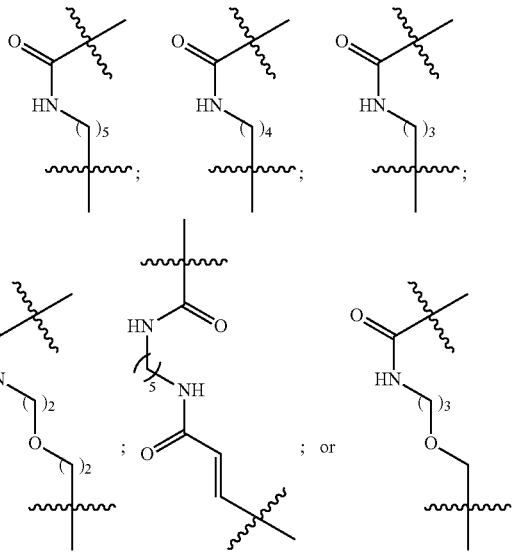

In still other different embodiments of structure (I), $L^7$ is at each occurrence, independently an optional alkylene or heteroalkylene linker. In certain embodiments, $L^7$ has one of the following structures:

In some embodiments, at least one occurrence of $L^3$ is an alkylene linker. In more specific embodiments, $L^3$ or is an alkylene linker at each occurrence. In certain embodiments, the alkylene linker is a methylene linker.

In some embodiments, at least one occurrence of $L^2$ is absent. In more specific embodiments, $L^2$ is absent at each occurrence.

In certain embodiments, at least one occurrence of $L^5$ or $L^6$ is a heteroalkylene linker. In some more specific embodiments, $L^5$ or $L^6$ is a heteroalkylene linker at each occurrence. In some embodiments, at least one occurrence of $L^4$ comprises alkylene oxide. In some embodiments, at least one occurrence of $L^5$ or $L^6$ comprises alkylene oxide. In some of the foregoing embodiments, the alkylene oxide is ethylene oxide, for example, polyethylene oxide. In certain embodiments, at least one occurrence of $L^5$ or $L^6$ is an alkylene linker (e.g., methylene). In some more specific embodiments, $L^5$ or $L^6$ is an alkylene linker at each occurrence (e.g., methylene).

In certain embodiments, at least one occurrence of $L^5$ is a heteroalkylene linker. In some more specific embodiments, $L^5$ is a heteroalkylene linker at each occurrence. In some embodiments, at least one occurrence of $L^5$ comprises alkylene oxide, for example, ethylene oxide (e.g., polyethylene oxide). In certain embodiments, at least one occurrence of $L^5$ is an alkylene linker (e.g., methylene). In some more specific embodiments, $L^5$ is an alkylene linker at each occurrence (e.g., methylene). In certain embodiments, at least one occurrence of $L^5$ is absent. In some more specific embodiments, $L^5$ is absent at each occurrence.

In certain embodiments, at least one occurrence of $L^6$ is a heteroalkylene linker. In some more specific embodiments, $L^6$ is a heteroalkylene linker at each occurrence. In some embodiments, at least one occurrence of $L^6$ comprises alkylene oxide. In some of the foregoing embodiments, the alkylene oxide is ethylene oxide, for example, polyethylene oxide. In certain embodiments, at least one occurrence of $L^6$ is an alkylene linker (e.g., methylene). In some more specific embodiments, $L^6$ is an alkylene linker at each occurrence (e.g., methylene). In certain embodiments, at least one occurrence of $L^6$ is absent. In some more specific embodiments, $L^6$ is absent at each occurrence.

In certain embodiments, at least one occurrence of $L^5$ or $L^6$ comprises a phosphodiester moiety. In more specific embodiments, each occurrence of $L^5$ or $L^6$ comprises a phosphodiester moiety. In more embodiments, $L^2$, $L^3$, $L^4$ or $L^6$ are, at each occurrence, independently $C_1$-$C_6$ alkylene, $C_2$-$C_6$ alkenylene or $C_2$-$C_6$ alkynylene.

In some embodiments, at least one occurrence of $L^5$ is heteroalkylene. In some embodiments, $L^5$ is heteroalkylene at each occurrence, for example, a heteroalkylene comprising one of the following structures:

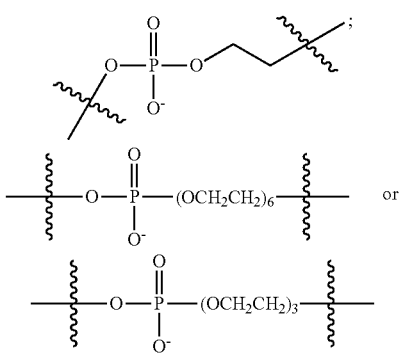

In some embodiments, at least one occurrence of $L^6$ is heteroalkylene. In some embodiments, $L^6$ is heteroalkylene at each occurrence, for example, a heteroalkylene comprising one of the following structures:

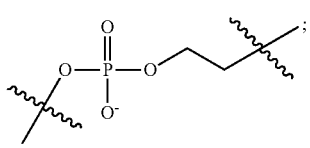

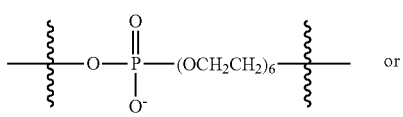

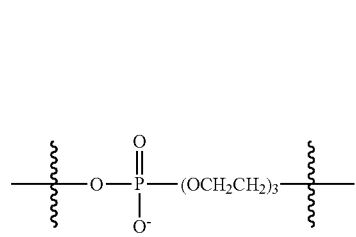

In some of the foregoing embodiments, a heteroalkylene (e.g., $L^3$, $L^4$, $L^5$ or $L^6$) comprises the following structure:

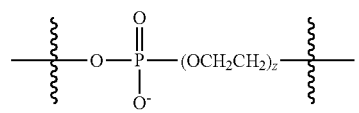

wherein z is an integer ranging from 19 to 30. In some embodiments, z ranges from 19-28. In certain embodiments, the average z is 23. In some embodiments, the average z is 19, 20, 21, 22, 23, 24, 25, 26, 27, or 28.

In some embodiments, at least one occurrence of $R^3$ is H. In more specific embodiments, $R^3$ is H at each occurrence.

In some embodiments, m is 0. In some of the foregoing embodiments, q is 0. In some related embodiments, the compound has the following structure (Ia):

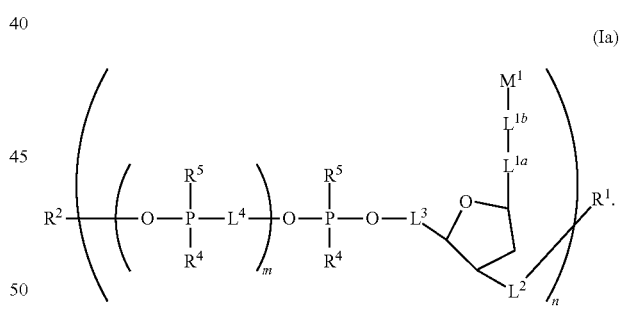

In some other embodiments, the compound has one of the following structures (Ib) or (Ic):

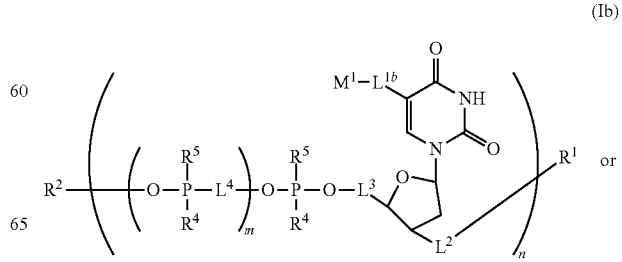

(Ic)

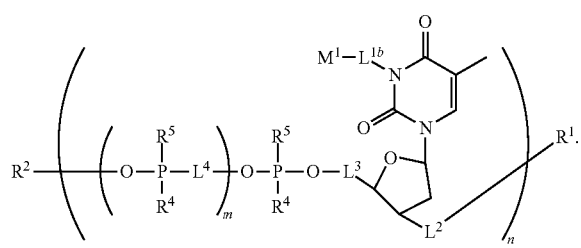

wherein:
  $L^{1b}$ is, at each occurrence, independently an optionally substituted alkylene or an optionally substituted heteroalkylene linker.

In some embodiments, the compound has one of the following structures (Id) or (Ie):

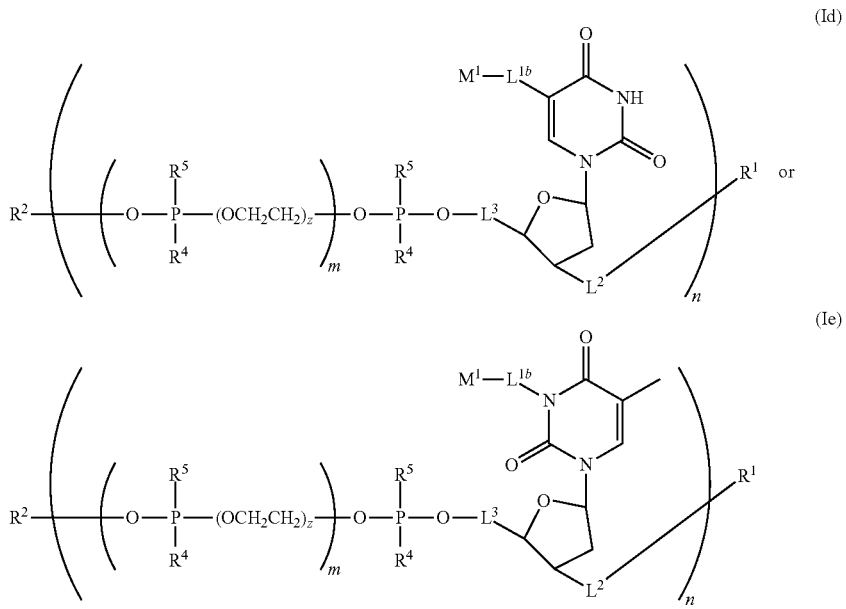

wherein:
  z is an integer from 1 to 100. In some embodiments, $L^{1b}$, at each occurrence, independently comprises an amide functional group or a triazolyl functional group.

In still other embodiments of any of the compounds of structure (I), $R^5$ is, at each occurrence, independently OH, $O^-$ or $OR_d$. It is understood that "$OR_d$" and "$SR_d$" are intended to refer to $O^-$ and $S^-$ associated with a cation. For example, the disodium salt of a phosphate group may be represented as:

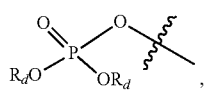

where $R_d$ is sodium ($Na^+$).

In other embodiments of any of the compounds of structure (I), at least one occurrence of $R^4$ is oxo. In other embodiments of any of the compounds of structure (I), $R^4$ is, at each occurrence, oxo.

In other various embodiments, $R^1$ and $R^2$ are each independently OH or $-OP(=R_a)(R_b)R_c$. In some different embodiments, $R^1$ or $R^2$ is OH or $-OP(=R_a)(R_b)R_c$, and the other of $R^1$ or $R^2$ is Q or a linker comprising a covalent bond to Q.

In still more different embodiments of any of the foregoing compounds of structure (I), $R^1$ and $R^2$ are each independently $-OP(=R_a)(R_b)R_c$. In some of these embodiments, $R_c$ is OL'.

In other embodiments, $R^1$ and $R^2$ are each independently $-OP(=R_a)(R_b)OL'$, and L' is an alkylene or heteroalkylene linker to: Q, a targeting moiety, an analyte (e.g., analyte molecule), a solid support, a solid support residue, a nucleoside or a further compound of structure (I).

The linker L' can be any linker suitable for attaching Q, a targeting moiety, an analyte (e.g., analyte molecule), a solid support, a solid support residue, a nucleoside or a further compound of structure (I) to the compound of structure (I). Advantageously certain embodiments include use of L' moieties selected to increase or optimize water solubility of the compound. In certain embodiments, L' is a heteroalkylene moiety. In some other certain embodiments, L' comprises an alkylene oxide or phosphodiester moiety, or combinations thereof.

In certain embodiments, L' has the following structure:

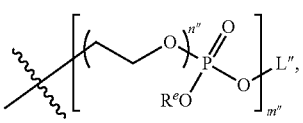

wherein:
  m" and n" are independently an integer from 1 to 10;
  $R^e$ is H, an electron pair or a counter ion;
  L" is $R^e$ or a direct bond or linkage to: Q, a targeting moiety, an analyte (e.g., analyte molecule), a solid support, a solid support residue, a nucleoside or a further compound of structure (I).

In some embodiments, m" is an integer from 4 to 10, for example 4, 6 or 10. In other embodiments n" is an integer from 3 to 6, for example 3, 4, 5 or 6. In some embodiments, n" is an integer from 18-28, for example, from 21-23.

In some other embodiments, L" is an alkylene, alkyleneheterocyclylene, alkyleneheterocyclylenealkylene, alkylenecyclylene, alkylenecyclylenealkylene, heteroalkylene, heteroalkyleneheterocyclylene, heteroalkyleneheterocyclyleneheteroalkylene, heteroalkylenecyclylene, or heteroalkylenecycleneheteroalkylene moiety. In some other certain embodiments, L" comprises an alkylene oxide, phosphodiester moiety, sulfhydryl, disulfide or maleimide moiety or combinations thereof.

In certain of the foregoing embodiments, the targeting moiety is an antibody or cell surface receptor antagonist.

In other more specific embodiments of any of the foregoing compounds of structure (I), $R^1$ or $R^2$ has one of the following structures:

In other more specific embodiments of any of the foregoing compounds of structure (I). $R^1$ or $R^2$ has one of the following structures:

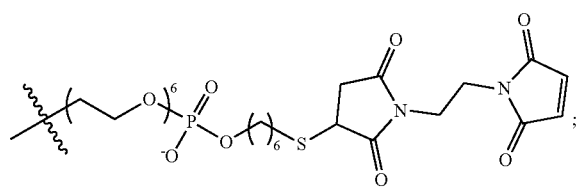

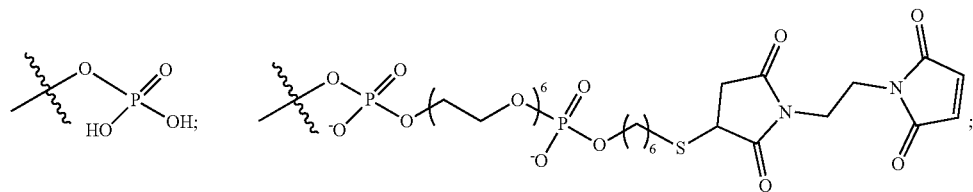

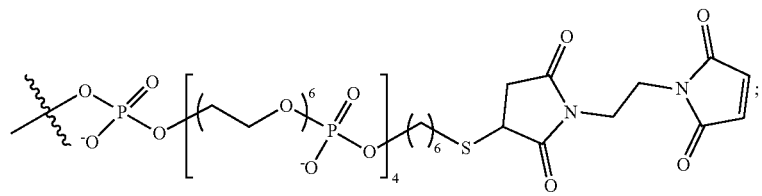

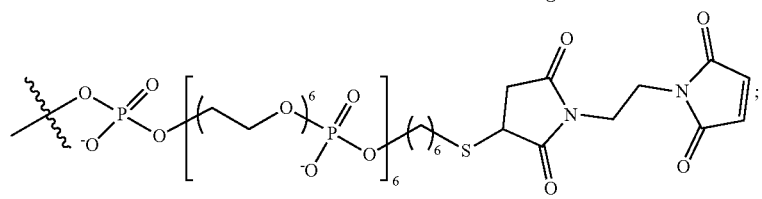

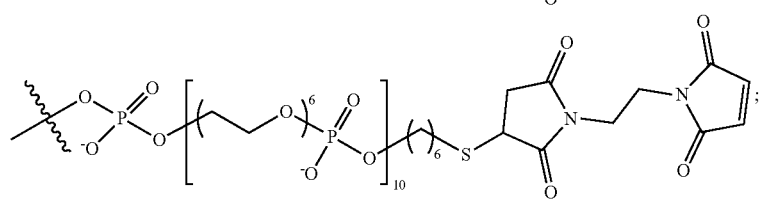

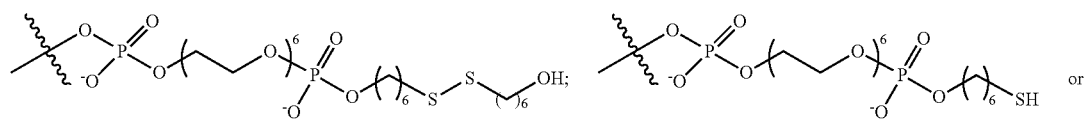

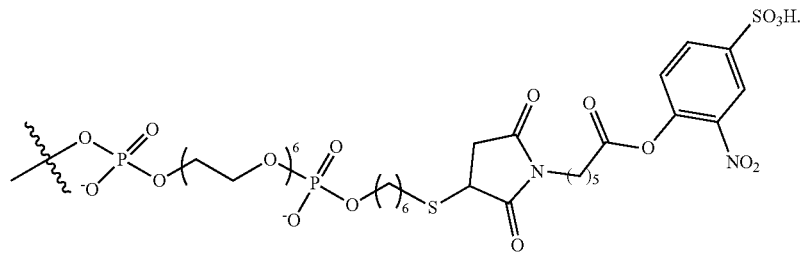

-continued

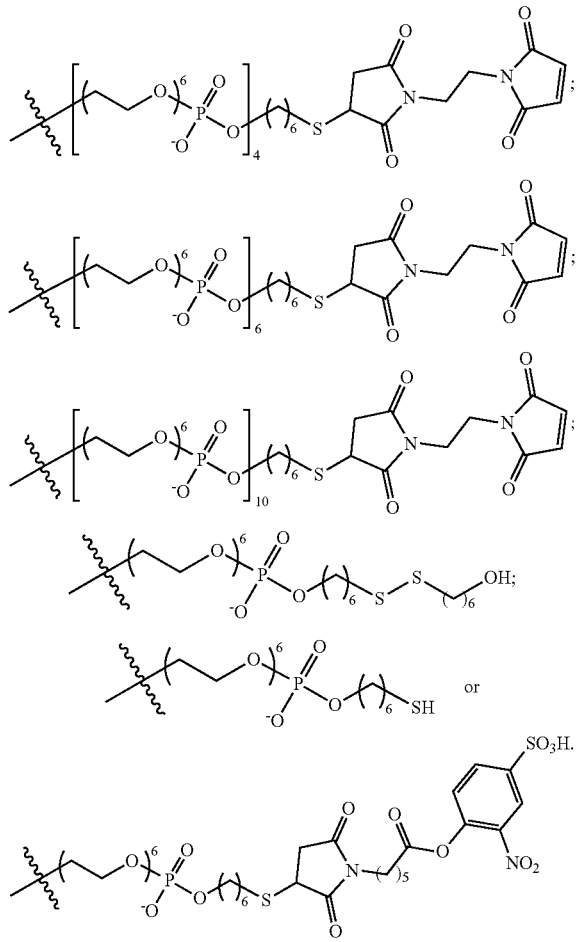

Certain embodiments of compounds of structure (I) can be prepared according to solid-phase synthetic methods analogous to those known in the art for preparation of oligonucleotides. Accordingly, in some embodiments, L' is a linkage to a solid support, a solid support residue or a nucleoside. Solid supports comprising an activated deoxythymidine (dT) group are readily available, and in some embodiments can be employed as starting material for preparation of compounds of structure (I). Accordingly, in some embodiments $R^1$ or $R^2$ has the following structure:

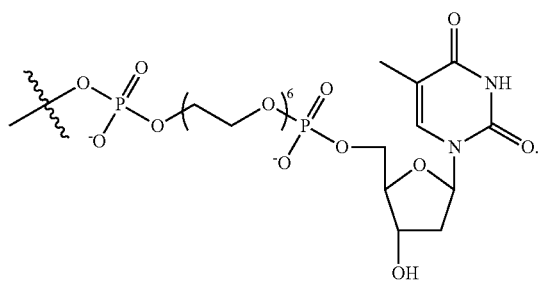

One of skill in the art will understand that the dT group depicted above is included for ease of synthesis and economic efficiencies only, and is not required. Other solid supports can be used and would result in a different nucleoside or solid support residue being present on L', or the nucleoside or solid support residue can be removed or modified post synthesis.

In still other embodiments, Q is, at each occurrence, independently a moiety comprising a reactive group capable of forming a covalent bond with an analyte molecule or a solid support. In other embodiments, Q is, at each occurrence, independently a moiety comprising a reactive group capable of forming a covalent bond with a complementary reactive group Q'. For example, in some embodiments, Q' is present on a further compound of structure (I) (e.g., in the $R^1$ or $R^2$ position), and Q and Q' comprise complementary reactive groups such that reaction of the compound of structure (I) and the further compound of structure (I) results in covalently bound dimer of the compound of structure (I). Multimer compounds of structure (I) can also be prepared in an analogous manner and are included within the scope of embodiments of the disclosure.

The type of Q group and connectivity of the Q group to the remainder of the compound of structure (I) is not limited, provided that Q comprises a moiety having appropriate reactivity for forming the desired bond.

In certain embodiments, Q is a moiety which is not susceptible to hydrolysis under aqueous conditions, but is sufficiently reactive to form a bond with a corresponding group on an analyte molecule or solid support (e.g., an amine, azide or alkyne).

Certain embodiments of compounds of structure (I) comprise Q groups commonly employed in the field of bioconjugation. For example in some embodiments, Q comprises a nucleophilic reactive group, an electrophilic reactive group or a cycloaddition reactive group. In some more specific embodiments, Q comprises a sulfhydryl, disulfide, activated ester, isothiocyanate, azide, alkyne, alkene, diene, dienophile, acid halide, sulfonyl halide, phosphine, α-haloamide, biotin, amino or maleimide functional group. In some embodiments, the activated ester is an N-succinimide ester, imidoester or polyflourophenyl ester. In other embodiments, the alkyne is an alkyl azide or acyl azide.

The Q groups can be conveniently provided in protected form to increase storage stability or other desired properties, and then the protecting group removed at the appropriate time for conjugation with, for example, a targeting moiety or analyte. Accordingly, Q groups include "protected forms" of a reactive group, including any of the reactive groups described above and in the Table 1 below. A "protected form" of Q refers to a moiety having lower reactivity under predetermined reaction conditions relative to Q, but which can be converted to Q under conditions, which preferably do not degrade or react with other portions of the compound of structure (I). One of skill in the art can derive appropriate protected forms of Q based on the particular Q and desired end use and storage conditions. For example, when Q is SH, a protected form of Q includes a disulfide, which can be reduce to reveal the SH moiety using commonly known techniques and reagents.

Exemplary Q moieties are provided in Table I below.

TABLE 1

Exemplary Q Moieties

| Structure | Class |
|---|---|
| —SH | Sulfhydryl |

TABLE 1-continued

Exemplary Q Moieties

| Structure | Class |
|---|---|
| —N=C=S | Isothiocyanate |
| (structure with OMe, NH₂⁺Cl⁻) | Imidoester |
| (acyl azide structure) | Acyl Azide |
| (tetrafluorophenyl ester) | Activated Ester |
| (pentafluorophenyl ester) | Activated Ester |
| (nitro-sulfonate phenyl ester) | Activated Ester |
| (thiosuccinimide-linked nitro-sulfonate phenyl ester) | Activated Ester |
| (NHS ester) | Activated Ester |
| (sulfo-NHS ester) | Activated Ester |
| (sulfonyl halide, X = halo) | Sulfonyl halide |
| (maleimide) | Maleimide |
| (thiosuccinimide-ethyl-maleimide) | Maleimide |
| (SMCC-type maleimide) | Maleimide |
| (α-haloacetamide, X = halo) | α-haloimide |
| (2-pyridyl disulfide) | Disulfide |
| (phosphine structure with Ph₂P and CO₂Me) | Phosphine |
| —N₃ | Azide |

TABLE 1-continued

Exemplary Q Moieties

| Structure | Class |
|---|---|
| (alkyne structure) | Alkyne |
| (biotin structure) | Biotin |
| (diene structure) | Diene |
| (alkene structure) | Alkene/dienophile |
| (alkene with EWG) | Alkene/dienophile |

EWG = eletron withdrawing group

TABLE 1-continued

Exemplary Q Moieties

| Structure | Class |
|---|---|
| —NH$_2$ | Amino |

It should be noted that in some embodiments, wherein Q is SH, the SH moiety will tend to form disulfide bonds with another sulfhydryl group, for example on another compound of structure (I). Accordingly, some embodiments include compounds of structure (I), which are in the form of disulfide dimers, the disulfide bond being derived from SH Q groups.

Also included within the scope of certain embodiments are compounds of structure (I), wherein one, or both, of $R^1$ and $R^2$ comprises a linkage to a further compound of structure (I). For example, wherein one or both of $R^1$ and $R^2$ are —OP(=$R_a$)($R_b$)$R_c$, and Rc is OL', and L' is a linker comprising a covalent bond to a further compound of structure (I). Such compounds can be prepared by preparing a first compound of structure (I) having for example about 10 "$M^1$" and/or "$M^2$" moieties (i.e., n=10) and having an appropriate "Q" for reaction with a complementary Q' group on a second compound of structure (I). In this manner, compounds of structure (I), having any number of "$M^1$" and/or "$M^2$" moieties, for example 100 or more, can be prepared without the need for sequentially coupling each monomer. Exemplary embodiments of such compounds of structure (I) have the following structure (I'):

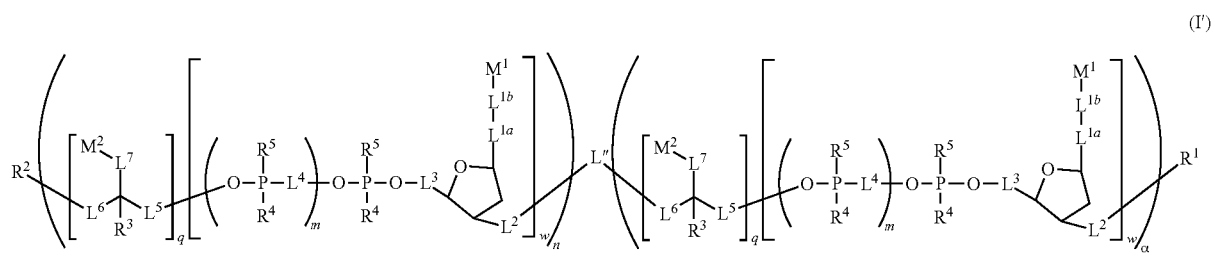

(I')

wherein:
each occurrence of $R^1$, $R^2$, $R^3$, $R^4$, $R^5$, $L^{1a}$, $L^{1b}$, $L^2$, $L^3$, $L^4$, $L^5$, $L^6$, $L^7$, $M^1$, $M^1$, q, m, w and n are independently as defined for a compound of structure (I);
L" is a linker comprising a functional group resulting from reaction of a Q moiety with a corresponding Q' moiety; and
α is an integer greater than 1, for example from 1 to 100, or 1 to 10.

Compounds of structure (I') are derivable by those of ordinary skill in the art, for example by dimerizing or polymerizing compounds of structure (I) provided herein.

In other embodiments, the Q moiety is conveniently masked (e.g., protected) as a disulfide moiety, which can later be reduced to provide an activated Q moiety for binding to a desired analyte molecule or targeting moiety. For example, the Q moiety may be masked as a disulfide having the following structure:

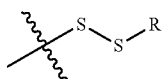

wherein R is an optionally substituted alkyl group. For example, in some embodiments, Q is provided as a disulfide moiety having the following structure:

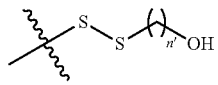

where n is an integer from 1 to 10.

In some other embodiments, one of $R^1$ or $R^2$ is OH or —OP(=$R_a$)($R_b$)$R_c$, and the other of $R^1$ or $R^2$ is a linker comprising a covalent bond to an analyte molecule or a linker comprising a covalent bond to a solid support. For example, in some embodiments the analyte molecule is a nucleic acid, amino acid or a polymer thereof. In other embodiments, the analyte molecule is an enzyme, receptor, receptor ligand, antibody, glycoprotein, aptamer or prion. In some embodiments, the targeting moiety is an antibody or cell surface receptor antagonist. In still different embodiments, the solid support is a polymeric bead or non-polymeric bead.

The fluorescence intensity can also be tuned by selection of different values of n. In certain embodiments, n is an integer from 1 to 100. In other embodiments, n is an integer from 1 to 10. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

The fluorescence may also be tuned by selection of values for m. In certain embodiments, m is an integer from 1 to 100. In other embodiments, m is an integer from 7 to 12. In some embodiments, m is an integer from 20 to 26. In some embodiments, m is an integer from 3 to 6. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11.

$M^1$ and $M^2$ are selected based on the desired optical properties, for example based on a desired color and/or fluorescence emission wavelength. In some embodiments, $M^1$ and $M^2$ are the same at each occurrence; however, it is important to note that each occurrence of $M^1$ and $M^2$ need not be an identical $M^1$ and $M^2$, and certain embodiments include compounds wherein $M^1$ and $M^2$ are not the same at each occurrence. For example, in some embodiments each $M^1$ and $M^2$ are not the same and the different $M^1$ and $M^2$ moieties are selected to have absorbance and/or emissions for use in fluorescence resonance energy transfer (FRET) methods. For example, in such embodiments the different $M^1$ and $M^2$ moieties are selected such that absorbance of radiation at one wavelength causes emission of radiation at a different wavelength by a FRET mechanism. Exemplary $M^1$ and $M^2$ moieties can be appropriately selected by one of ordinary skill in the art based on the desired end use. Exemplary $M^1$ and $M^2$ moieties for FRET methods include fluorescein and 5-TAMRA (5-carboxytetramethylrhodamine, succinimidyl ester) dyes.

$M^1$ or $M^2$ may be attached to the remainder of the molecule from any position (i.e., atom) on $M^1$ or $M^2$, respectively. One of skill in the art will recognize means for attaching $M^1$ or $M^2$ to the remainder of molecule. Exemplary methods include the "click" reactions described herein.

In some embodiments, $M^1$ and $M^2$ are, at each occurrence, independently a fluorescent or colored moiety. Any fluorescent and/or colored moiety may be used, for examples those known in the art and typically employed in colorimetric, UV, and/or fluorescent assays may be used. Examples of $M^1$ and $M^2$ moieties which are useful in various embodiments of the disclosure include, but are not limited to: Xanthene derivatives (e.g., fluorescein, rhodamine, Oregon green, eosin or Texas red); Cyanine derivatives (e.g., cyanine, indocarbocyanine, oxacarbocyanine, thiacarbocyanine or merocyanine); Squaraine derivatives and ring-substituted squaraines, including Seta, SeTau, and Square dyes; Naphthalene derivatives (e.g., dansyl and prodan derivatives); Coumarin derivatives; oxadiazole derivatives (e.g., pyridyloxazole, nitrobenzoxadiazole or benzoxadiazole); Anthracene derivatives (e.g., anthraquinones, including DRAQ5, DRAQ7 and CyTRAK Orange); Pyrene derivatives such as cascade blue; Oxazine derivatives (e.g., Nile red, Nile blue, cresyl violet, oxazine 170); Acridine derivatives (e.g., proflavin, acridine orange, acridine yellow); Arylmethine derivatives: auramine, crystal violet, malachite green; and Tetrapyrrole derivatives (e.g., porphin, phthalocyanine or bilirubin). Other exemplary $M^1$ and $M^2$ moieties include: Cyanine dyes, xanthate dyes (e.g., Hex, Vic, Nedd, Joe or Tet); Yakima yellow; Redmond red; tamra; texas red and alexa fluor® dyes.

In still other embodiments of any of the foregoing, $M^1$ and $M^2$ each occurrence independently comprises three or more aryl or heteroaryl rings, or combinations thereof, for example four or more aryl or heteroaryl rings, or combinations thereof, or even five or more aryl or heteroaryl rings, or combinations thereof. In some embodiments, $M^1$ and $M^2$ each occurrence independently comprises six aryl or heteroaryl rings, or combinations thereof. In further embodiments, the rings are fused. For example in some embodiments, $M^1$ and $M^2$ each occurrence independently comprises three or more fused rings, four or more fused rings, five or more fused rings, or even six or more fused rings.

In some embodiments, $M^1$ and $M^2$ are, at each occurrence, independently cyclic. For example, in some embodiments $M^1$ and $M^2$ are, at each occurrence, independently carbocyclic. In other embodiment, $M^1$ and $M^2$ are, at each occurrence, independently heterocyclic. In still other embodiments of the foregoing, $M^1$ and $M^2$, at each occurrence, independently comprises an aryl moiety. In some of these embodiments, the aryl moiety is multicyclic. In other more specific examples, the aryl moiety is a fused-multicyclic aryl moiety, for example which may comprise at least 2, at least 3, at least 4, or even more than 4 aryl rings.

In other embodiments of any of the foregoing compounds of structure (I), (Ia), (Ib), (Ic), (Id), (Ie) or (I'), $M^1$ or $M^2$, at each occurrence, independently comprises at least one heteroatom. For example, in some embodiments, the heteroatom is nitrogen, oxygen or sulfur.

In still more embodiments of any of the foregoing, $M^1$ and $M^2$, at each occurrence, independently comprises at least one substituent. For example, in some embodiments the substituent is a fluoro, chloro, bromo, iodo, amino, alkylamino, arylamino, hydroxy, sulfhydryl, alkoxy, aryloxy, phenyl, aryl, methyl, ethyl, propyl, butyl, isopropyl, t-butyl, carboxy, sulfonate, amide, or formyl group.

In some even more specific embodiments of the foregoing, $M^1$ and $M^2$, at each occurrence, independently is a dimethylaminostilbene, quinacridone, fluorophenyl-dimethyl-BODIPY, his-fluorophenyl-BODIPY, acridine, terrylene, sexiphenyl, porphyrin, benzopyrene, (fluorophenyl-dimethyl-difluorobora-diaza-indacene) phenyl, (bis-fluorophenyl-difluorobora-diaza-indacene) phenyl, quaterphenyl, bi-benzothiazole, ter-benzothiazole, bi-naphthyl, bi-anthracyl, squaraine, squarylium, 9,10-ethynylanthracene or ter-naphthyl moiety. In other embodiments, $M^1$ and $M^2$ are, at each occurrence, independently p-terphenyl, perylene, azobenzene, phenazine, phenanthroline, acridine, thioxanthrene, chrysene, rubrene, coronene, cyanine, perylene imide, or perylene amide or a derivative thereof. In still more embodiments, $M^1$ and $M^2$ are, at each occurrence, independently a coumarin dye, resorufin dye, dipyrromethenboron difluoride dye, ruthenium bipyridyl dye, energy transfer dye, thiazole orange dye, polymethine or N-aryl-1,8-naphthalimide dye.

In still more embodiments of any of the foregoing, $M^1$ and $M^2$ at each occurrence are the same. In other embodiments, each $M^1$ and $M^2$ are different. In still more embodiments, one or more $M^1$ and $M^2$ are the same and one or more $M^1$ and $M^2$ are different.

In some embodiments, $M^1$ and $M^2$ are, at each occurrence independently pyrene, perylene, perylene monoimide or 6-FAM or a derivative thereof. In some other embodiments, $M^1$ and $M^2$, at each occurrence, independently has one of the following structures:

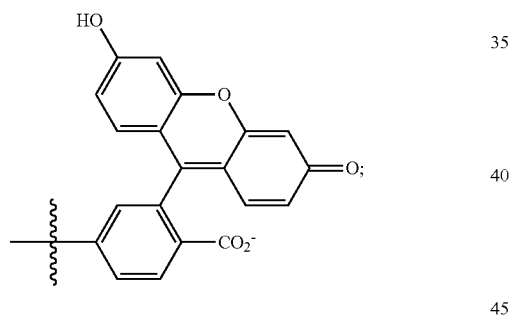

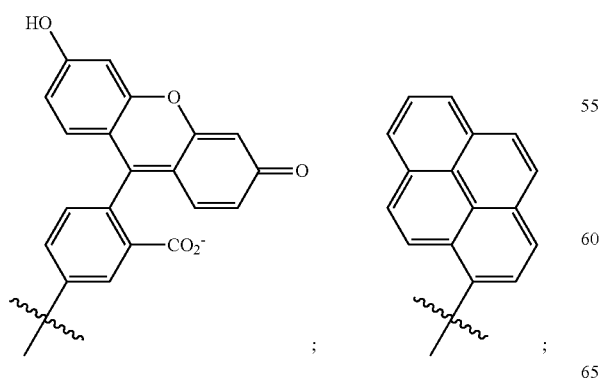

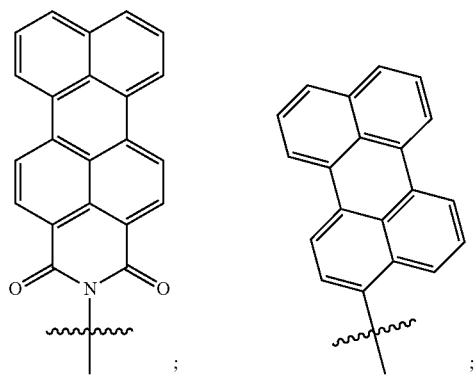

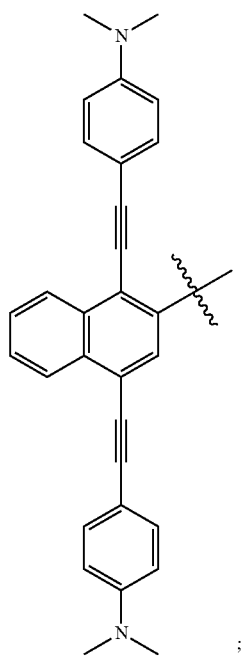

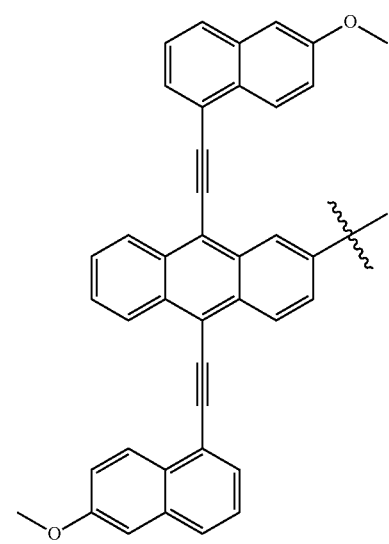

or

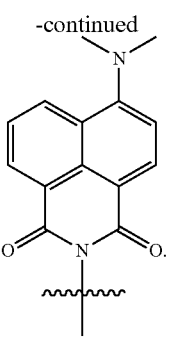

Although $M^1$ and $M^2$ moieties comprising carboxylic acid groups are depicted in the anionic form ($CO_2^-$) above, one of skill in the art will understand that this will vary depending on pH, and the protonated form (i.e., $-CO_2H$) is included in various embodiments.

In some specific embodiments, the compound is a compound selected from Table 2. The compounds in Table 2 were prepared according to the procedures set forth in the Examples and their identity confirmed by mass spectrometry.

TABLE 2

Exemplary Compounds of Structure I

| No. | MW. Found Calc. | Structure |
|---|---|---|
| I-1 | 15141.9 15137 | |
| I-2 | 7924.2 7969.7† (avg) | |

TABLE 2-continued

Exemplary Compounds of Structure I

| No. | MW. Found Calc. | Structure |
|---|---|---|
| I-3 | 14449.3 — | 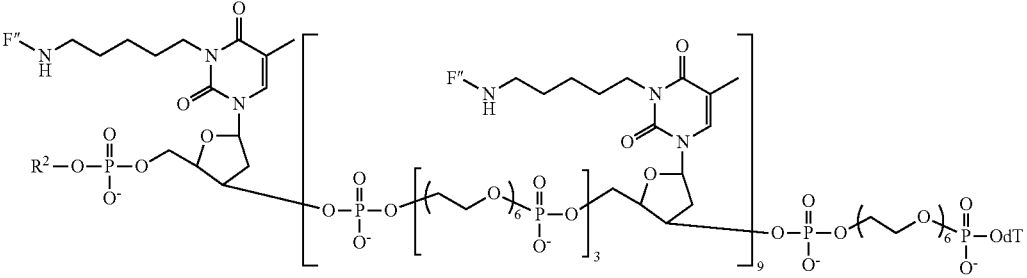 |

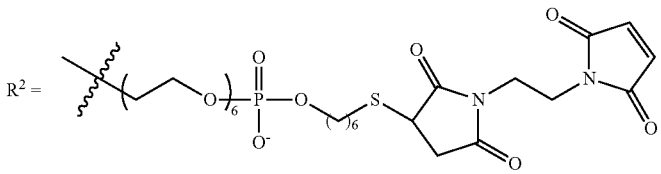

†Compound I-2 is drawn as a structure representing the average molecular weight (i.e., having 23 ethylene glycol units)

As used in Table 2 and throughout the application $R^1$, $R^2$, n, and L' have the definitions provided for compounds of structure (I) unless otherwise indicated, and F, F' and F" refer to a fluorescein moiety having the following structures, respectively:

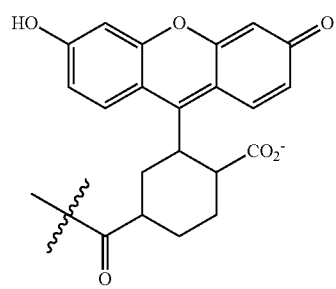

F

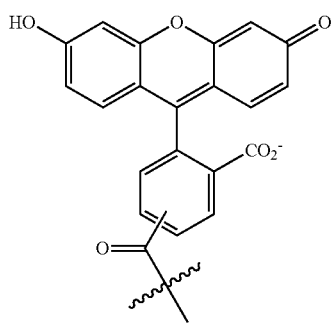

F'

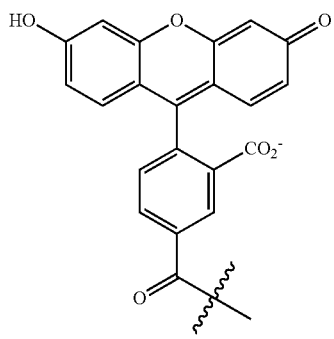

F"

In some embodiments, $M^1$ or $M^2$ is, at each occurrence, independently F, F' or F".

It is well known in the art that fluorescein moieties tautomerize between quinoid, zwitterionic, and lactoid forms. One of skill in the art will readily understand that the form is dependent on pH and each form (e.g., quinoid, zwitterionic, and lactoid) are also included in the scope of embodiments of the disclosure.

As used in Tables 2 above and throughout this disclosure dT refers to the following structure:

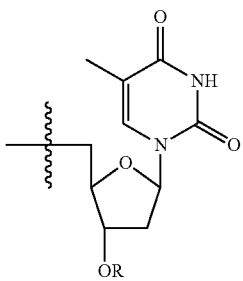

dT wherein:

R is H or a direct bond.

As used throughout this disclosure, B and B' refer to the following structures, respectively:

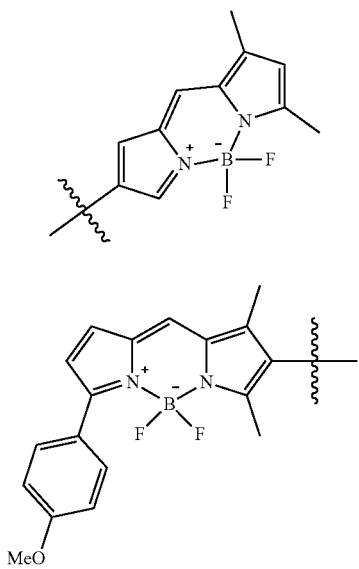

B

B'

In some embodiments, $M^1$ or $M^2$ is, at each occurrence, independently B or B'.

As used throughout this disclosure, T refers to the following structure:

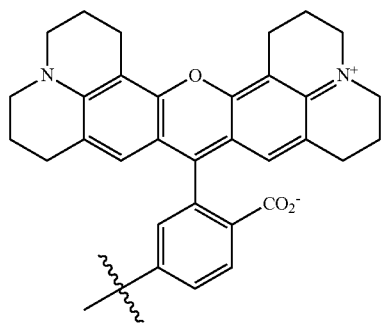

T

In specific embodiments, $M^1$ or $M^2$ is, at each occurrence, independently T.

As used throughout this disclosure, C refers to the following structure:

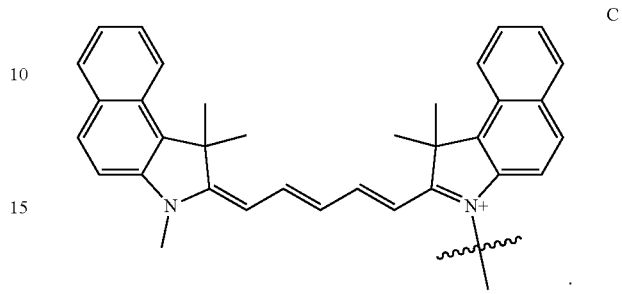

C

In some embodiments, $M^1$ or $M^2$ is, at each occurrence, independently C.

As used throughout this disclosure, Y refers to the following structure:

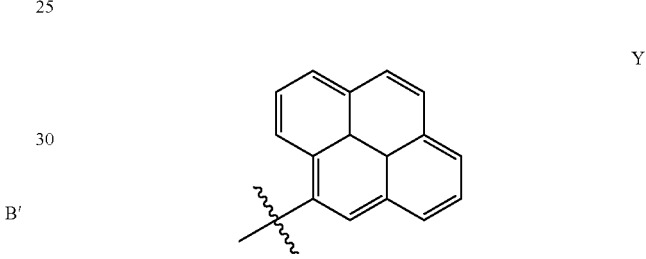

Y

In some embodiments, $M^1$ or $M^2$ is, at each occurrence, independently Y.

Some embodiments include any of the foregoing compounds, including the specific compounds provided in Table 2, conjugated to a targeting moiety, such as an antibody.

The present disclosure generally provides compounds having increased fluorescence emission relative to earlier known compounds. Accordingly, certain embodiments are directed to a fluorescent compound comprising n fluorescent moieties $M^1$ and/or $M^2$, wherein the fluorescent compound has a peak fluorescence emission upon excitation with a predetermined wavelength of ultraviolet light of at least 85% of n times greater than the peak fluorescence emission of a single $M^1$ or $M^2$ moiety upon excitation with the same wavelength of ultraviolet light, and wherein n is an integer of 2 or more. Fluorescent compounds include compounds which emit a fluorescent signal upon excitation with light, such as ultraviolet light.

In some embodiments, the fluorescent compound has a peak fluorescence emission of at least 90% of n times greater, 95% of n times greater, 97% of n times greater or 99% of n times greater than the peak fluorescence emission of a single $M^1$ and/or $M^2$ moiety.

In some embodiments, n is an integer from 2 to 100, for example 2-10.

In some embodiments, the n $M^1$ and/or $M^2$ moieties have, independently, one of the following structures:

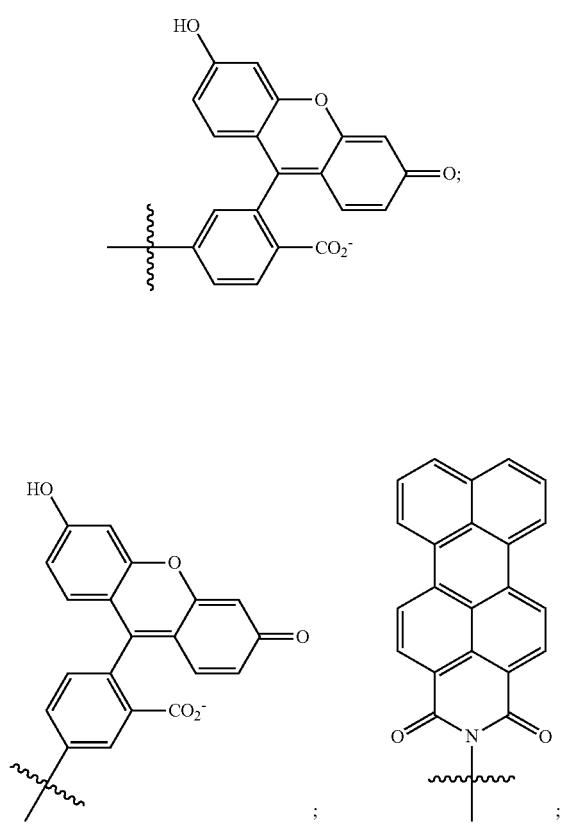
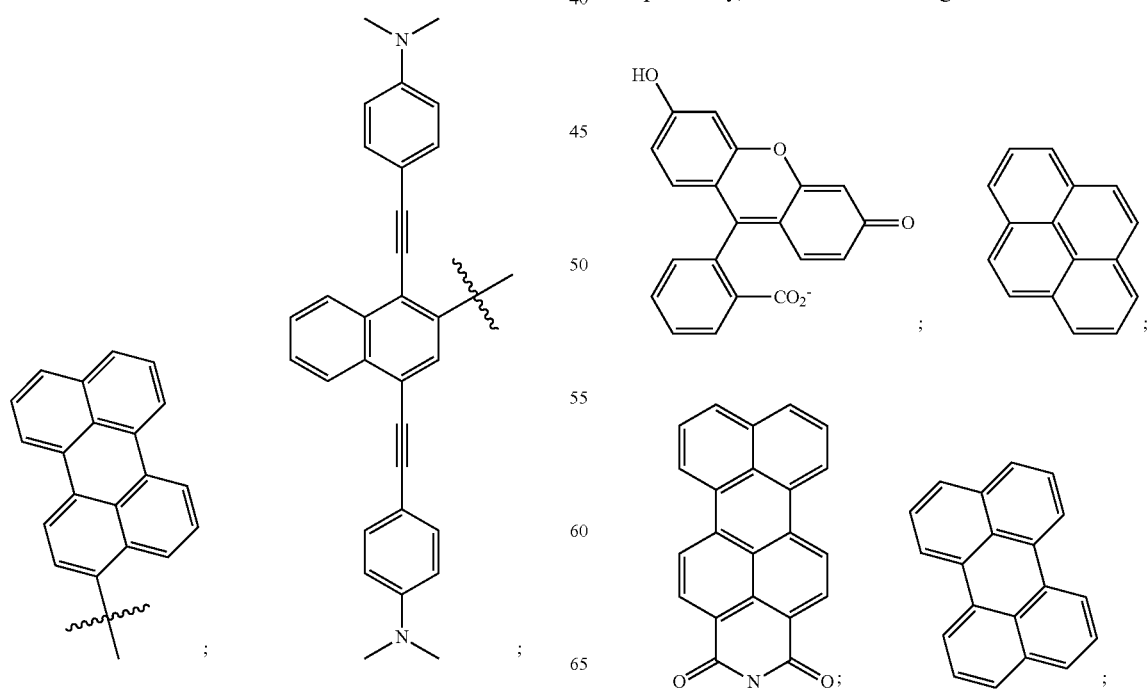
wherein ⁓ indicates a point of attachment to the fluorescent compound.
In other embodiments, the single $M^1$ or $M^2$ moiety has, independently, one of the following structures:

-continued

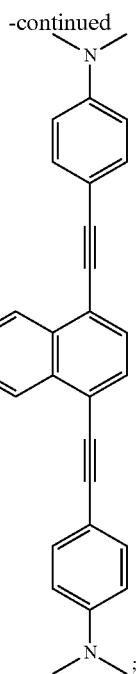

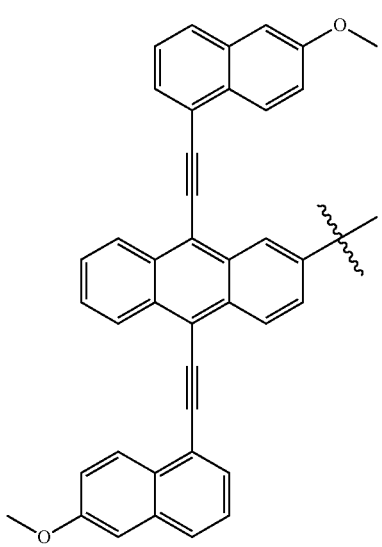

or

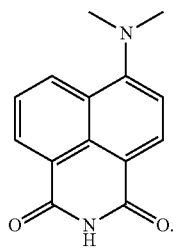

In more specific embodiments, the fluorescent compound comprises n $M^1$ and/or $M^2$ moieties, independently having one of the following structures:

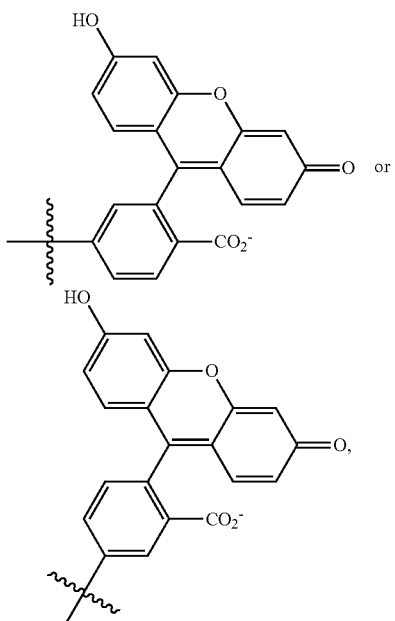

wherein ⌇ indicates a point of attachment to the fluorescent compound, and the single $M^1$ or $M^2$ moiety has the following structure:

In other embodiments, the peak fluorescence emission is at a wavelength ranging from about 500 to about 550 nm.

In still more embodiments, the fluorescent compound comprises at least one ethylene oxide moiety.

Compositions comprising the fluorescent compound of any one of claims and an analyte are also provided.

The presently disclosed compounds are "tunable," meaning that by proper selection of the variables in any of the foregoing compounds, one of skill in the art can arrive at a compound having a desired and/or predetermined molar fluorescence (molar brightness). The tunability of the compounds allows the user to easily arrive at compounds having the desired fluorescence and/or color for use in a particular assay or for identifying a specific analyte of interest. Although all variables may have an effect on the molar fluorescence of the compounds, proper selection of $M^1$, $M^2$, $L^{1a}$, $L^{1b}$, $L^3$, $L^4$, q, w, m and n is believed to play an important role in the molar fluorescence of the compounds. Accordingly, in one embodiment is provided a method for obtaining a compound having a desired molar fluorescence, the method comprising selecting $M^1$ or $M^2$ moieties having a known fluorescence, preparing a compound of structure (I) comprising the $M^1$ or $M^2$ moieties, and selecting the appropriate variables for $M^1$, $M^2$, $L^{1a}$, $L^{1b}$, $L^3$, $L^4$, q, w, m and n to arrive at the desired molar fluorescence.

Molar fluorescence in certain embodiments can be expressed in terms of the fold increase or decrease relative to the fluorescence emission of the parent fluorophore (e.g., monomer). In some embodiments the molar fluorescence of the present compounds is 1.1×, 1.5×, 2×, 3×, 4×, 5×, 6×, 7×, 8×, 9×, 10× or even higher relative to the parent fluorophore. Various embodiments include preparing compounds having the desired fold increase in fluorescence relative to the parent fluorophore by proper selection of $M^1$, $M^2$, $L^{1a}$, $L^{1b}$, $L^3$, $L^4$, q, w, m and n.

For ease of illustration, various compounds comprising phosphorous moieties (e.g., phosphate and the like) are depicted in the anionic state (e.g., —OPO(OH)O$^-$, —OPO$_3^{2-}$). One of skill in the art will readily understand that the charge is dependent on pH and the uncharged (e.g., protonated or salt, such as sodium or other cation) forms are also included in the scope of embodiments of the disclosure.

Compositions comprising any of the foregoing compounds and one or more analyte molecules (e.g., biomolecules) are provided in various other embodiments. In some embodiments, use of such compositions in analytical methods for detection of the one or more analyte molecules is also provided.

In still other embodiments, the compounds are useful in various analytical methods. For example, in certain embodiments the disclosure provides a method of staining a sample, the method comprising adding to said sample a compound of structure (I), for example wherein one of $R^1$ or $R^2$ is a linker comprising a covalent bond to an analyte molecule (e.g., biomolecule) or microparticle, and the other of $R^1$ or $R^2$ is H, OH, alkyl, alkoxy, alkylether or —OP(=$R_a$)($R_b$)$R_c$, in an amount sufficient to produce an optical response when said sample is illuminated at an appropriate wavelength.

In some embodiments of the foregoing methods, $R^1$ is a linker comprising a covalent linkage to an analyte molecule, such as a biomolecule. For example, in some embodiments the biomolecule is a nucleic acid, amino acid or a polymer thereof (e.g., polynucleotide or polypeptide). In still more embodiments, the biomolecule is an enzyme, receptor, receptor ligand, antibody, glycoprotein, aptamer or prion.

In yet other embodiments of the foregoing method, $R^1$ is a linker comprising a covalent linkage to a solid support such as a microparticle. For example, in some embodiments the microparticle is a polymeric bead or non-polymeric bead.

In even more embodiments, said optical response is a fluorescent response.

In other embodiments, said sample comprises cells, and some embodiments further comprise observing said cells by flow cytometry.

In still more embodiments, the method further comprises distinguishing the fluorescence response from that of a second fluorophore having detectably different optical properties.

In other embodiments, the disclosure provides a method for visually detecting an analyte molecule, such as a biomolecule, comprising:
 (a) providing a compound of structure (I), for example, wherein one of $R^1$ or $R^2$ is a linker comprising a covalent bond to the analyte molecule, and the other of $R^1$ or $R^2$ is H, OH, alkyl, alkoxy, alkylether or —OP(=$R_a$)($R_b$)$R_c$; and
 (b) detecting the compound by its visible properties.

In some embodiments the analyte molecule is a nucleic acid, amino acid or a polymer thereof (e.g., polynucleotide or polypeptide). In still more embodiments, the analyte molecule is an enzyme, receptor, receptor ligand, antibody, glycoprotein, aptamer or prion.

In other embodiments, a method for visually detecting an analyte molecule, such as a biomolecule is provided, the method comprising:
 (a) admixing any of the foregoing compounds with one or more analyte molecules; and
 (b) detecting the compound by its visible properties.

In other embodiments is provided a method for visually detecting an analyte molecule, the method comprising:
 (a) admixing the compound of structure (I), wherein $R^1$ or $R^2$ is Q or a linker comprising a covalent bond to Q, with the analyte molecule;
 (b) forming a conjugate of the compound and the analyte molecule; and
 (c) detecting the conjugate by its visible properties.

Other exemplary methods include a method for detecting an analyte, the method comprising:
 (a) providing a compound of structure (I), wherein $R^1$ or $R^2$ comprises a linker comprising a covalent bond to a targeting moiety having specificity for the analyte;
 (b) admixing the compound and the analyte, thereby associating the targeting moiety and the analyte; and
 (c) detecting the compound, for example by its visible or fluorescent properties.

In certain embodiments of the foregoing method, the analyte is a particle, such as a cell, and the method includes use of flow cytometry. For example, the compound may be provided with a targeting moiety, such as an antibody, for selectively associating with the desired cell, thus rendering the cell detectable by any number of techniques, such as visible or fluorescence detection. Appropriate antibodies can be selected by one of ordinary skill in the art depending on the desired end use. Exemplary antibodies for use in certain embodiments include UCHT1 and MOPC-21.

Embodiments of the present compounds thus find utility in any number of methods, including, but not limited: cell counting; cell sorting; biomarker detection; quantifying apoptosis; determining cell viability; identifying cell surface antigens; determining total DNA and/or RNA content; identifying specific nucleic acid sequences (e.g., as a nucleic acid probe); and diagnosing diseases, such as blood cancers.

In addition to the above methods, embodiments of the compounds of structure (I) find utility in various disciplines and methods, including but not limited to: imaging in endoscopy procedures for identification of cancerous and other tissues; single-cell and/or single molecule analytical methods, for example detection of polynucleotides with little or no amplification; cancer imaging, for example by including a targeting moiety, such as an antibody or sugar or other moiety that preferentially binds cancer cells, in a compound of structure (I) to; imaging in surgical procedures; binding of histones for identification of various diseases; drug delivery, for example by replacing the $M^1$ or $M^2$ moieties in a compound of structure (I) with an active drug moiety; and/or contrast agents in dental work and other procedures, for example by preferential binding of the compound of structure (I) to various flora and/or organisms.

It is understood that any embodiment of the compounds of structure (I), as set forth above, and any specific choice set forth herein for a $R^1$, $R^2$, $R^3$, $R^4$, $R^5$, $L^1$, $L^2$, $L^3$, $L^4$, $L^5$, $L^6$, $L^7$, $M^1$, $M^2$, q, w, m and/or n variable in the compounds of structure (I), as set forth above, may be independently combined with other embodiments and/or variables of the compounds of structure (I) to form embodiments of the disclosure not specifically set forth above. In addition, in the event that a list of choices is listed for any particular $R^1$, $R^2$, $R^3, R^4, R^5, L^1, L^2, L^3, L^4, L^5, L^6, L^7, M^1, M^2$, q, w, m and/or n variable in a particular embodiment and/or claim, it is understood that each individual choice may be deleted from the particular embodiment and/or claim and that the remaining list of choices will be considered to be within the scope of the disclosure.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3$^{rd}$ Ed., Wiley. As one of skill in the art would appreciate, the protecting group may also be a polymer resin such as a Wang resin, Rink resin or a 2-chlorotrityl-chloride resin.

Furthermore, all compounds of the disclosure which exist in free base or acid form can be converted to their salts by treatment with the appropriate inorganic or organic base or acid by methods known to one skilled in the art. Salts of the compounds of the disclosure can be converted to their free base or acid form by standard techniques.

The following Reaction Schemes illustrate exemplary methods of making compounds of this disclosure. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, *Advanced Organic Chemistry: Reactions, Mechanisms, and Structure*, 5$^{th}$ edition (Wiley, December 2000)) or prepared as described in this disclosure.

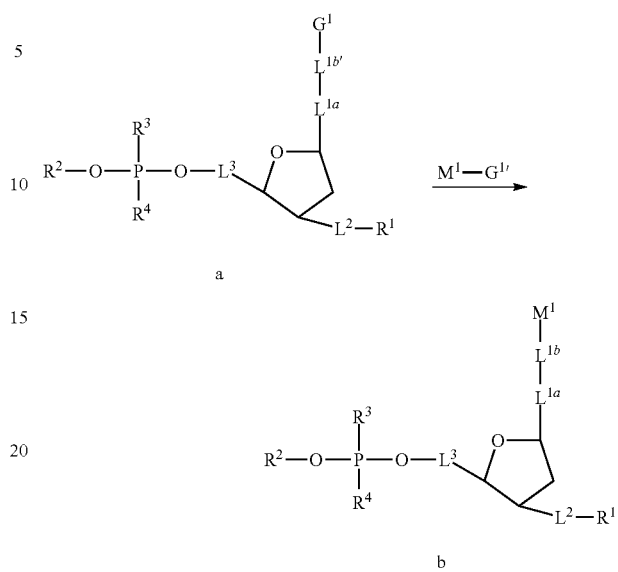

Reaction Scheme I

Reaction Scheme I illustrates a method for preparation of intermediates useful for preparation of compounds of structure (I). Referring to reaction Scheme I, wherein $L^{1a}$, $L^{1b}$, $L^{1b'}$, $L^2$, $L^3$, $G^1$ and $M^1$ are as defined above, and $R^1$ and $R^2$ are as defined above, or are protected variants thereof, a compound of structure a, which can be purchased or prepared by well-known techniques, is reacted with M-$G^{1'}$ to yield compounds of structure b. Here, $G^1$ and $G^{1'}$ represent functional groups having complementary reactivity (i.e., functional groups which react to form a covalent bond). $G^{1'}$ may be pendant to $M^1$ or a part of the structural backbone of $M^1$. $G^1$ and $G^{1'}$ may be any number of functional groups described herein, such as alkyne and azide, respectively, amine and activated ester, respectively or amine and isothiocyanate, respectively, and the like. $M^2$ can be attached to form a compound of structure (I) in an analogous manner by selecting appropriate reagents according to Reaction Scheme I above.

Additionally, compounds of the present disclosure can be prepared according to the methods described in PCT Pub. Nos. WO 2016/183185; WO 2017/173355; and WO 2017/177065, each of which are hereby incorporated by reference.

The compound of structure (I) may be prepared from structure b by reaction under well-known automated DNA synthesis conditions with a phosphoramidite compound having the following structure (c):

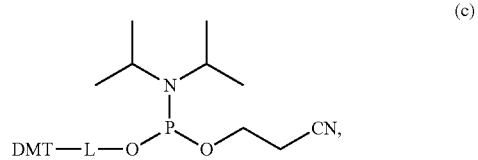

(c)

wherein L is an optional linker (e.g., $L^4$). In some embodiments of (c), L has one of the following structures:

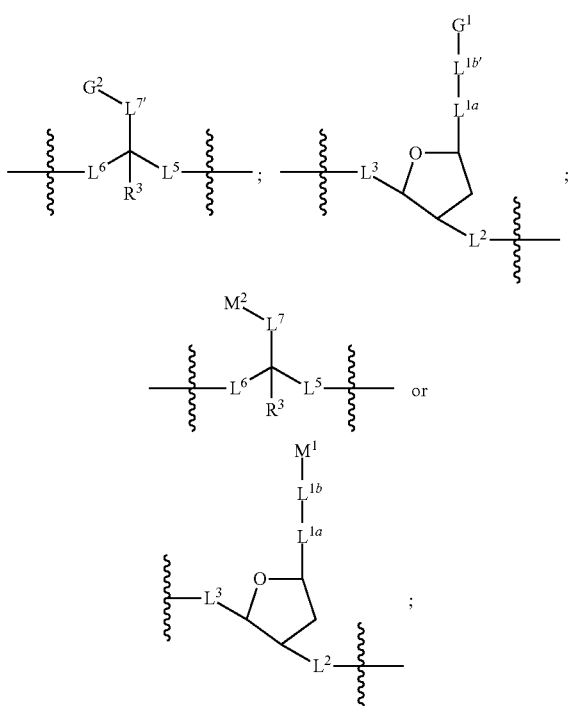

DNA synthesis methods are well-known in the art. Briefly, two alcohol groups, for example $R^1$ and $R^2$ in intermediate b above, are functionalized with a dimethoxytrityl (DMT) group and a 2-cyanoethyl-N,N-diisopropylamino phosphoramidite group, respectively. The phosphoramidite group is coupled to an alcohol group, typically in the presence of an activator such as tetrazole, followed by oxidation of the phosphorous atom with iodine. The dimethoxytrityl group can be removed with acid (e.g., chloroacetic acid) to expose the free alcohol, which can be reacted with a phosphoramidite group. The 2-cyanoethyl group can be removed after oligomerization by treatment with aqueous ammonia.

Preparation of the phosphoramidites used in the oligomerization methods is also well-known in the art. For example, a primary alcohol (e.g., $R^1$) can be protected as a DMT group by reaction with DMT-Cl. A secondary alcohol (e.g., $R^2$) is then functionalized as a phosphoramidite by reaction with an appropriate reagent such as 2-cyanoethyl N,N-diisopropylchlorophosphoramidite. Methods for preparation of phosphoramidites and their oligomerization are well-known in the art and described in more detail in the examples.

Compounds of structure (I) are prepared by oligomerization of intermediates b and c according to the well-known phophoramidite chemistry described above. The desired number of n repeating units is incorporated into the molecule by repeating the phosphoramidite coupling the desired number of times. It will be appreciated that compounds of structure (II) as, described below, can be prepared by analogous methods.

In various other embodiments, compounds useful for preparation of the compound of structure (I) are provided. The compounds can be prepared as described above in monomer, dimer and/or oligomeric form and then the $M^1$ and/or $M^2$ moiety covalently attached to the compound via any number of synthetic methodologies (e.g., the "click" reactions described above) to form a compound of structure (I). Accordingly, in various embodiments a compound is provided having the following structure (II):

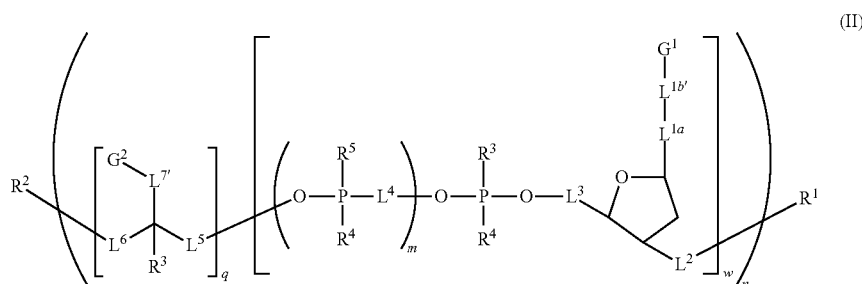

(II)

wherein:

$L^{1a}$, $L^{1b}$, $L^{1b'}$, $L^2$, $L^3$, $L^5$, $L^6$, $L^7$, $L^{7'}$, $G^1$, $G^2$, $M^2$ and $M^1$ are as defined herein.

or a stereoisomer, salt or tautomer thereof, wherein:

$G^1$ and $G^2$ are, at each occurrence, independently a moiety comprising a reactive group, or protected analogue thereof, capable of forming a covalent bond with a complementary reactive group;

$L^{1a}$ is at each occurrence, independently a heteroarylene linker;

$L^{1b'}$, $L^2$, $L^3$, $L^5$, $L^6$, and $L^{7'}$ are, at each occurrence, independently optional alkylene, alkenylene, alkynylene, heteroalkylene, heteroalkenylene or heteroalkynylene linkers;

$L^4$ is, at each occurrence, independently an alkylene, alkenylene, alkynylene, heteroalkylene, heteroalkenylene or heteroalkynylene linker;

$R^1$ and $R^2$ are each independently H, OH, SH, alkyl, alkoxy, alkylether, heteroalkyl, $-OP(=R_a)(R_b)R_c$, Q, or a protected form thereof, or L';

$R^3$ is, at each occurrence, independently H, alkyl or alkoxy;

$R^4$ is, at each occurrence, independently OH, SH, O$^-$, S$^-$, OR$_d$ or SR$_d$;

$R^5$ is, at each occurrence, independently oxo, thioxo or absent;

$R_a$ is O or S;

$R_b$ is OH, SH, O⁻, S⁻, $OR_d$ or $SR_d$;

$R_c$ is OH, SH, O⁻, S⁻, $OR_d$, OL', $SR_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

$R_d$ is a counter ion;

Q is, at each occurrence, independently a moiety comprising a reactive group, or protected form thereof, capable of forming a covalent bond with an analyte molecule, a targeting moiety, a solid support or a complementary reactive group Q';

L' is, at each occurrence, independently a linker comprising a covalent bond to Q, a linker comprising a covalent bond to a targeting moiety, a linker comprising a covalent bond to an analyte molecule, a linker comprising a covalent bond to a solid support, a linker comprising a covalent bond to a solid support residue, a linker comprising a covalent bond to a nucleoside or a linker comprising a covalent bond to a further compound of structure (I);

m is, at each occurrence, an integer of one or greater;

n is an integer of one or greater; and q and w are, at each occurrence, independently 0 or 1, provided at least one occurrence of w is 1. In some embodiments, q is 0.

In some embodiments of compound (II), $L^{1a}$ has one of the following structures:

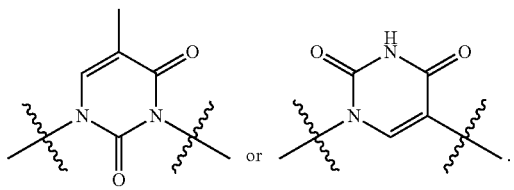 [SMILES: *n1cc(C)c(=O)n(*)c1=O ; *c1cn(*)c(=O)[nH]c1=O]

In some more specific embodiments, the compound has the following structure (IIa):

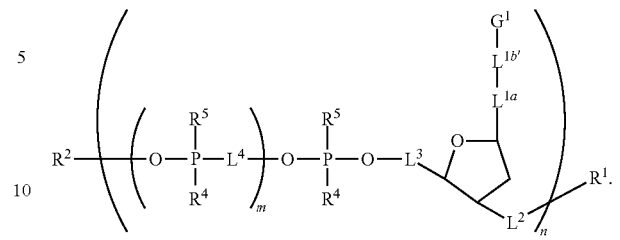

In some related embodiments, the compound has one of the following structures (IIb) or (IIc):

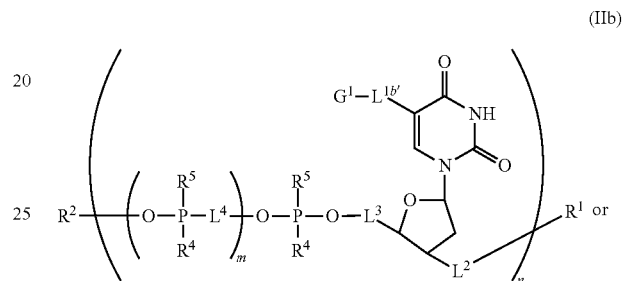

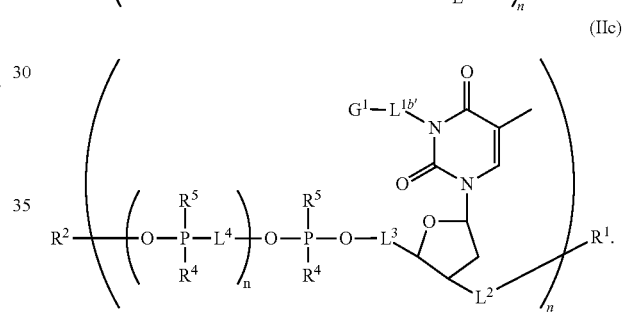

wherein:

$L^{1b'}$ is, at each occurrence, independently an optionally substituted alkylene or an optionally substituted heteroalkylene linker. In some embodiments, $L^{1b'}$ is an optionally substituted heteroalkenylene linker.

In certain embodiments, the compound has one of the following structures (IId) or (IIe):

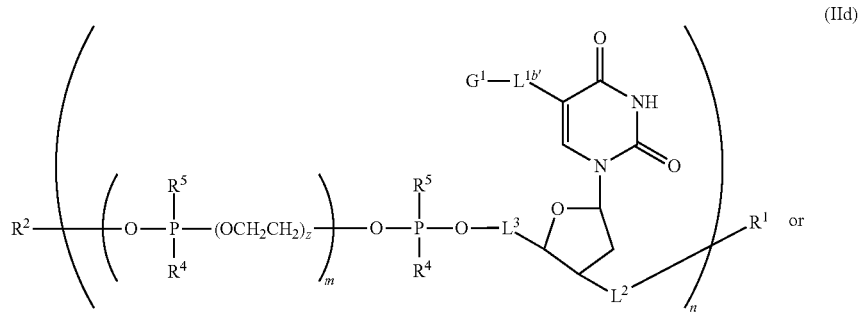

-continued

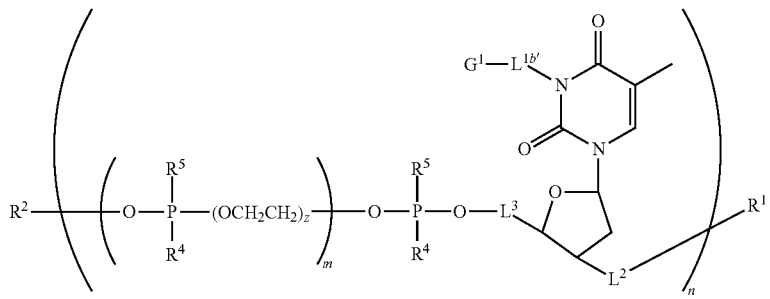

(IIe)

wherein:
z is an integer from 1 to 100.

In certain embodiments, $L^{1b'}$ has one of the following structures:

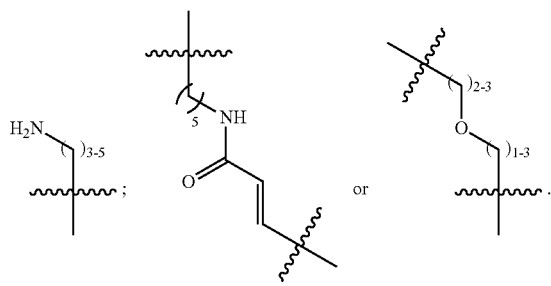

In some specific embodiments, $L^{1b'}$ is an alkylene, for example, ethylene, propylene, butylene or pentylene.

In certain related embodiments, $-L^{1b'}-G^1$ has one of the following structures:

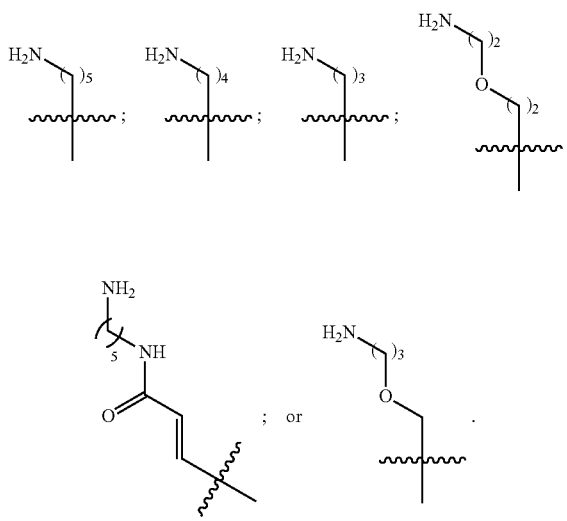

In other embodiments of structure (II), $G^1$ and $G^2$ are, at each occurrence, independently a moiety comprising a reactive group capable of forming a covalent bond with a complementary reactive group.

The $G^1$ and $G^2$ moieties in the compound of structure (II) can be selected from any moiety comprising a group having the appropriate reactivity group for forming a covalent bond with a complementary group on an $M^1$ and/or $M^2$ moiety. In exemplary embodiments, the $G^1$ and $G^2$ moieties can be selected from any of the Q moieties described herein, including those specific examples provided in Table 1. In some embodiments, $G^1$ and $G^2$ at each occurrence, independently comprises a moiety suitable for reactions including: the copper catalyzed reaction of an azide and alkyne to form a triazole (Huisgen 1,3-dipolar cycloaddition), reaction of a diene and dienophile (Diels-Alder), strain-promoted alkyne-nitrone cycloaddition, reaction of a strained alkene with an azide, tetrazine or tetrazole, alkene and azide[3+2]cycloaddition, alkene and tetrazine inverse-demand Diels-Alder, alkene and tetrazole photoreaction and various displacement reactions, such as displacement of a leaving group by nucleophilic attack on an electrophilic atom.

In some embodiments, $G^1$ and $G^2$ are, at each occurrence, independently a moiety comprising an aldehyde, oxime, hydrazone, alkyne, amine, azide, acylazide, acylhalide, nitrile, nitrone, sulfhydryl, disulfide, sulfonyl halide, isothiocyanate, imidoester, activated ester, ketone, α,β-unsaturated carbonyl, alkene, maleimide, α-haloimide, epoxide, aziridine, tetrazine, tetrazole, phosphine, biotin or thiirane functional group. In certain embodiments, at least one occurrence of $G^1$ or $G^2$ has a structure selected from Table 1. In some more specific embodiments, $G^1$ or $G^2$, at each occurrence, independently have a structure selected from Table 1.

In other embodiments, $G^1$ and $G^2$ at each occurrence, independently comprises an alkyne or an azide group. In other embodiments, $G^1$ and $G^2$ at each occurrence, independently comprises an amino, isothiocyanate or activated ester group. In different embodiments, $G^1$ and $G^2$ at each occurrence, independently comprises a reactive group capable of forming a functional group comprising an alkene, ester, amide, thioester, disulfide, carbocyclic, heterocyclic or heteroaryl group, upon reaction with the complementary reactive group. For example, in some embodiment the heteroaryl is triazolyl.

In other of any of the foregoing embodiments of compound (II), $G^1$ and $G^2$ are, at each occurrence, independently

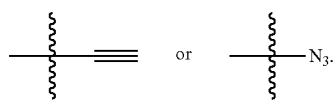

In some embodiments, at least one occurrence of $G^1$ or $G^2$ has one of the following structures:

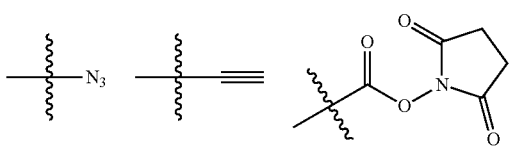

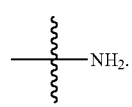

In some related embodiments, $G^1$ or $G^2$, at each occurrence, independently have one of the following structures:

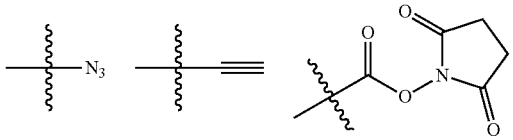

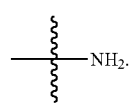

In some embodiments of compound (II), at least one occurrence of $G^1$ is

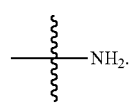

In more specific embodiments, $G^1$ is, at each occurrence, independently

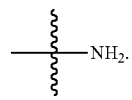

In some embodiments of compound (II), at least one occurrence of $G^1$ or $G^2$ is —$NH_2$. In some embodiments, $G^1$ and $G^2$ are, at a plurality of occurrences, independently —$NH_2$. In certain embodiments, $G^1$ and $G^2$ are, at each occurrence, independently —$NH_2$.

In some embodiments of compound (II), at least one occurrence of $G^1$ and $G^2$ is a protected form of an amine. In some embodiments, $G^1$ and $G^2$ are, at a plurality of occurrences, independently a protected form of an amine. In certain embodiments, $G^1$ and $G^2$ are, at each occurrence, independently a protected form of an amine.

In some of the foregoing embodiments, the protected form of the amine is a trifluoroacetate protected amine. In some embodiments, the protected form of the amine is a BOC protected amine. In some embodiments, the protected form of the amine is an Fmoc protected amine. For example, in certain embodiments, at least one occurrence of $G^1$ or $G^2$ has one of the following structures:

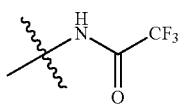 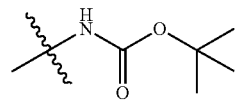

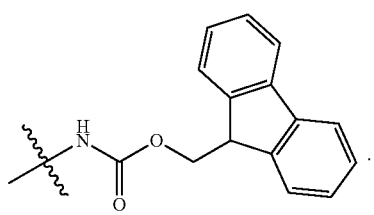

In more specific embodiments, $G^1$ or $G^2$, at each occurrence, independently has one of the following structures:

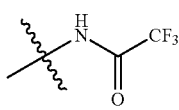 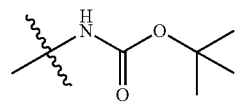

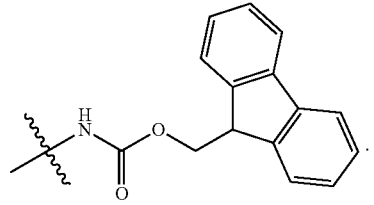

In some embodiments, $R^1$, $R^2$, $R^3$, $R^4$, $R^5$, $L^2$, $L^3$, $L^4$, $L^5$, or $L^6$ are as defined in any one of the foregoing embodiments. For example, in some embodiments of compound (II), $R^4$ is at each occurrence oxo. In some embodiments of compound (II), $R^5$ is at each occurrence, independently OH, $O^-$ or $OR_d$. In certain embodiments of compound (II), $L^2$ is absent at each occurrence. In some specific embodiments of compound (II), $L^3$ is an alkylene linker (e.g., methylene) at each occurrence.

In some embodiments, the compound of structure (II) is a compound of Table 3.

TABLE 3

Exemplary Compounds of Structure II

| No. | Structure |
|---|---|
| II-1 | |
| II-2 | |
| II-3 | |

†Compound II-2 is drawn as a structure representing the average ethylene glycol units As described in detail above, compounds of structures (I) and compounds of structure (II) can be prepared by oligomerization using well known phosphoramidite chemistry. Applicants have discovered intermediate compounds useful for synthesis of compounds of structures (I) and compounds of structure (II). Accordingly, one embodiment provides a compound having the following structure (III):

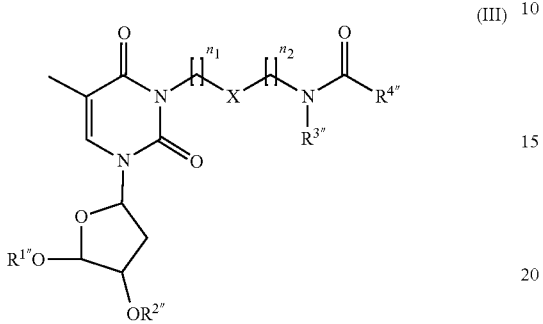

(III)

wherein:
- $n_1$ is an integer from 1 to 6;
- $n_2$ is an integer from 1 to 3;
- X is O or a direct bond;
- $R^{1''}$ and $R^{2''}$ are, at each occurrence, independently H, a protecting group, or an activated phosphorus moiety;
- $R^{3''}$ is H, or alkyl;
- $R^{4''}$ is alkoxy, haloalkyl, alkyl, an optionally substituted aryl or an optionally substituted aralkyl.

In some embodiments of compound (III), $n_1$ is 2. In some embodiments, n is 4. In some related embodiments, $n_2$ is 1. In certain embodiments, $n_1$ is 2 and $n_2$ is 1. In other embodiments, $n_1$ is 4 and $n_2$ is 1. In some of the foregoing embodiments, X is a direct bond.

In some embodiments of compound (III), $n_1$ is 2. In certain related embodiments, $n_2$ is 2. In some of the foregoing embodiments, X is O.

In some embodiments of compound (III), X is a direct bond. In some embodiments, X is O.

In some embodiments of compound (III), $R^{1''}$ is H. In certain embodiments, is a protecting group, for example, a trityl protecting group. In some embodiments, $R^{1''}$ is trityl. In some embodiments, $R^{1''}$ is 4-methoxytrityl. In more specific embodiments, $R^{1''}$ is 4,4'-dimethoxytrityl.

In some embodiments, $R^{2''}$ is H. In some embodiments, $R^{2''}$ is an activated phosphorus moiety. For example, in some embodiments $R^{2''}$ comprises the following structure:

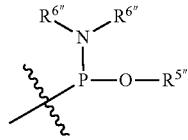

wherein:
- $R^{5''}$ is H or cyano alkyl; and
- $R^{6''}$ is, at each occurrence, independently $C_1$-$C_6$ alkyl.

In some embodiments of compound (III), $R^{5''}$ is H. In other embodiments, $R^{5''}$ is 2-cyanoethyl.

In some embodiments, at least one occurrence of $R^{6''}$ is isopropyl. In some embodiments, each occurrence of $R^{6''}$ is isopropyl.

In certain specific embodiments, $R^{2''}$ has the following structure:

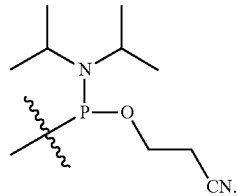 [SMILES: *P(OCCC#N)N(C(C)C)C(C)C]

In some embodiments of compound (III), $R^{3''}$ is H.

In some embodiments of compound (III), $R^{4''}$ is an aryl comprising 1, 2, or 3 aromatic rings, e.g., $R^{4''}$ comprises 1 or 2 aromatic rings. In some embodiments, $R^{4''}$ does not comprise silicon. In some embodiments, $R^{4''}$ is $C_1$-$C_4$ haloalkyl. In more specific embodiments, $R^{4''}$ is —$CF_3$. In some embodiments, $R^{4''}$ is $C_1$-$C_4$ alkoxy. In more specific embodiments, $R^{4''}$ is tert-butoxy.

In some specific embodiments, compound (III) is selected from Table 4.

TABLE 4

Exemplary Compounds of Structure III

| No. | Structure |
|---|---|
| III-1 | 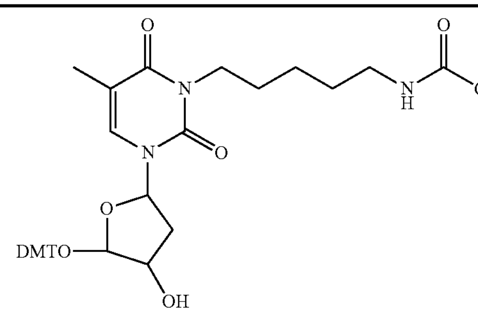 |
| III-2 | 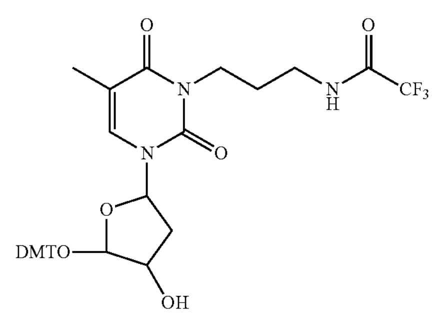 |
| III-4 | 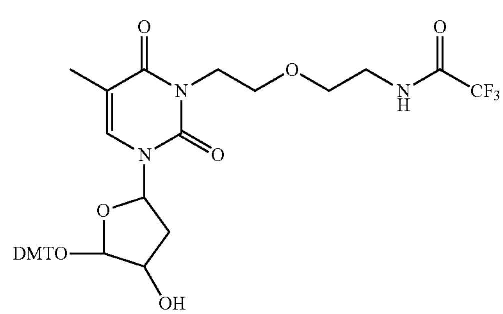 |

The following examples are provided for purposes of illustration, not limitation.

EXAMPLES

General Methods

Mass spectral analysis was performed on a Waters/Micromass Quattro micro MS/MS system (in MS only mode) using MassLynx 4.1 acquisition software. Mobile phase used for LC/MS on dyes was 100 mM 1,1,1,3,3,3-hexafluoro-2-propanol (HFIP), 8.6 mM triethylamine (TEA), pH 8. Phosphoramidites and precursor molecules were also analyzed using a Waters Acquity UHPLC system with a 2.1 mm×50 mm Acquity BEH-$C_{18}$ column held at 45° C., employing an acetonitrile/water mobile phase gradient. Molecular weights for monomer intermediates were obtained using tropylium cation infusion enhanced ionization on a Waters/Micromass Quattro micro MS/MS system (in MS only mode). Excitation and emission profiles experiments were recorded on a Cary Eclipse spectra photometer.

All reactions were carried out in oven dried glassware under a nitrogen atmosphere unless otherwise stated. Commercially available DNA synthesis reagents were purchased from Glen Research (Sterling, VA). Anhydrous pyridine, toluene, dichloromethane, diisopropylethyl amine, triethylamine, acetic acid, pyridine, and THF were purchased from Aldrich. All other chemicals were purchase from Aldrich or TCI and were used as is with no additional purification.

Example 1

Synthesis of Compound I-1

Stock Solution Preparation
  Borate buffer prepared at 250 mM, pH 10
  Fluorscein-NHS solution prepared at 350 mM (300 mg in 1.35 mL DMSO:acetonitrile at 25:75)
Solid Phase Synthesis
  Compound I-1 was prepared on the DNA synthesizer via solid support using standard DNA synthesis techniques (i.e., DMT protected 2-cyanoethyl phosphoramidite). The polymer was removed from the solid support with ammonium hydroxide and lyophilized to a paste. 250 mg aliquots were reconstituted in water. A small aliquot was removed and serial dilutions were prepared in 100 mM $NaCO_3$ at pH 9 to determine concentration (A 263 ε=10,000). Final stock concentration was found to be 14.5 mM.
Dye Coupling Reaction
  In 50 mL centrifuge tube equipped with magnetic stir bar was placed water (1.110 μL), borate buffer (1.800 μL), Compound I-1 polymer solution (466 μL), acetonitrile (137.5 μL), triethylamine (313 μL) and fluorescein-NHS solution (675 μL). The tube was wrapped in aluminum foil and the mixture stirred overnight at room temperature.
Size Exclusion Filtration
  To an Amicon Ultra-15 Centrifugal filter (Millipore UFC900324, MW cutoff=3000) was added 1 mL of water. The crude reaction from the dye coupling reaction (4.5 mL) was added to the filtration setup. The reaction vessel was rinsed 2× with 4 mL of 100 mM NaOH and the rinesates were transferred to the filtration setup. The filtration setup was centrifuged at max speed (3220 g, swing bucket, 30 minutes). The filtrate was removed and the retentate treated with an additional 10 mL of 100 mM NaOH. The filtration setup was centrifuged as before. Again, the filtrate was removed and a third 10 mL 100 mM NaOH aliquot was added to the retentate. The setup was centrifuged as before and the filtrate removed. A fourth 10 mL 100 mM NaOH aliquot was added to the retentate and centrifuged as before. The filtrate was removed and 10 ml of water were added to the filtration setup. The mixture was centrifuged as before. The retentate was removed, the filtration vessel washed with water and the rinesates added to the final volume (3.5 mL). The desired product was confirmed by LC-MS and absorbance was used to determine concentration. A sample of Compound I-1 was also analyzed by PAGE (FIG. 1). FIG. 1 shows Compound A (MW=14104), Compound B (MW=15686) and Compound C (MW=16231) compared to Compound I-2.

Example 2

Synthesis of Compound I-2

Figure 2:
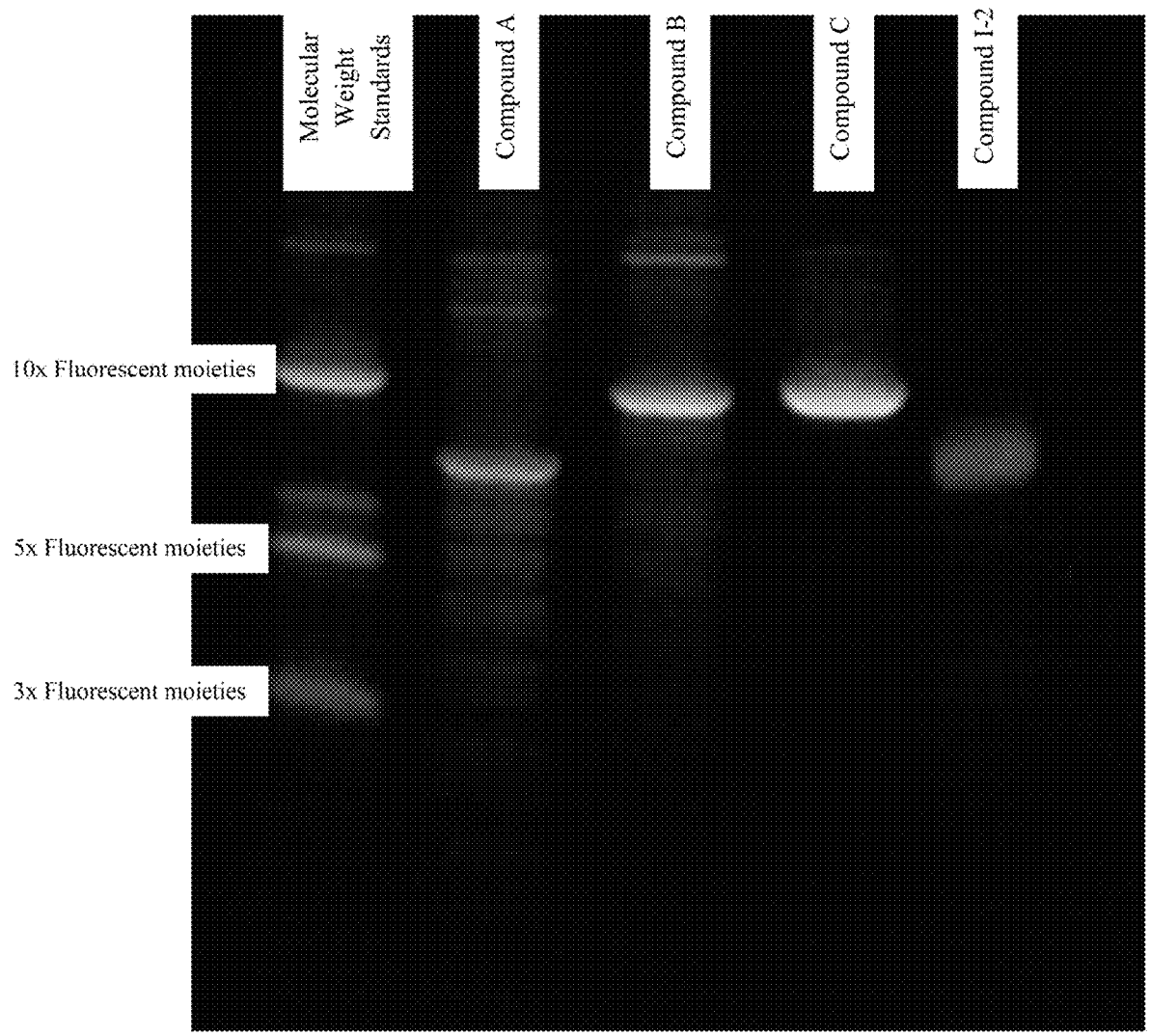
FIG. 2 shows a PAGE gel of Compound I-2 and comparative compounds

Stock Solutions
  Borate buffer was prepared as described in Example 1
  4.6 M Magnesium chloride
  300 mM Fluorscein-NHS solution was prepared in DMSO
Solid Phase Synthesis
  Compound I-2 was prepared on the DNA synthesizer via solid support using standard DNA synthesis techniques (i.e., DMT protected 2-cyanoethyl phosphoramidite). The polymer was removed from the solid support with concentrated ammonium hydroxide and lyophilized to a paste. 20 mg was reconstituted from water and a small aliquot was removed, serial dilutions were prepared in 100 mM $NaCO_3$ at pH 9 to determine concentration (A 263, ε=10,000). Final stock concentration was found to be 11.6 mM.
Dye Coupling Reaction
  In a 200 μL micro-centrifuge tube was placed water (10 μL), borate buffer (20 μL), Compound I-2 polymer solution (2.2 μL), magnesium chloride solution (5.4 μL), DMSO (6.9 μL), fluorescein-NHS solution (5.6 μL). The tube was vortexed and allowed to stand overnight. The mixture was diluted with 50 mL of water and desalted with polyacrylamide desalting columns (Pierce, catalogue #89849). The desired product was confirmed by LC-MS and analyzed by PAGE (FIG. 2). FIG. 2 shows Compound A (MW=14104), Compound B (MW=15686) and Compound C (MW=16231) compared to Compound I-2.

Example 3

Flow Cytometry Method and Applications

A general flow cytometry workflow includes the following steps:
1. Culture and visually observe cells for signs of metabolic stress and/or use fresh, induced, or simulated cells.
2. Dilute dye compounds to working volumes.
3. Harvest and prepare cells without killing or inducing apoptosis.
4. Centrifuge and wash cells with appropriate buffer.
5. Perform cell counts using hemocytometer and trypan blue exclusion.
6. Centrifuge and wash cells
7. Adjust cell density to test size
8. Apply dye (pre-dilution) or other co-stains of interest.
9. Incubate the cell/stain/dye mixture.
10. Centrifuge and wash cells with appropriate buffer.
11. Re-suspend cells in acquisition buffer.
12. Acquire cell data by flow cytometry.

The general workflow described above can be modified according to specific applications. Some modifications for specific applications are described below.

Live/Dead Discrimination

Cells are tested for viability by positively staining necrotic cells to compare damaged cells to intact cells. Assays are used to target non-intact (fixed and non-fixed) cells with positively charged moieties, cell debris, apoptotic bodies, depolarized cell membrane, and permeabilized membranes. Cells are then stained with dye (e.g., Compound I-1) using routine cell preparations (fresh or fixed) and analyzed using flow cytometry.

Cell Health

A comparison is made between dead cells (i.e., necrotic cells), early apoptotic, late apoptotic, and live cells. Dead cells are positively stained, Apoprotic bodies are intermediately stained, and live cells are left negative. This strategy results in very bright necrotic cells and works also to assess cell permeability. Assays are used to target non-intact (fixed and non-fixed) cells with positively charged moieties, cell debris, apoptotic bodies, depolarized cell membrane, and permeabilized membranes. Dye staining is performed on in vitro cultures, primary cells, and samples treated with xenobiotics and analyzed using flow cytometry.

Cell Cycle

Cell ploidy and mitosis in the cell cycle is tracked by staining correlated to positively staining DNA intercalators in all cells and cellular bodies containing nucleic acid and cell cycle associated proteins. Assays are used to target non-intact (non-fixed only) cells with positively charged moieties, cell debris, apoptotic bodies, depolarized cell membrane, and permeabilized membranes. Assays are used to target intact (fixed and permeabilized) cells by staining positively charged moieties after preservation of cells are fixed and permeabilized for intracellular staining. Dye staining (in combination with other dyes) is performed on in vitro cultures, primary cells, and samples treated with xenobiotics and analyzed using flow cytometry.

Proliferation

Cell proliferation is monitored by staining correlated to positively staining DNA intercalators in all cells and cellular bodies containing nucleic acid and cell cycle associated proteins. Assays are used to target non-intact (non-fixed only) cells with positively charged moieties, cell debris, apoptotic bodies, depolarized cell membrane, and permeabilized membranes. Assays are used to target intact (fixed and permeabilized) cells by staining positively charged moieties after preservation of cells are fixed and permeabilized for intracellular staining. Dye staining (in combination with monitoring markers for cell proliferation, e.g. Ki67, BRDU) is performed on in vitro cultures, primary cells, and samples treated with xenobiotics and analyzed using flow cytometry.

Example 4

Activation and Antibody Conjugation of Compound I-1

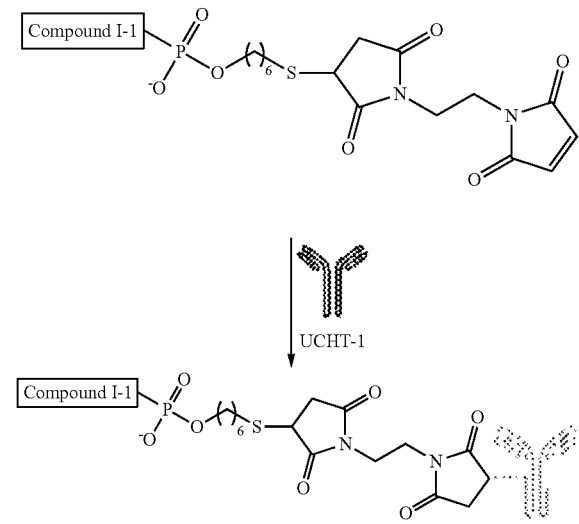

The maleimide functionalized Compound I-1 is prepared according to the method described in Example 1. In parallel, an UCHT-1 antibody is treated with bis-maleimidoethane ("BMOE") to reduce disulfide bonds. The reduced antibody is reacted with Compound I-1 in a 5:1 molar ratio of polymer to antibody. The reaction results in a final product having a polymer to antibody ratio of 1:1 as detected by size exclusion chromatography.

All of the U.S. patents, U.S. patent application publications, U.S. patent applications, foreign patents, foreign patent applications and non-patent publications referred to in this specification, including U.S. Provisional Patent Application No. 62/690,656, filed Jun. 27, 2018, are incorporated herein by reference, in their entirety to the extent not inconsistent with the present description.

From the foregoing it will be appreciated that, although specific embodiments of the disclosure have been described herein for purposes of illustration, various modifications may be made without deviating from the spirit and scope of the disclosure. Accordingly, the disclosure is not limited except as by the appended claims.

What is claimed is:

1. A compound having the following structure (Ia):

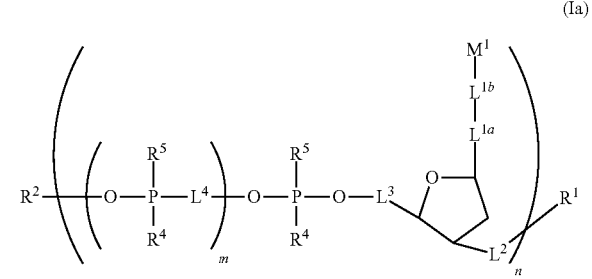

or a stereoisomer, salt or tautomer thereof, wherein:

M¹ is, at each occurrence, independently a moiety comprising an active drug moiety;

L¹ᵃ is, at each occurrence, independently a heteroarylene linker;

L¹ᵇ, L², and L³ are, at each occurrence, independently optional alkylene, alkenylene, alkynylene, heteroalkylene, heteroalkenylene or heteroalkynylene linkers;

L⁴ is, at each occurrence, independently an alkylene, alkenylene, alkynylene, heteroalkylene, heteroalkenylene or heteroalkynylene linker;

R¹ and R² are each independently H, OH, SH, alkyl, alkoxy, alkylether, heteroalkyl, —OP(=R$_a$)(R$_b$)R$_c$, Q, or L';

R⁴ is, at each occurrence, independently OH, SH, O⁻, S⁻, OR$_d$ or SR$_d$;

R⁵ is, at each occurrence, independently oxo, thioxo or absent;

R$_a$ is O or S;

R$_b$ is OH, SH, O⁻, S⁻, OR$_d$ or SR$_d$;

R$_c$ is OH, SH, O⁻, S⁻, OR$_d$, OL', SR$_d$, alkyl, alkoxy, heteroalkyl, heteroalkoxy, alkylether, alkoxyalkylether, phosphate, thiophosphate, phosphoalkyl, thiophosphoalkyl, phosphoalkylether or thiophosphoalkylether;

R$_d$ is a counter ion;

Q is, at each occurrence, independently a moiety comprising a sulfhydryl, disulfide, activated ester, isothiocyanate, azide, alkyne, alkene, diene, dienophile, acid halide, sulfonyl halide, phosphine, α-haloamide, biotin, amino or maleimide functional group;

L' is, at each occurrence, independently comprises an alkylene or heteroalkylene linker covalently bonded to: Q, a targeting moiety selected from an antibody and a cell surface receptor antagonist, a solid support selected from a polymeric bead and a non-polymeric bead, or a nucleoside;

m is, at each occurrence, an integer of one or greater; and n is an integer of one or greater.

2. The compound of claim 1, wherein L¹ᵃ has one of the following structures:

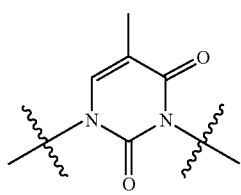 or 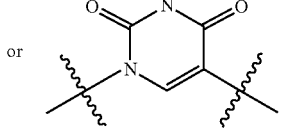

3. The compound of claim 1, wherein at least one occurrence of L³ is an alkylene linker and at least one occurrence of L⁴ comprises alkylene oxide.

4. The compound of claim 1, wherein the compound has one of the following structures (Ib) or (Ic):

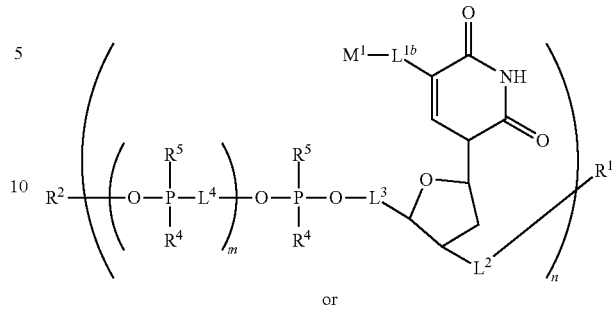

(Ib)

or

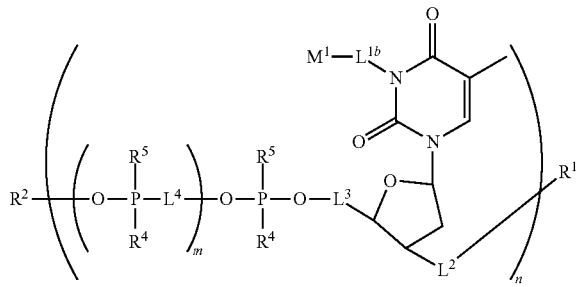

(Ic)

wherein:

L¹ᵇ is, at each occurrence, independently an alkylene or heteroalkylene linker.

5. The compound of claim 1, wherein L⁴ is polyethylene oxide, and the compound has the following structure (Id) or (Ie):

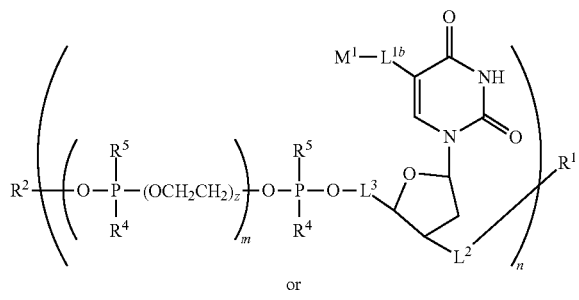

(Id)

or

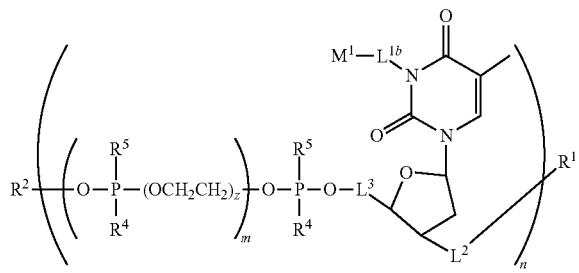

(Ie)

wherein:

z is an integer from 1 to 100.

6. The compound of claim 1, wherein L¹ᵇ, at each occurrence, independently comprises an amide functional group or a triazolyl functional group.

7. The compound of claim 1, wherein R⁴ is, at each occurrence, oxo, and R⁵ is, at each occurrence, independently OH, O⁻ or OR_d.

8. The compound of claim 1, wherein R¹ and R² are each independently —OP(=R_a)(R_b)R_c.

9. The compound of claim 8, wherein R_c is OL', wherein L' comprises a heteroalkylene linker to: Q, a targeting moiety, an analyte molecule, a solid support, a solid support residue or a nucleoside.

10. The compound of claim 9, wherein L' comprises an alkylene oxide or phosphodiester moiety, or combinations thereof.

11. The compound of claim 10, wherein L' has the following

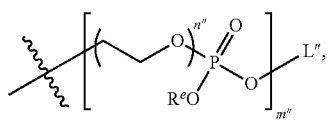

wherein:
m" and n" are independently an integer from 1 to 10;
R^e is H, an electron pair or a counter ion;
L" is R^e or a direct bond or comprises an alkylene linkage to: Q, a targeting moiety, an analyte molecule, a solid support, or a nucleoside.

12. The compound of claim 11, wherein the targeting moiety is an antibody or cell surface receptor antagonist.

13. The compound of claim 1, wherein R¹ or R² has one of the following structures:

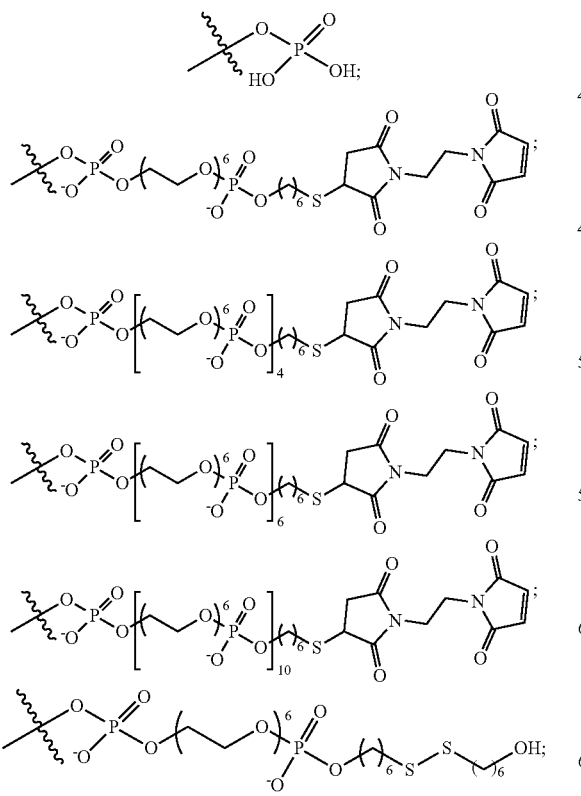

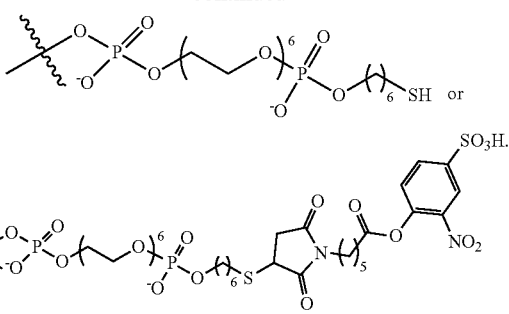

14. The compound of claim 1, wherein Q is a moiety having one of the following structures:

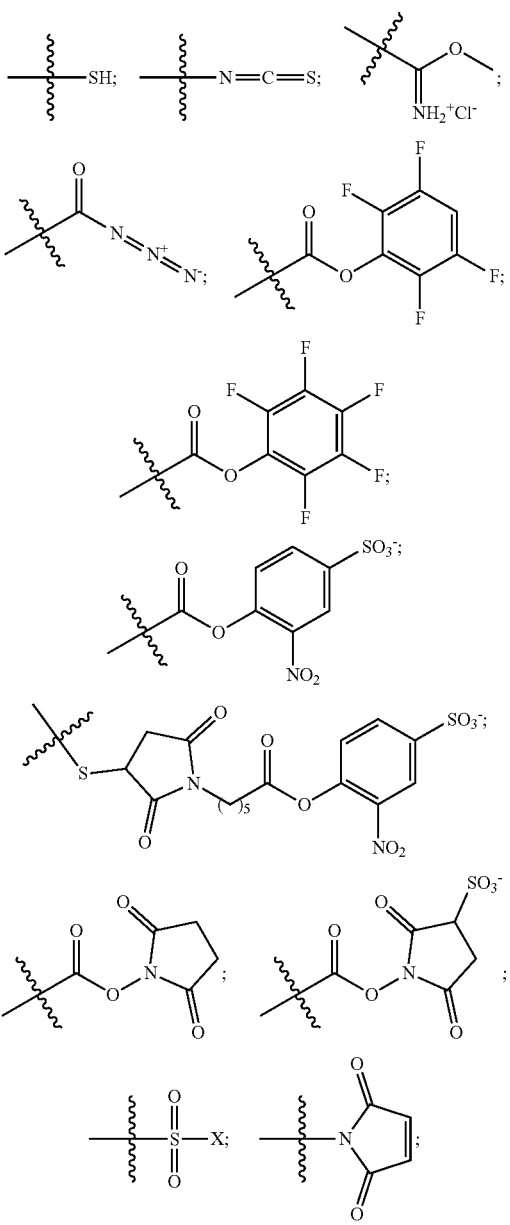

-continued

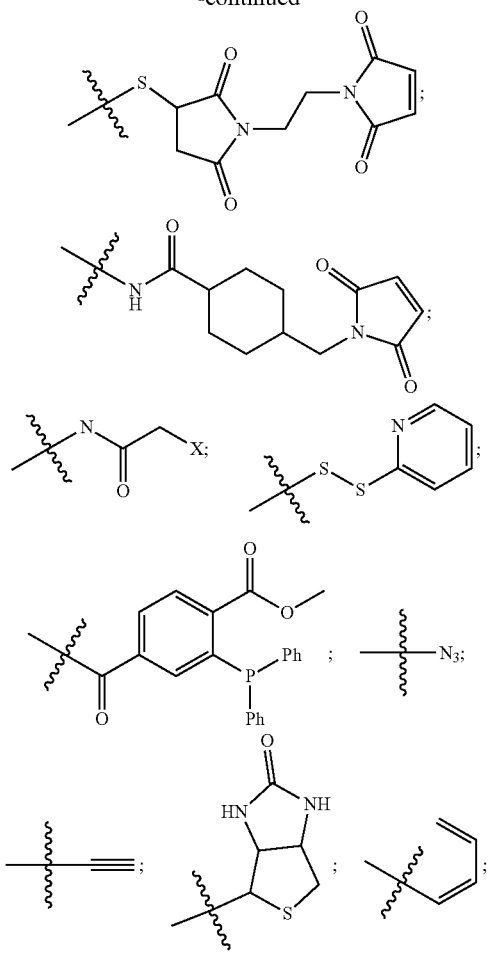

-continued

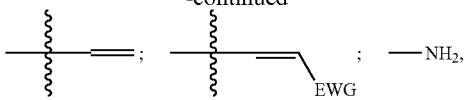

wherein:
X is halo; and
EWG is an electron withdrawing group.

15. The compound of claim 1, wherein n is an integer from 1 to 10 and m is an integer from 3 to 12.

16. A method for visually detecting an analyte molecule, the method comprising:
(a) providing the compound of claim 1, wherein $R^1$ or $R^2$ is a linker comprising a covalent bond to the analyte molecule; and
(b) detecting the compound by its visible properties.

17. A method for visually detecting an analyte molecule, the method comprising:
(a) admixing the compound of claim 1, wherein $R^1$ or $R^2$ is Q or a linker comprising a covalent bond to Q, with the analyte molecule;
(b) forming a conjugate of the compound and the analyte molecule; and
(c) detecting the conjugate by its visible properties.

18. A method for visually detecting an analyte, the method comprising:
(a) providing the compound of claim 1, wherein $R^1$ or $R^2$ comprises a linker comprising a covalent bond to a targeting moiety having specificity for the analyte;
(b) admixing the compound and the analyte, thereby associating the targeting moiety and the analyte; and
(c) detecting the compound by its visible properties.

19. A composition comprising the compound of claim 1 and one or more analyte molecules.

20. The composition of claim 1, wherein $L^2$ is absent at each occurrence.

* * * * *

UNITED STATES PATENT AND TRADEMARK OFFICE
CERTIFICATE OF CORRECTION

Page 1 of 1

PATENT NO. : 12,391,833 B2
APPLICATION NO. : 18/678656
DATED : August 19, 2025
INVENTOR(S) : Sharat Singh et al.

It is certified that error appears in the above-identified patent and that said Letters Patent is hereby corrected as shown below:

In the Claims

<u>Column 69, Claim 11, Line 15:</u>
"following" should read: --following:--.

Signed and Sealed this
Twenty-first Day of October, 2025

John A. Squires
*Director of the United States Patent and Trademark Office*